US011655468B2

(12) United States Patent
Gao

(10) Patent No.: US 11,655,468 B2
(45) Date of Patent: May 23, 2023

(54) METHODS AND COMPOSITIONS OF CHEMICALLY MODIFIED PHAGE LIBRARIES

(71) Applicant: The Trustees of Boston College, Chestnut Hill, MA (US)

(72) Inventor: Jianmin Gao, Newton, MA (US)

(73) Assignee: The Trustees of Boston College, Chesnut Hill (MA)

( * ) Notice: Subject to any disclaimer, the term of this patent is extended or adjusted under 35 U.S.C. 154(b) by 203 days.

(21) Appl. No.: 17/156,908

(22) Filed: Jan. 25, 2021

(65) Prior Publication Data

US 2021/0198657 A1 Jul. 1, 2021

Related U.S. Application Data

(63) Continuation of application No. PCT/US2019/004321, filed on Jul. 24, 2019.

(60) Provisional application No. 62/702,990, filed on Jul. 25, 2018.

(51) Int. Cl.

| | |
|---|---|
| ***C12N 7/00*** | (2006.01) |
| ***A61K 45/06*** | (2006.01) |
| ***C12N 15/10*** | (2006.01) |
| ***G01N 33/50*** | (2006.01) |

(52) U.S. Cl.

CPC .......... *C12N 15/1037* (2013.01); *A61K 45/06* (2013.01); *C12N 7/00* (2013.01); *G01N 33/5008* (2013.01); *C12N 2795/00011* (2013.01)

(58) Field of Classification Search

None

See application file for complete search history.

(56) References Cited

U.S. PATENT DOCUMENTS

| | | | |
|---|---|---|---|
| 2004/0266789 | A1 | 12/2004 | Whitehouse et al. |
| 2009/0148887 | A1 | 6/2009 | Brustad et al. |
| 2015/0166988 | A1 | 6/2015 | Winter et al. |
| 2015/0329568 | A1 | 11/2015 | Tuttle et al. |

FOREIGN PATENT DOCUMENTS

| | | | |
|---|---|---|---|
| WO | 2013084198 | A1 | 6/2013 |

OTHER PUBLICATIONS

Blair, Jessica MA, et al. "Molecular mechanisms of antibiotic resistance." Nature reviews microbiology 13.1 (2015): 42-51.

Fischbach, Michael A; et al. "Antibiotics for emerging pathogens." Science 325.5944 (2009): 1089-1093.

Modi, Sheetal R.; et al. "Antibiotics and the gut microbiota." The Journal of clinical investigation 124.10 (2014): 4212-4218.

Lehar, Sophie M., et al. "Novel antibody-antibiotic conjugate eliminates intracellular *S. aureus.*" Nature 527.7578 (2015): 323-328.

Mariathasan, Sanjeev; et al. "Antibody-antibiotic conjugates: a novel therapeutic platform against bacterial infections." Trends in molecular medicine 23.2 (2017): 135-149.

Kumaresan, Pappanaicken R., et al. "Rapid discovery of death ligands with one-bead-two-compound combinatorial ibrary methods." ACS combinatorial science 13.3 (2011): 259-264.

Qian, Ziqing; et al. "Synthesis and screening of one-bead-one-compound cyclic peptide libraries." Peptide Libraries (2015): 39-53.

Jagadish, Krishnappa, et al. "Recombinant Expression and Phenotypic Screening of a Bioactive Cyclotide Against a-Synuclein-Induced Cytotoxicity in Baker's Yeast." Angewandte Chemie 127.29 (2015): 8510-8514.

Owens, Andrew E., et al. "Design and evolution of a macrocyclic peptide inhibitor of the sonic hedgehog/patched interaction." Journal of the American Chemical Society 139.36 (2017): 12559-12568.

Hamzeh-Mivehroud, Maryam, et al. "Phage display as a technology delivering on the promise of peptide drug discovery." Drug discovery today 18.23-24 (2013): 1144-1157.

Huang, Johnny X.; et al. "Development of anti-infectives using phage display: biological agents against bacteria, viruses, and parasites." Antimicrobial agents and chemotherapy 56.9 (2012): 4569-4582.

Ng, Simon; et al. "Bacteriophages and viruses as a support for organic synthesis and combinatorial chemistry." ACS chemical biology 7.1 (2012): 123-138.

Mohan, Kritika; et al. "Chemically modifying viruses for diverse applications." ACS chemical biology 11.5 (2016): 1167-1179.

Day, Jonathan W., et al. "Identification of metal ion binding peptides containing unnatural amino acids by phage display." Bioorganic & medicinal chemistry letters 23.9 (2013): 2598-2600.

Heinis, Christian, et al. "Phage-encoded combinatorial chemical libraries based on bicyclic peptides." Nature chemical biology 5.7 (2009): 502-507.

Ng, Simon, et al. "Quantitative synthesis of genetically encoded glycopeptide libraries displayed on M13 phage." ACS chemical biology 7.9 (2012): 1482-1487.

(Continued)

*Primary Examiner* — Nianxiang Zou

(74) *Attorney, Agent, or Firm* — Lei Fang, Esq.; Smith Tempel Blaha LLC

(57) ABSTRACT

Provided is a chemically modified phage display platform and method of use thereof. More specifically, the present disclosure provides a chemically modified phage display library that incorporates 2-acetylphenylboronic acid (APBA) moieties to elicit dynamic covalent binding to the bacterial cell surface. The APBA-modified phage display libraries described herein are applicable to a wide array of bacterial strains and/or mammalian cells, paving the way to facile diagnosis and development of strain-specific antibiotics, and/or peptide-antibiotic conjugates for effective and targeted treatment. Also provided are therapeutic peptides, and pharmaceutical compositions thereof, that are identified by screening the phage display library of the present disclosure, and method of use of such therapeutic peptides for effective and targeted treatment.

20 Claims, 34 Drawing Sheets
(32 of 34 Drawing Sheet(s) Filed in Color)

Specification includes a Sequence Listing.

(56) References Cited

OTHER PUBLICATIONS

Bandyopadhyay, Anupam; et al. "Targeting biomolecules with reversible covalent chemistry." Current opinion in chemical biology 34 (2016): 110-116.
Bandyopadhyay, Anupam, et al. "Targeting bacteria via iminoboronate chemistry of amine-presenting lipids." Nature communications 6.1 (2015): 1-9.
Cal, Pedro MSD, et al. "Reversible lysine modification on proteins by using functionalized boronic acids." Chemistry—A European Journal 21.22 (2015): 8182-8187.
Akçay, Gizem, et al. "Inhibition of Mcl-1 through covalent modification of a noncatalytic lysine side chain." Nature chemical biology 12.11 (2016): 931-936.
Jafari, Mohammad R., et al. "Discovery of light-responsive ligands through screening of a light-responsive genetically encoded library." ACS chemical biology 9.2 (2014): 443-450.
Bandyopadhyay, Anupam; et al. "Fast diazaborine formation of semicarbazide enables facile labeling of bacterial pathogens." Journal of the American Chemical Society 139.2 (2017): 871-878.
Gasanov, Uta, et al. "Identification of the insulin-like growth factor II receptor as a novel receptor for binding and invasion by Listeria monocytogenes." Infection and immunity 74.1 (2006): 566-577.
Andrä, Jörg, et al. "Multiple peptide resistance factor (MprF)-mediated resistance of *Staphylococcus aureus* against antimicrobial peptides coincides with a modulated peptide interaction with artificial membranes comprising lysyl-phosphatidylglycerol." Journal of Biological Chemistry 286.21 (2011): 18692-18700.
Slavetinsky, Christoph; et al. "Bacterial aminoacyl phospholipids-Biosynthesis and role in basic cellular processes and pathogenicity." Biochimica et Biophysica Acta (BBA)—Molecular and Cell Biology of Lipids 1862.11 (2017): 1310-1318.
Bandyopadhyay, Anupam; et al. "Iminoboronate-based peptide cyclization that responds to pH, oxidation, and small molecule modulators." Journal of the American Chemical Society 138.7 (2016): 2098-2101.
Peschel, Andreas, et al. "*Staphylococcus aureus* resistance to human defensins and evasion of neutrophil killing via the novel virulence factor MprF is based on modification of membrane lipids with l-lysine." The Journal of experimental medicine 193.9 (2001): 1067-1076.
Dosselli, Ryan, et al. "Porphyrin-apidaecin conjugate as a new broad spectrum antibacterial agent." ACS medicinal chemistry letters 1.1 (2010): 35-38.
Liu, Fang, et al. "Lipopolysaccharide neutralizing peptide-porphyrin conjugates for effective photoinactivation and intracellular imaging of Gram-negative bacteria strains." Bioconjugate chemistry 23.8 (2012): 1639-1647.
Kasimova, Kamola R., et al. "Potentiation of photoinactivation of Gram-positive and Gram-negative bacteria mediated by six phenothiazinium dyes by addition of azide ion." Photochemical & photobiological sciences 13.11 (2014): 1541-1548.
Johnson, Gregory A.; et al. "Photoinactivation of Gram positive and Gram negative bacteria with the antimicrobial peptide (KLAKLAK) 2 conjugated to the hydrophilic photosensitizer eosin Y." Bioconjugate chemistry 24.1 (2013): 114-123.
Alves, Eliana, et al. "Charge effect on the photoinactivation of Gram-negative and Gram-positive bacteria by cationic meso-substituted porphyrins." BMC microbiology 9.1 (2009): 1-13.
Sperandio, F. F.; et al. "Antimicrobial Photodynamic Therapy to Kill Gram-negative Bacteria" Recent Pat Antiinfect Drug Discov. (2013) 8(2): 108-120.
Peleg, Anton Y.; et al. "Acinetobacter baumannii: emergence of a successful pathogen." Clinical microbiology reviews 21.3 (2008): 538-582.
Arroyo, Luis A., et al. "The pmrCAB operon mediates polymyxin resistance in Acinetobacter baumannii ATCC 17978 and clinical isolates through phosphoethanolamine modification of lipid A." Antimicrobial agents and chemotherapy 55.8 (2011): 3743-3751.
Boll, Joseph M., et al. "A penicillin-binding protein inhibits selection of colistin-resistant, lipooligosaccharide-deficient Acinetobacter baumannii" Proceedings of the National Academy of Sciences 113.41 (2016): E6228-E6237.
Powers, Matthew Joseph; et al. "Expanding the paradigm for the outer membrane: Acinetobacter baumannii in the absence of endotoxin." Molecular microbiology 107.1 (2018): 47-56.
Jacobs, Anna C., et al. "AB5075, a highly virulent isolate of Acinetobacter baumannii, as a model strain for the evaluation of pathogenesis and antimicrobial treatments." MBio 5.3 (2014).
Kristian, Sascha A., et al. "D-alanylation of teichoic acids promotes group a *Streptococcus* antimicrobial peptide resistance, neutrophil survival, and epithelial cell invasion." Journal of Bacteriology 187.19 (2005): 6719-6725.
Brown, Stephanie; et al. "Wall teichoic acids of gram-positive bacteria." Annual review of microbiology 67 (2013): 313-336.
Needham, Brittany D; et al. "Fortifying the barrier: the impact of lipid A remodelling on bacterial pathogenesis." Nature Reviews Microbiology 11.7 (2013): 467-481.
International Search Report and Written Opinion dated Oct. 28, 2019 for PCT Patent Application PCT/US2019/043211.
Diemer, Sanna L., et al. "Simultaneous Disulfide and Boronic Acid Ester Exchange in Dynamic Combinatorial Libraries." International journal of molecular sciences 16.9 (2015): 21858-21872.
McCarthy, Kelly A., et al. "Phage display of dynamic covalent binding motifs enables facile development of targeted antibiotics." Journal of the American Chemical Society 140.19 (2018): 6137-6145.

C

APBA-IA Biotin-IA Scz-FITC

KAM5: AC*VSPRSHEC*GGG(Dap*); KAM6: AC*GPTAKYIC*GGG(Dap*)
C*: APBA-IA labeled cysteine; Dap*: fluorophore-labeled Dap 1 2 3 4 5 a b

A

APBA-IA

B vancomycin
D1 daptomycin
D2 colistin
D3

SMAMP-02 (brilacidin mimic)
D4

LTX-109
D5 peptidomimetic
D6

A

B

2-APBA

METHODS AND COMPOSITIONS OF CHEMICALLY MODIFIED PHAGE LIBRARIES

CROSS-REFERENCE TO RELATED APPLICATION

This is a continuation of a PCT International Application No. PCT/US2019/043211, filed on Jul. 24, 2019, which claims benefit and priority to U.S. Provisional Application No. 62/702,990, filed on Jul. 25, 2018, the entire contents of both are hereby incorporated by reference.

STATEMENT OF GOVERNMENT SUPPORT

The current technology was developed in part using funds supplied by the National Institutes of Health (NIH) under grant No. GM102735. Accordingly, the U.S. Government has certain rights to this invention.

SEQUENCE LISTING

The instant application contains a Sequence Listing which has been submitted electronically in ASCII format and is hereby incorporated by reference in its entirety. Said ASCII copy, created on Jul. 24, 2019, is named 940203_2010_SL.txt and is 73,158 bytes in size.

FIELD OF THE INVENTION

The present invention is directed to novel chemically modified phage libraries.

BACKGROUND OF THE INVENTION

Antibiotic resistant bacterial pathogens have become a global threat to public health. Diverse mechanisms of resistance of essentially all current antibiotics have been elucidated in recent years and are continuously being discovered. According to the Center for Disease Control, over 2 million antibiotic-resistant infections are reported each year leading to approximately 23,000 deaths in the United States alone. Although resistance occurs naturally, misuse and overuse of broad-spectrum antibiotics in humans and animals accelerates the process. There is thus an urgent need for a change in the way antibiotics are utilized along with the development of novel antimicrobial agents. Ideally, to avoid unintentional elicitation of antibiotic resistance, it would be advantageous to replace widely used broad-spectrum antibiotics with narrow-spectrum antibiotics. Furthermore, the use of broad-spectrum antibiotics can cause undesirable disruptions to the microbiota, which plays critical roles in various aspects of human biology.

The development of narrow-spectrum antibiotics requires novel strategies that enable specific targeting of a bacterial strain of interest. There are only a handful of examples in literature describing targeted antibiotics, including those utilizing antibodies as targeting motifs. While effective, the development of an antibody drug is nontrivial and can be quite costly. In contrast, screening diverse peptide libraries presents a great opportunity for the discovery of potent and selective targeting motifs for a specific target. A versatile and high throughput version of such peptide screening strategies makes use of phage display, in which a peptide scaffold of interest is fused to a bacteriophage coat protein. Phage display has been used extensively for studying protein-protein interactions and discovering peptide ligands for various targets including specific biomolecules as well as intact cells. Until recently, the phage-display technology was limited to presenting peptides only composed of natural, proteinogenic amino acids. Due to technological advances in the field, phage libraries can now be chemically and genetically modified to present unnatural entities, which greatly expand the chemical space of phage displayed molecules. For example, selective cysteine alkylation has been utilized to create bicyclic peptide libraries on phage. Similarly, a glycopeptide library has been developed through oxidative cleavage of an N-terminal serine or threonine that yields a bioorthogonal aldehyde handle for conjugation to carbohydrates.

Antibiotic resistance of bacterial pathogens poses an increasing threat to the wellbeing of society and urgently calls for new strategies for infection diagnosis and antibiotic discovery. The antibiotic resistance problem to a large extent arises from extensive use of broad-spectrum antibiotics. Ideally, for the treatment of infection, one would like to use a narrow-spectrum antibiotic that specifically targets and kills the disease causing strain. This is particularly important considering the commensal bacterial species that are beneficial and sometimes even critical to the health of a human being.

SUMMARY OF THE INVENTION

Further expanding the chemical space of phage display, the present disclosure provides a novel phage display library that incorporates chemical modification of phage displayed peptides. In certain embodiments, the chemical modification motifs are dynamic covalent binding motifs. In certain embodiments, the covalent binding motif is a pair of 2-acetylphenylboronic acid (APBA) moieties that are installed onto phage displayed peptides to bind biological amines via dynamic formation of iminoboronates. The present disclosure provides chemical modification of phage displayed peptides yields an APBA dimer library.

In certain embodiments, the display peptides of the APBA dimer phage library are linear peptides. In other embodiments, the display peptides of the APBA dimer phage library are cyclic and/or multicyclic peptides wherein crosslinks are introduced to the linear peptide architecture to general cyclic and/or multicyclic peptides. These cyclic and/or multicyclic peptide libraries maximize the chance of success for a diverse range of bacterial pathogens.

In certain embodiments, the present disclosure provides that the APBA dimer phage library can be extended to discover binders of various bacterial pathogens. In certain embodiments, screening of the iminoboronate-capable APBA dimer library of the present disclosure against live bacterial cells yielded potent and selective binders of *Staphylococcus aureus* as well as a colistin-resistant strain of *Acinetobacter baumannii*. The present disclosure further provides that these bacterial binders identified from the APBA dimer phage library can be readily converted to targeted antibiotics that specifically eradicate the corresponding strain of bacteria. The iminoboronate-capable APBA dimer phage library provided herein serves as a powerful tool to advance the development of narrow-spectrum antibiotics.

In certain embodiments, the present disclosure further provides that antibiotics of other modes of action, such as those targeting cell membranes, including but not limited to, vancomycin and daptomycin, can be utilized to build peptide-antibiotic conjugates for effective and targeted bacterial cell killing. The chemically modified phage library described herein provides a convenient way to screen live intact bacterial for potential target, and can also be readily adapted to other targets including mammalian cells.

Therefore, the present disclosure provides the iminoboronate-capable APBA dimer phage libraries that provide advancement in bacterial imaging reagents or novel antibiotics. The disclosed APBA dimer phage display libraries are applicable for drug screening for selection of functional molecules towards a variety of different targets. The disclosed APBA dimer phage display libraries can also be used for the development of novel protein inhibitors. The present disclosure provides a new paradigm for the development of targeted antibiotics and/or peptide-antibiotic conjugates.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

Figure 1A:
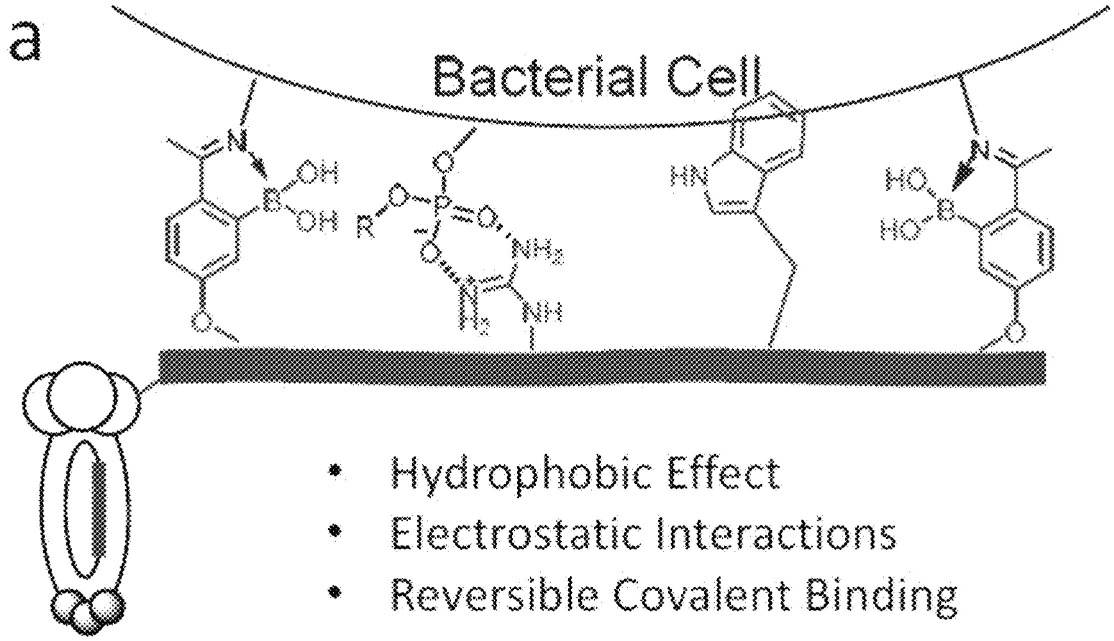
FIGS. 1A-1D show modification of Ph.D.-C7C library with APBA warheads. (A). illustration of a modified phage binding to bacterial cells via iminoboronate formation. (B). Illustration of the cysteine labeling strategy to display 2-APBA on phage (SEQ ID NOS: 268-269, respectively, in order of appearance). (C). Structure of the chemical modifiers of the C7C phage library. (D). Confirmation of APBA labeling of phage via fluorescent gel imaging after conjugation with Scz-FITC. Lane 1: ladder imaged at 660 nm; Lane 2: ladder imaged at 495 nm; Lane 3: reduced phage; Lane 4: Biotin-IA labeled phage; and Lane 5: 2-APBA labeled phage.

Additional advantages of the disclosure will be set forth in part in the description which follows, and in part will be obvious from the description, or can be learned by practice of the disclosure. The advantages of the disclosure will be realized and attained by means of the elements and combinations particularly pointed out in the appended claims. It is to be understood that both the foregoing general description and the following detailed description are exemplary and explanatory only and are not restrictive of the disclosure, as claimed.

DETAILED DESCRIPTION OF THE INVENTION

The present disclosure provides novel chemically modified phage libraries and applications and/or use of such chemically modified phage libraries. In certain embodiments, the present disclosure provides the construction and validation of a phage library displaying reversible covalent binding motifs incorporated onto the display peptides. Specifically, chemical modification of phage displayed peptides yields an APBA dimer library, which allows facile screening against bacterial cells to identify reversible covalent binders of specific bacterial strains. In certain embodiments, the display peptides are linear peptides. In other embodiments, the display peptides are cyclic and/or multicyclic peptides in which crosslinks are introduced to the linear peptide architecture to generate cyclic and/or multicyclic peptides. The APBA dimer phage libraries with the cyclic and/or multicyclic peptides maximize the chance of success for a diverse range of bacterial pathogens.

The present disclosure further provides use of the novel chemically modified phage libraries for drug screening for functional molecules toward a variety of different targets. In certain embodiments, the present disclosure provides a drug screening method of screening the chemically modified phage libraries with live bacterial cells which leads to develop bacterial imaging reagents, as well as novel antibiotics. In other embodiments, the present disclosure provides the use of the chemically modified phage libraries for quick discovery of targeted antibiotics, which, in comparison to the currently used broad-spectrum antibiotics, could reduce the unnecessary cultivation of antibiotic resistance and minimize the disruption of host microbiota. Furthermore, the present disclosure provides novel chemically modified phage libraries for advancement in bacterial targeting and/or imaging reagents, and or novel antibiotics, as well as for novel protein inhibitors and/or for peptide-antibiotic conjugates. The present disclosure thus provides a new paradigm for such development of targeted antibiotics and/or peptide-antibiotic conjugates for effective and targeted bacterial cell killing.

Although specific terms are employed herein, they are used in a generic and descriptive sense only and not for purposes of limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

Any recited method can be carried out in the order of events recited or in any other order that is logically possible. That is, unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant application should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

While aspects of the present disclosure can be described and claimed in a particular statutory class, such as the system statutory class, this is for convenience only and one of skill in the art will understand that each aspect of the present disclosure can be described and claimed in any statutory class.

It is also to be understood that the terminology used herein is for the purpose of describing particular aspects only and is not intended to be limiting. Unless defined otherwise, all technical and scientific terms used herein have the same meaning as commonly understood by one of ordinary skill in the art to which the disclosed compositions and methods belong. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

Aspects of the present disclosure will employ, unless otherwise indicated, techniques of molecular biology, microbiology, organic chemistry, biochemistry, physiology, cell biology, blood vessel biology, and the like, which are within the skill of the art. Such techniques are explained fully in the literature.

Prior to describing the various aspects of the present disclosure, the following definitions are provided and should be used unless otherwise indicated. Additional terms may be defined elsewhere in the present disclosure.

Definitions

As used herein, "comprising" is to be interpreted as specifying the presence of the stated features, integers, steps, or components as referred to, but does not preclude the presence or addition of one or more features, integers, steps, or components, or groups thereof. Moreover, each of the terms "by", "comprising," "comprises", "comprised of," "including," "includes," "included," "involving," "involves," "involved," and "such as" are used in their open, non-limiting sense and may be used interchangeably. Further, the term "comprising" is intended to include examples and aspects encompassed by the terms "consisting essentially of" and "consisting of." Similarly, the term "consisting essentially of" is intended to include examples encompassed by the term "consisting of.

As used in the specification and the appended claims, the singular forms "a," "an" and "the" include plural referents unless the context clearly dictates otherwise. Thus, for example, reference to "a peptide," "an amino acid," or "a cell," including, but not limited to, two or more such peptides, amino acids, or cells, including combinations of peptides, amino acids, or cells, and the like.

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

Where a range is expressed, a further aspect includes from the one particular value and/or to the other particular value. Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used herein, "about," "approximately," "substantially," and the like, when used in connection with a numerical variable, can generally refers to the value of the variable and to all values of the variable that are within the experimental error (e.g., within the 95% confidence interval for the mean) or within +/−10% of the indicated value, whichever is greater. As used herein, the terms "about," "approximate," "at or about," and "substantially" can mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

As used herein, the terms "optional" or "optionally" means that the subsequently described event or circumstance can or cannot occur, and that the description includes instances where said event or circumstance occurs and instances where it does not.

As used herein, the terms "reversible covalent binding motif," "reversible covalent binding warhead," and "reversible covalent binding motif and/or warheads" can be used interchangeably and refer to a peptide comprising a two cysteine moieties, wherein each cysteine moiety is covalently linked to an APBA moiety such that the peptide can bind to a target molecule or target cell, e.g., an microbe or bacteria comprising a target molecule, through a combination of non-covalent interactions involving the peptide backbone and amino acid side-chains and reversible covalent interactions comprising a reversible covalent linkage between one or both of the APBA moieties and a moiety, e.g., an amine group, in the target molecule or target cell. A peptide comprising a reversible covalent binding motif can be within a peptide that is in a phage display library or an isolated peptide, e.g., a therapeutic APBA peptide as discussed herein below.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms. The term alkyl group can also be a C1 alkyl, C1-C2 alkyl, C1-C3 alkyl, C1-C4 alkyl, C1-C5 alkyl, C1-C6 alkyl, C1-C7 alkyl, C1-C8 alkyl, C1-C9 alkyl, C1-C10 alkyl, and the like up to and including a C1-C24 alkyl.

As used herein, the term "APBA," "APBA residue," and "APBA moiety" can be used interchangeably herein and refer to a chemical residue comprising an APBA structure given by the following formula:

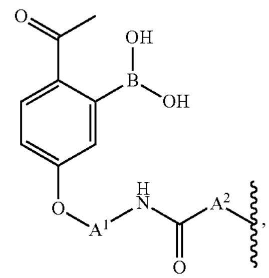

wherein each of $A^1$ and $A^2$ are independently a C1-C6 alkyl. A particular example of an APBA residue is a structure given by the following formula:

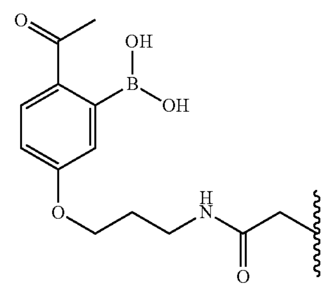

As used herein, the term "APBA-IA" refers to a compound comprising an APBA residue and an iodoacetamide residue having a structure given by the following formula:

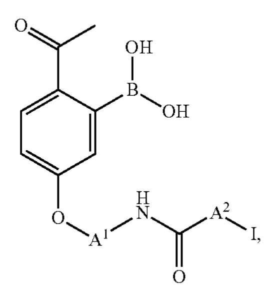

wherein each of $A^1$ and $A^2$ are independently a C1-C6 alkyl. A particular example of APBA-IA is (2-acetyl-5-(3-(2-iodoacetamido)propoxy)phenyl)boronic acid, that is, a compound having a structure given by the following formula:

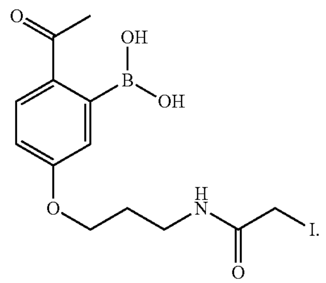 [SMILES: CC(=O)c1ccc(OCCCNC(=O)CI)cc1B(O)O]

The expression "amino acid" as used herein is meant to include both natural and synthetic amino acids, and both D and L amino acids. "Standard amino acid" means any of the twenty standard L-amino acids commonly found in naturally occurring peptides. "Nonstandard amino acid residue" means any amino acid, other than the standard amino acids, regardless of whether it is prepared synthetically or derived from a natural source. As used herein, "synthetic amino acid" also encompasses chemically modified amino acids, including but not limited to salts, amino acid derivatives (such as amides), and substitutions. Amino acids contained within the peptides of the present disclosure, and particularly at the carboxy- or amino-terminus, can be modified by methylation, amidation, acetylation or substitution with other chemical groups which can change the peptide's circulating half-life without adversely affecting their activity. Additionally, a disulfide linkage may be present or absent in the peptides of the invention.

As used herein, the term "APBA modifiable dimer phage library" refers to a phage display library comprising peptides expressed on the surface of the phage display library comprising two cysteine residues that can be chemically modified with an APBA moiety.

As used herein, the term "APBA dimer phage library" refers to a phage display library comprising peptides expressed on the surface of the phage display library comprising two APBA modified cysteine residues.

As used herein, a "therapeutic APBA peptide" is a peptide comprising a peptide sequence as disclosed herein such that the peptide comprises two APBA modified cysteine residues.

As used herein, the term "APBA modified cysteine residue" refers to a cysteine residue comprising an APBA moiety. That is, an APBA modified cysteine residue has a structure given by the formula:

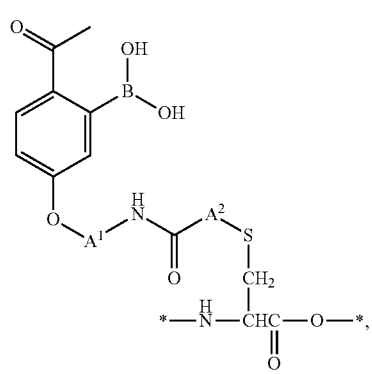

wherein each of $A^1$ and $A^2$ are independently a C1-C6 alkyl. A particular example of an APBA modified cysteine residue can is a structure given by the formula:

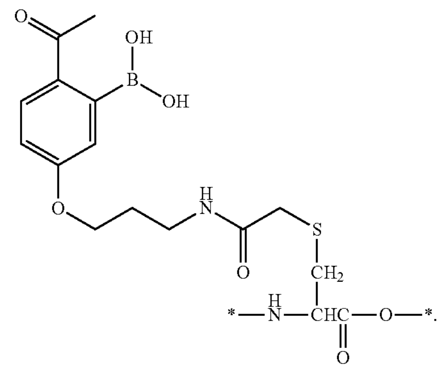

As used herein, the term "APBA modified peptide" is a peptide comprising an APBA modified cysteine residue.

The term "amino acid" is used interchangeably with "amino acid residue," and may refer to a free amino acid and to an amino acid residue of a peptide. It will be apparent from the context in which the term is used whether it refers to a free amino acid or a residue of a peptide.

Amino acids have the following general structure:

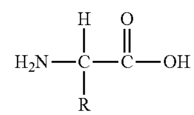

wherein R is a "side chain" or "side group" of the amino acid. Amino acids may be classified into seven groups on the basis of the side chain R: (1) aliphatic side chains, (2) side chains containing a hydroxylic (OH) group, (3) side chains containing sulfur atoms, (4) side chains containing an acidic or amide group, (5) side chains containing a basic group, (6) side chains containing an aromatic ring, and (7) proline, an imino acid in which the side chain is fused to the amino group.

The nomenclature used to describe the peptides or peptide compounds of the present disclosure follows the conventional practice wherein the amino residue is presented to the left and the carboxy group to the right of each amino acid residue. For example, a peptide sequence comprising a sequence of amino acid residues from the amino terminus to the carboxy terminus an alanine residue, an aspartic acid residue, a cysteine residue, and a glycine residue can be specified using the one-letter amino acid code as follows:

ADCG.

In the formula representing selected specific aspects of the present disclosure, e.g., a peptide sequence, the amino- and carboxy-terminal groups, although not specifically shown, will be understood to be in the form they would assume at physiologic pH values, unless otherwise specified. Subscripts in a peptide sequence can be used to indicate a repetition of amino acid, and a subscript range can be used to indicate that the indicated amino acid can be repeated for any of the number of instances of an integer specified by the range, inclusive of the upper and lower limits. For example, a peptide sequence given by:

$ADC(G)_3$, would indicate, from the amino terminus to carboxy terminus, a peptide having an alanine residue, an aspartic acid residue, a cysteine residue, and three sequential iterations of a glycine residue. A peptide sequence can also be specified with variable positions using Xxx (three-letter code) or X (one-letter). For example, a peptide sequence comprising a sequence of amino acid residues from the amino terminus to the carboxy terminus an alanine residue, an aspartic acid residue, one to five amino acids selected from the standard amino acids, a cysteine residue, and a glycine residue can be specified using the one-letter amino acid code as follows:

$ADC(X)_{1-5}G$.

As used herein, an "analog" of a chemical compound is a compound that, by way of example, resembles another in structure but is not necessarily an isomer (e.g., 5-fluorouracil is an analog of thymine).

As used herein, an amino acid can be represented by the full name thereof, by the three-letter code corresponding thereto, or by the one-letter code corresponding thereto. The full name, three-letter code, and one-letter code for 20 standard amino acids are as indicated in the table below.

| Full Name | Three-Letter Code | One-Letter Code | Side Chain (R) |
|---|---|---|---|
| Aspartic Acid | Asp | D | 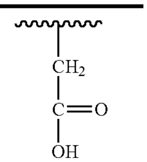 |
| Glutamic Acid | Glu | E | 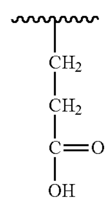 [SMILES: *CCC(=O)O] |
| Lysine | Lys | K | 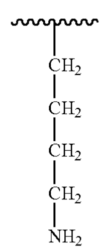 |
| Arginine | Arg | R | 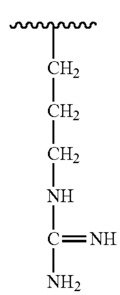 |

-continued

| Full Name | Three-Letter Code | One-Letter Code | Side Chain (R) |
|---|---|---|---|
| Histidine | His | H | 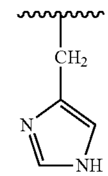 [SMILES: *Cc1c[nH]cn1] |
| Tyrosine | Tyr | Y | 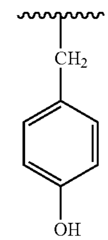 [SMILES: *Cc1ccc(O)cc1] |
| Cysteine | Cys | C | 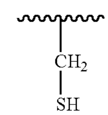 |
| Asparagine | Asn | N | 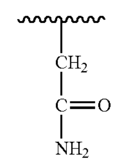 |
| Glutamine | Gln | Q | 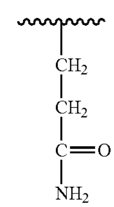 |
| Serine | Ser | S | 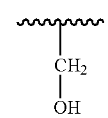 |
| Threonine | Thr | T | 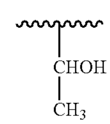 |
| Glycine | Gly | G | 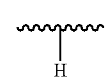 |
| Alanine | Ala | A | 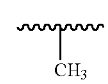 |

-continued

| Full Name | Three-Letter Code | One-Letter Code | Side Chain (R) |
|---|---|---|---|
| Valine | Val | V | 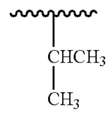 |
| Leucine | Leu | L | 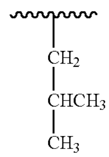 |
| Isoleucine | Ile | I | 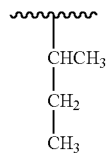 |
| Methionine | Met | M | 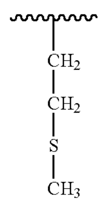 |
| Proline | Pro | P | 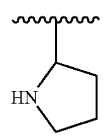 |
| Phenylalanine | Phe | F | 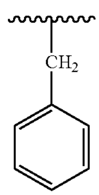 [SMILES: *Cc1ccccc1] |
| Tryptophan | Trp | W | 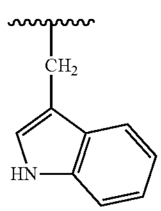 [SMILES: *Cc1c[nH]c2ccccc12] |

The term "basic" or "positively charged" amino acid as used herein, refers to amino acids in which the R groups have a net positive charge at pH 7.0, and include, but are not limited to, the standard amino acids lysine, arginine, and histidine.

A "compound," as used herein, refers to a polypeptide, an isolated nucleic acid, or other agent used in the method of the present disclosure.

As used herein, the terms "polypeptide", "peptide", or "protein" refer to a series of amino acid residues connected one to the other by peptide bonds between the alpha-amino and carboxy groups of adjacent residues. The amino acid residues are preferably in the natural "L" isomeric form. However, residues in the "D" isomeric form can be substituted for any L-amino acid residue, as long as the desired functional property is retained by the polypeptide. In addition, the amino acids, in addition to the 20 standard amino acids, include modified and unusual amino acids. Furthermore, it should be noted that a dash at the beginning or end of an amino acid residue sequence indicates either a peptide bond to a further sequence of one or more amino acid residues or a covalent bond to a carboxyl or hydroxyl end group.

As used herein, the term "APBA modified peptide" refers to a peptide comprising two cysteine residue comprising an APBA moiety having the structure and sequences as disclosed herein.

As used herein, the term "target cell" refers to a cell or cell-type that is to be specifically bound by a member of a phage display library of the present disclosure. Target cells can be antibiotic resistant bacterial pathogens, e.g., *Staphylococcus aureus* or colistin-resistant strains of *Acinetobacter baumannii*, for which a binding peptide is sought. The target cell is typically characterized by the expression a target molecule that is characteristic of the cell type, i.e., characteristic of the target cell in that it is uniquely expressed on the target cell compared to a non-target cell or a target molecule that is overexpressed on the target cell compared to a non-target cell. Thus, for example, a target cell can be a cell, such as a *Staphylococcus aureus* or colistin-resistant strains of *Acinetobacter baumannii*, which expresses a target molecule, such as a protein or carbohydrate that can be bound by a phage display library. As noted above, a target molecule may be unique to the target cell compared to other cells or may be a molecule which is overexpressed by the target cell compared to other cells.

As used herein, "phage display" refers to a method of using phage to heterologously express coat proteins or peptides for testing, e.g., particularly newly generated peptides (e.g., from about 5 to about 10 amino acids in length) thereof. A gene encoding a protein or peptide is cloned and inserted into a phage genome or genetic material in such a way that the protein or peptide is displayed (i.e., expressed) on the surf ace of the phage, which is a recombinant phage. Phage expressing peptides that interact with a target molecule or cell can be selected by selecting the protein or peptide directly using panning or affinity chromatography. The non-bound phages can be removed by washing the cells expressing the target molecule. The bound proteins or peptides produced by phages can then be isolated from the target molecule or target cell to which they are bound, and since they are still part of the phage, they can be grown in enough quantity to identify the gene sequence, and hence the protein sequence. This allows further manipulation of phages that bind to the target molecule(s).

As used herein, the term "phage display library" refers to a collection of phage (e.g., filamentous phage) comprising collection of random sequences of nucleic acids that have been inserted into a phage vector, wherein the phage express a heterologous peptide encoded by the random sequences of nucleic acids therein on the surface of a phage particle. The library can contain a few or a large number of random combinations of nucleic acid sequences, varying from about ten to several billion combinations of nucleotide sequences or more that code for a vast number ($\sim 10^{12}$) of random peptides. The external peptide is free to interact with (bind to) other moieties with which the phage are contacted. Each phage displaying an external protein is a "member" of the phage display library. If desired, a molecule or a phage vector can be linked to a tag, which can facilitate recovery or identification of the molecule. In some instances, the heterologously expressed proteins or peptides that are on the surface of a phage particle can be chemically modified to expand the chemical space encompassed by the phage display library, e.g., such a chemically modified phage display library is the disclosed APBA dimer phage library.

As used herein, the term "phage" refers to a bacteriophage or virus that infects bacteria and is capable of displaying a heterologous polypeptide or peptide on its surface. Briefly, a phage comprises a protein coat or capsid enclosing the phage genome or genetic material (DNA or RNA) which is injected into a bacteria upon infection of the bacteria by the phage. The injected genetic material directs the bacteria to synthesize the phage's genetic material and proteins encoded by the phage genetic material using the host bacteria's transcriptional and translational apparatus. These phage components then self-assemble to form new phage viruses or particles. Although one skilled in the art will appreciate that a variety of phage types may be employed in the present invention, in some instances the phage vector is, or is derived from, a filamentous bacteriophage, such as, for example, fl, fd, Pf1, M13, etc. The phage may contain a selectable marker such as tetracycline (e.g., "fd-tet"). Various filamentous phage display systems are well known to those of skill in the art (see, e.g., Zacher et al. (1980) Gene 9: 127-140, Smith et al. (1985) Science 228: 1315-1317 (1985); and Parmley and Smith (1988) Gene 73: 305-318).

As used herein, the term "phage vector" is a bacterial virus which can receive the insertion of a gene or other genetic material, resulting in a recombinant DNA molecule. The phage vector is capable of self-replication in a host organism. A phage vector contains an origin of replication for a bacteriophage but not for a plasmid.

As used herein, the term "viral packaging signal" refers a nucleic acid sequence necessary and sufficient to direct incorporation of a nucleic acid into a viral capsid.

As used herein, the term "assembly cell" refers to a cell in which a nucleic acid can be packaged into a viral coat protein (capsid). Assembly cells may be infected with one or more different virus particles (e.g. a normal or debilitated phage and a helper phage) that individually or in combination direct packaging of a nucleic acid into a viral capsid.

As used herein, the term "detectable label" refers to any material having a detectable physical or chemical property. Such detectable labels have been well-developed in the field of immunoassays and, in general, any label useful in such methods can be applied to the present invention. Thus, a label is any composition detectable by spectroscopic, photochemical, biochemical, immunochemical, electrical, optical or chemical means. Useful labels in the present invention include magnetic beads (e.g. Dynabeads™), fluorescent dyes (e.g., fluorescein isothiocyanate, Texas red, rhodamine, and the like), radiolabels (e.g., 3H, 125I, 35S, 14C, or 32P), enzymes (e.g., LacZ, CAT, horse radish peroxidase, alkaline phosphatase and others, commonly used as detectable enzymes, either as marker gene products or in an ELISA), and calorimetric labels such as colloidal gold or colored glass or plastic (e.g. polystyrene, polypropylene, latex, etc.) beads. Those detectable labels that can be expressed by nucleic acids are referred to as "reporter genes" or "reporter gene products".

It will be recognized that fluorescent labels are not to be limited to single species organic molecules, but include inorganic molecules, multi-molecular mixtures of organic and/or inorganic molecules, crystals, heteropolymers, and the like. Thus, for example, CdSe—CdS core-shell nanocrystals enclosed in a silica shell can be easily derivatized for coupling to a biological molecule (Bruchez et al. (1998) Science, 281: 2013-2016). Similarly, highly fluorescent quantum dots (zinc sulfide-capped cadmium selenide) have been covalently coupled to biomolecules for use in ultrasensitive biological detection (Warren and Nie (1998) Science, 281: 2016-2018).

A residue of a chemical species as herein refers to the moiety that is the resulting product of the chemical species in a particular reaction scheme or subsequent formulation or chemical product, regardless of whether the moiety is actually obtained from the chemical species. In general chemical terms, an example of a residue can be an ethylene glycol residue in a polyester refers to one or more $—OCH_2CH_2O—$ units in the polyester, regardless of whether ethylene glycol was used to prepare the polyester. Similarly, a sebacic acid residue in a polyester refers to one or more $—CO(CH_2)_8CO—$ moieties in the polyester, regardless of whether the residue is obtained by reacting sebacic acid or an ester thereof to obtain the polyester. Thus, in particular terms with regard to amino acid residues, it would be understood that an alanine residue in a polypeptide or peptide refers to the presence of a residue having a structure given by the formula:

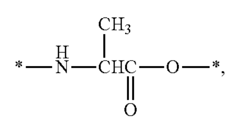

regardless of whether alanine was used to prepare the polypeptide or peptide.

Compounds described herein comprise atoms in both their natural isotopic abundance and in non-natural abundance. The disclosed compounds can be isotopically-labeled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, sulfur, fluorine and chlorine, such as $^{2}H$, $^{3}H$, $^{13}C$, $^{14}C$, $^{15}N$, $^{18}O$, $^{17}O$, $^{35}S$, $^{18}F$, and $^{36}Cl$, respectively. Compounds further comprise prodrugs thereof and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvent or water molecules can combine with the compounds according to the invention to form solvates and hydrates. Unless stated to the contrary, the invention includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et al., The Royal Society of Chemistry, 1889-1896, 2004. Examples of co-crystals include p-toluenesulfonic acid and benzenesulfonic acid.

As used herein, "administering" can refer to an administration that is oral, topical, intravenous, subcutaneous, transcutaneous, transdermal, intramuscular, intra joint, parenteral, intra-arteriole, intradermal, intraventricular, intraosseous, intraocular, intracranial, intraperitoneal, intralesional, intranasal, intracardiac, intraarticular, intracavernous, intrathecal, intravireal, intracerebral, and intracerebroventricular, intratympanic, intracochlear, rectal, vaginal, by inhalation, by catheters, stents or via an implanted reservoir or other device that administers, either actively or passively (e.g. by diffusion) a composition the perivascular space and adventitia. For example a medical device such as a stent can contain a composition or formulation disposed on its surface, which can then dissolve or be otherwise distributed to the surrounding tissue and cells. The term "parenteral" can include subcutaneous, intravenous, intramuscular, intra-articular, intra-synovial, intrasternal, intrathecal, intrahepatic, intralesional, and intracranial injections or infusion techniques. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, "therapeutic agent" can refer to any substance, compound, molecule, and the like, which can be biologically active or otherwise can induce a pharmacologic, immunogenic, biologic and/or physiologic effect on a subject to which it is administered to by local and/or systemic action. A therapeutic agent can be a primary active agent, or in other words, the component(s) of a composition to which the whole or part of the effect of the composition is attributed. A therapeutic agent can be a secondary therapeutic agent, or in other words, the component(s) of a composition to which an additional part and/or other effect of the composition is attributed. The term therefore encompasses those compounds or chemicals traditionally regarded as drugs, vaccines, and biopharmaceuticals including molecules such as proteins, peptides, hormones, nucleic acids, gene constructs and the like. Examples of therapeutic agents are described in well-known literature references such as the Merck Index (14th edition), the Physicians' Desk Reference (64th edition), and The Pharmacological Basis of Therapeutics (12th edition), and they include, without limitation, medicaments; vitamins; mineral supplements; substances used for the treatment, prevention, diagnosis, cure or mitigation of a disease or illness; substances that affect the structure or function of the body, or pro-drugs, which become biologically active or more active after they have been placed in a physiological environment. For example, the term "therapeutic agent" includes compounds or compositions for use in all of the major therapeutic areas including, but not limited to, adjuvants; anti-infectives such as antibiotics and antiviral agents; analgesics and analgesic combinations, anorexics, anti-inflammatory agents, anti-epileptics, local and general anesthetics, hypnotics, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics, antiarrhythmics, antihypertensive agents, hormones, and nutrients, antiarthritics, antiasthmatic agents, anticonvulsants, antihistamines, antinauseants, antineoplastics, antipruritics, antipyretics; antispasmodics, cardiovascular preparations (including calcium channel blockers, beta-blockers, beta-agonists and antiarrythmics), antihypertensives, diuretics, vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like), small molecules (e.g., doxorubicin) and other biologically active macromolecules such as, for example, proteins and enzymes. The agent may be a biologically active agent used in medical, including veterinary, applications and in agriculture, such as with plants, as well as other areas. The term therapeutic agent also includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

As used herein, "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

As used herein, "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form which may be supplied on computer readable memory device or downloaded from an internet website, or as recorded presentation. Instructions can comprise one or multiple documents, and are meant to include future updates.

As used herein, "attached" can refer to covalent or non-covalent interaction between two or more molecules. Non-covalent interactions can include ionic bonds, electrostatic interactions, van der Walls forces, dipole-dipole interactions, dipole-induced-dipole interactions, London dispersion forces, hydrogen bonding, halogen bonding, electromagnetic interactions, π-π interactions, cation-π interactions, anion-π interactions, polar π-interactions, and hydrophobic effects.

As used interchangeably herein, "subject," "individual," or "patient" can refer to a vertebrate organism, such as a mammal (e.g. human). "Subject" can also refer to a cell, a population of cells, a tissue, an organ, or an organism, preferably to human and constituents thereof.

As used herein, the terms "treating" and "treatment" can refer generally to obtaining a desired pharmacological and/or physiological effect. The effect can be, but does not necessarily have to be, prophylactic in terms of preventing or partially preventing a disease, symptom or condition thereof, such as a microbial infection or a microbial infection involving an antibiotic resistant microbe, e.g., antibiotic resistant *Staphylococcus aureus* and/or colistin-resistant strains of *Acinetobacter baumannii*. The effect can be therapeutic in terms of a partial or complete cure of a disease, condition, symptom or adverse effect attributed to the disease, disorder, or condition. The term "treatment" as used herein can include any treatment of a microbial infection in a subject, particularly a human and can include any one or more of the following: (a) preventing the disease from occurring in a subject which may be predisposed to the disease but has not yet been diagnosed as having it; (b) inhibiting the disease, i.e., arresting its development; and (c) relieving the disease, i.e., mitigating or ameliorating the disease and/or its symptoms or conditions. The term "treatment" as used herein can refer to both therapeutic treatment alone, prophylactic treatment alone, or both therapeutic and prophylactic treatment. Those in need of treatment (subjects in need thereof) can include those already with the disorder and/or those in which the disorder is to be prevented. As used herein, the term "treating", can include inhibiting the disease, disorder or condition, e.g., impeding its progress; and relieving the disease, disorder, or condition, e.g., causing regression of the disease, disorder and/or condition. Treating the disease, disorder, or condition can include ameliorating at least one symptom of the particular disease, disorder, or condition, even if the underlying pathophysiology is not affected, e.g., such as treating the pain of a subject by administration of an analgesic agent even though such agent does not treat the cause of the pain.

As used herein, "dose," "unit dose," or "dosage" can refer to physically discrete units suitable for use in a subject, each unit containing a predetermined quantity of a disclosed compound and/or a pharmaceutical composition thereof calculated to produce the desired response or responses in association with its administration.

As used herein, "therapeutic" can refer to treating, healing, and/or ameliorating a disease, disorder, condition, or side effect, or to decreasing in the rate of advancement of a disease, disorder, condition, or side effect.

As used herein, "effective amount" can refer to the amount of a disclosed compound or pharmaceutical composition provided herein that is sufficient to effect beneficial or desired biological, emotional, medical, or clinical response of a cell, tissue, system, animal, or human. An effective amount can be administered in one or more administrations, applications, or dosages. The term can also include within its scope amounts effective to enhance or restore to substantially normal physiological function.

As used herein, the term "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors within the knowledge and expertise of the health practitioner and which may be well known in the medical arts. In the case of treating a particular disease or condition, in some instances, the desired response can be inhibiting the progression of the disease or condition. This may involve only slowing the progression of the disease temporarily. However, in other instances, it may be desirable to halt the progression of the disease permanently. This can be monitored by routine diagnostic methods known to one of ordinary skill in the art for any particular disease. The desired response to treatment of the disease or condition also can be delaying the onset or even preventing the onset of the disease or condition.

For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. It is generally preferred that a maximum dose of the pharmacological agents of the invention (alone or in combination with other therapeutic agents) be used, that is, the highest safe dose according to sound medical judgment. It will be understood by those of ordinary skill in the art however, that a patient may insist upon a lower dose or tolerable dose for medical reasons, psychological reasons or for virtually any other reasons.

A response to a therapeutically effective dose of a disclosed compound and/or pharmaceutical composition, for example, can be measured by determining the physiological effects of the treatment or medication, such as the decrease or lack of disease symptoms following administration of the treatment or pharmacological agent. Other assays will be known to one of ordinary skill in the art and can be employed for measuring the level of the response. The amount of a treatment may be varied for example by increasing or decreasing the amount of a disclosed compound and/or pharmaceutical composition, by changing the disclosed compound and/or pharmaceutical composition administered, by changing the route of administration, by changing the dosage timing and so on. Dosage can vary, and can be administered in one or more dose administrations daily, for one or several days. Guidance can be found in the literature for appropriate dosages for given classes of pharmaceutical products.

As used herein, the term "prophylactically effective amount" refers to an amount effective for preventing onset or initiation of a disease or condition.

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

The term "pharmaceutically acceptable" describes a material that is not biologically or otherwise undesirable, i.e., without causing an unacceptable level of undesirable biological effects or interacting in a deleterious manner.

The term "pharmaceutically acceptable salts", as used herein, means salts of the active principal agents which are prepared with acids or bases that are tolerated by a biological system or tolerated by a subject or tolerated by a biological system and tolerated by a subject when administered in a therapeutically effective amount. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include, but are not limited to; sodium, potassium, calcium, ammonium, organic amino, magnesium salt, lithium salt, strontium salt or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include, but are not limited to; those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like.

The term "pharmaceutically acceptable ester" refers to esters of compounds of the present disclosure which hydrolyze in vivo and include those that break down readily in the human body to leave the parent compound or a salt thereof. Examples of pharmaceutically acceptable, non-toxic esters of the present disclosure include C 1-to-C 6 alkyl esters and C 5-to-C 7 cycloalkyl esters, although C 1-to-C 4 alkyl esters are preferred. Esters of disclosed compounds can be prepared according to conventional methods. Pharmaceutically acceptable esters can be appended onto hydroxy groups by reaction of the compound that contains the hydroxy group with acid and an alkylcarboxylic acid such as acetic acid, or with acid and an arylcarboxylic acid such as benzoic acid. In the case of compounds containing carboxylic acid groups, the pharmaceutically acceptable esters are prepared from compounds containing the carboxylic acid groups by reaction of the compound with base such as triethylamine and an alkyl halide, for example with methyl iodide, benzyl iodide, cyclopentyl iodide or alkyl triflate. They also can be prepared by reaction of the compound with an acid such as hydrochloric acid and an alcohol such as ethanol or methanol.

The term "pharmaceutically acceptable amide" refers to non-toxic amides of the present disclosure derived from ammonia, primary C 1-to-C 6 alkyl amines and secondary C 1-to-C 6 dialkyl amines. In the case of secondary amines, the amine can also be in the form of a 5- or 6-membered heterocycle containing one nitrogen atom. Amides derived from ammonia, C 1-to-C 3 alkyl primary amides and C 1-to-C 2 dialkyl secondary amides are preferred. Amides of disclosed compounds can be prepared according to conventional methods. Pharmaceutically acceptable amides can be prepared from compounds containing primary or secondary amine groups by reaction of the compound that contains the amino group with an alkyl anhydride, aryl anhydride, acyl halide, or aroyl halide. In the case of compounds containing carboxylic acid groups, the pharmaceutically acceptable amides are prepared from compounds containing the carboxylic acid groups by reaction of the compound with base such as triethylamine, a dehydrating agent such as dicyclohexyl carbodiimide or carbonyl diimidazole, and an alkyl amine, dialkylamine, for example with methylamine, diethylamine, and piperidine. They also can be prepared by reaction of the compound with an acid such as sulfuric acid and an alkylcarboxylic acid such as acetic acid, or with acid and an arylcarboxylic acid such as benzoic acid under dehydrating conditions such as with molecular sieves added. The composition can contain a compound of the present disclosure in the form of a pharmaceutically acceptable prodrug.

The term "pharmaceutically acceptable prodrug" or "prodrug" represents those prodrugs of the compounds of the present disclosure which are, within the scope of sound medical judgment, suitable for use in contact with the tissues of humans and lower animals without undue toxicity, irritation, allergic response, and the like, commensurate with a reasonable benefit/risk ratio, and effective for their intended use. Prodrugs of the present disclosure can be rapidly transformed in vivo to a parent compound having a structure of a disclosed compound, for example, by hydrolysis in blood. A thorough discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987).

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, and amides, salts of esters or amides, and N-oxides of a parent compound.

The term "contacting" as used herein refers to bringing a disclosed compound or pharmaceutical composition in proximity to a cell, a target protein, or other biological entity together in such a manner that the disclosed compound or pharmaceutical composition can affect the activity of the a cell, target protein, or other biological entity, either directly; i.e., by interacting with the cell, target protein, or other biological entity itself, or indirectly; i.e., by interacting with another molecule, co-factor, factor, or protein on which the activity of the cell, target protein, or other biological entity itself is dependent.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

It is understood, that unless otherwise specified, temperatures referred to herein are based on atmospheric pressure (i.e. one atmosphere).

Chemically Modified Phage Libraries

Several earlier reports described phage panning against intact bacterial cells, which, however, only yielded bacterial binders of sub to low millimolar affinity. Despite the low affinity binding of the peptide hits, the corresponding intact phage particles showed promise as delivery vehicles of antibiotics, presumably due to the pentavalent display of the peptide binder. For comparison, screening of the APBA dimer library herein yielded bacterial binders of sub-micromolar potency. The contrasting results highlight the promise of chemically modified phage libraries. Even higher potency binding could be accomplished with better designed phage libraries with reversible covalent warheads.

The phage panning against intact cells is remarkably convenient and powerful, allowing facile incorporation of negative screens and internal competitors. Specifically, as previously reported, abundant endogenous protein could compete for iminoboronate conjugation, thereby inhibiting the bacterial binding of an APBA-containing peptide. The data presented in the present disclosure unequivocally show that this protein interference problem can be overcome by including serum albumin in the screening mixture and the reversible covalent binding mechanism can afford highly selective binders in complex biological milieu.

The APBA dimer library can be extended to discovering binders of various bacterial pathogens. This is feasible given that iminoboronate chemistry is generally applicable to primary amines, which can be abundant on bacterial cells particularly those showing antibiotic resistance. Amino acid modification of phospholipids, such as Lys-PG synthesis in *S. aureus*, have been documented for a number of bacterial species as a resistance mechanism to host defense peptides and neutrophil clearance. Such lipid modification affords a high abundance of amino groups (α- and ε-amine of lysine) on a bacterial surface. Similarly, alanylation of teichoic acids results in abundant alanyl ester structures with α-amines available for iminoboronate conjugation. Surface modification of gram-negative bacteria is becoming better understood as well. It has been shown that lipopolysaccharide (LPS) or lipooligosaccharide (LOS) modification with phosphoethanolamine and/or 4-aminoarabanose leads to polymyxin resistance for many bacterial species. These surface modified bacterial strains would be particularly amenable to specific recognition by the iminoboronate-capable peptides.

The present disclosure provides that a bacterial binder identified from phage display can be readily converted to targeted antibiotics that specifically eradicate the corresponding strain of bacteria. The facile generation of targeted antibiotics is of contemporary importance given the undesirable consequences of broad-spectrum antibiotics, which inevitably cultivate antibiotic resistance and cause damage to human microbiota. Although the present disclosure utilizes a phototoxin as the bactericidal agent, it is conceivable that antibiotics of other modes of action, such as those targeting cell membranes including vancomycin and daptomycin, can be utilized to build peptide-antibiotic conjugates, which will expand the scope of our strategy to create targeted antibiotics.

The phage display platform can be further developed to include additional phage libraries with reversible covalent warheads. This can be accomplished by varying the designs of the reversible covalent warheads and introducing cross-links to the linear peptide architecture to generate cyclic and multicyclic peptides. Additional phage libraries as such can maximize the chance of success for a diverse range of bacterial pathogens. The design principles of peptide-antibiotic conjugates that can be used for the selective clearance of a pathogenic bacteria can also be systematically studies.

The disclosed phage display libraries comprise an APBA residue. In various aspects, the disclosed phage display libraries comprise two APBA modified cysteine residues in a peptide expressed on a phage particle surface. As discussed herein above, an APBA residue has a structure given by the following formula:

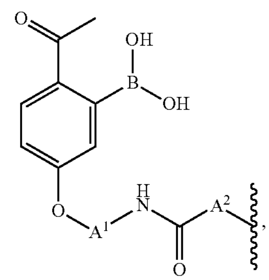

wherein each of $A^1$ and $A^2$ are independently a C1-C6 alkyl. A particular example of an APBA residue is a structure given by the following formula:

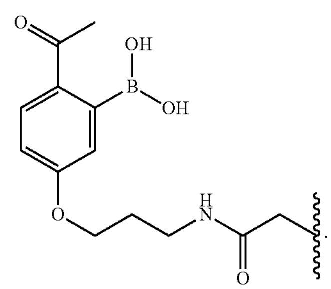 [SMILES: *CC(=O)NCCCOc1ccc(C(C)=O)c(B(O)O)c1]

Accordingly, a disclosed phage display library comprises peptide structures on an external surface of a phage particle comprising two cysteine residues having an APBA residue as shown herein above.

In various aspects, a disclosed phage display library comprises an APBA modified peptide, i.e., peptides expressed on an external surface of a phage particle such that the peptides comprise an APBA modified cysteine residue, as discussed above, In various aspects, a disclosed phage display library can be prepared by chemically modifying an APBA modifiable phage display library, e.g., using an APBA-IA reagent. Specific examples of preparation of a disclosed phage display library using an APBA-IA are provided herein below in the Examples. As defined above, an APBA-IA reagent is a compound comprising an APBA moiety and an iodoacetamide residue having a structure given by the following formula:

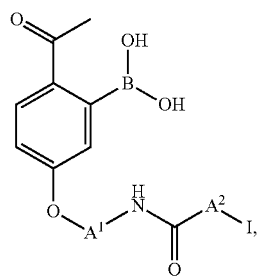

wherein each of $A^1$ and $A^2$ are independently a C1-C6 alkyl. A particular example of APBA-IA is (2-acetyl-5-(3-(2-iodoacetamido)propoxy)phenyl)boronic acid, that is, a compound having a structure given by the following formula:

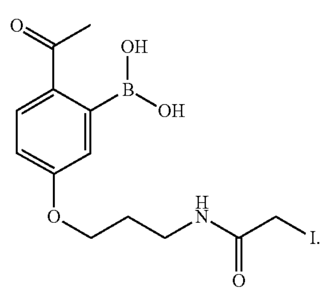 [SMILES: CC(=O)c1ccc(OCCCNC(=O)CI)cc1B(O)O]

In various aspects, a disclosed APBA modifiable dimer phage library is a phage display library comprising a peptide sequence on an external portion of a phage particle as follows:

$$XC(X)_nC(X)_m,$$

wherein each instance of X is an amino acid independently selected from D, E, K, R, H, Y, N, Q, S, T, G, A, V, L, I, M, P, F, and W; wherein n is an integer selected from 5, 6, 7, 8, 9, and 10; and wherein m is an integer selected from 1, 2, 3, 4, and 5. As disclosed herein, a disclosed APBA modifiable dimer phage library comprises APBA modifiable peptides on the surface of a phage particle have the structure given by the following formula:

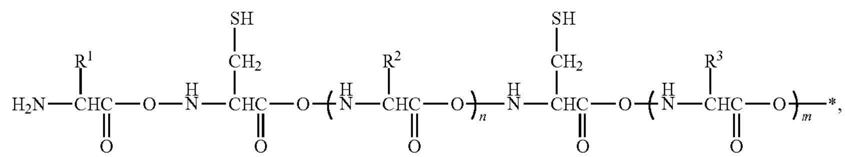

wherein each occurrence of $R^1$, $R^2$, and $R^3$ are independently selected from a moiety that is an amino acid side chain except a cysteine side chain; wherein n is an integer selected from 5, 6, 7, 8, 9, and 10; and wherein m is an integer selected from 1, 2, 3, 4, and 5.

In a particular instance, an APBA modifiable dimer phage library is a phage display library comprising a peptide sequence on an external portion of a phage particle as follows:

$$AC(X)_nC(G)_m,$$

In a particular instance, an APBA modifiable dimer phage library comprises APBA modifiable peptides on the surface of a phage particle have the structure given by the following formula:

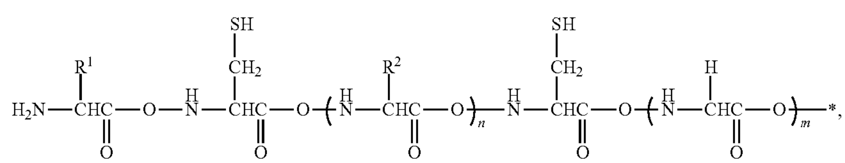

wherein each occurrence of $R^2$ is independently selected from a moiety that is an amino acid side chain except cysteine; wherein n is an integer selected from 5, 6, 7, 8, 9, and 10; and wherein m is an integer selected from 1, 2, 3, 4, and 5.

In various aspects, a disclosed phage display library is an APBA dimer phage library. A exemplary phage display library comprises peptide sequences on an external portion of a phage particle as follows:

$$XC^*(X)_nC^*(X)_m,$$

wherein C* indicates a cysteine residue modified to comprise an APBA residue; wherein each instance of X is an amino acid independently selected from D, E, K, R, H, Y, N, Q, S, T, G, A, V, L, I, M, P, F, and W; wherein n is an integer selected from 5, 6, 7, 8, 9, and 10; wherein m is an integer selected from 1, 2, 3, 4, and 5.

In a further aspect, a disclosed APBA dimer phage library comprises APBA modified peptides on the surface of a phage particle having a structure given by the following formula:

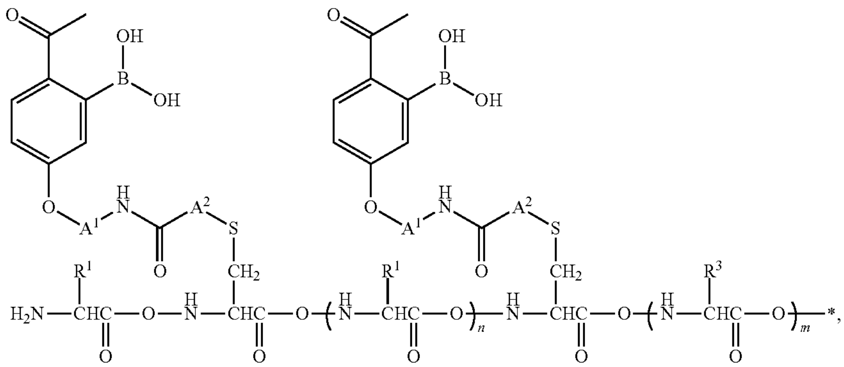

wherein each of $A^1$ and $A^2$ are independently a C1-C6 alkyl; wherein each occurrence of R', $R^2$, and $R^3$ are independently selected from a moiety that is an amino acid side chain except cysteine; wherein n is an integer selected from 5, 6, 7, 8, 9, and 10; and wherein m is an integer selected from 1, 2, 3, 4, and 5.

In a further aspect, an APBA dimer phage library comprises modified peptides on the surface of a phage particle having a structure given by the following formula:

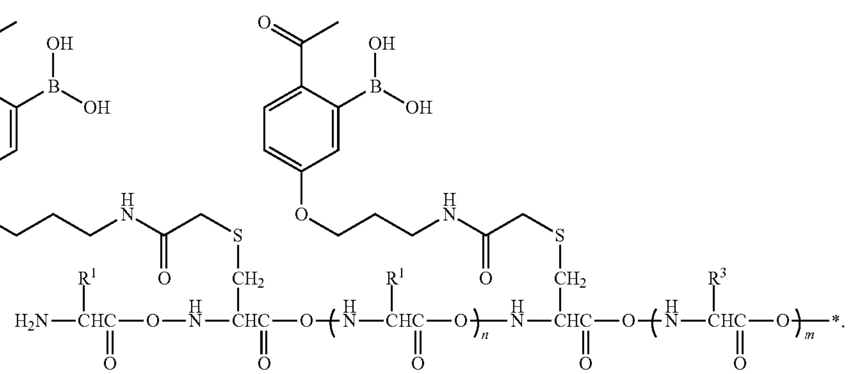

In various aspects, a disclosed APBA dimer phage library is a phage display library comprising peptide sequence on an external portion of a phage particle as follows:

$AC^*(X)_nC^*(G)_m$,

In various aspects, an APBA dimer phage library comprises APBA modified peptides on the surface of a phage particle having a structure given by the following formula:

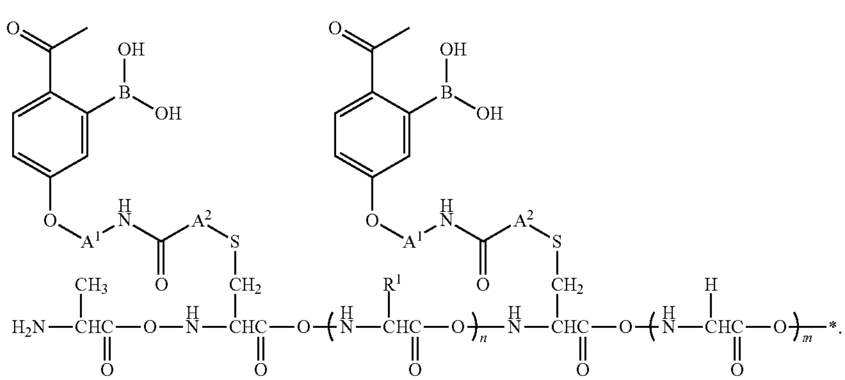

In a further aspect, an APBA dimer phage library comprises APBA modified peptides on the surface of a phage particle having a structure given by the following formula:

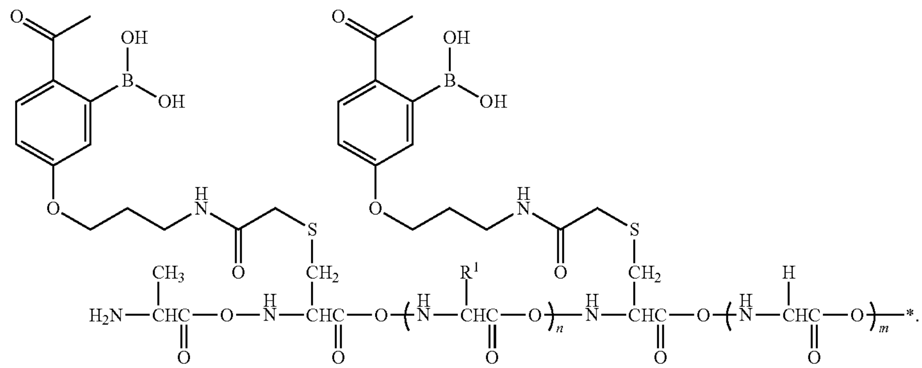

Therapeutic APBA Peptides

In various aspects, the present disclosure pertains to therapeutic APBA peptides. That is, APBA modified peptides which are understood to be peptides comprising two APBA modified cysteine residues. An exemplary disclosed therapeutic APBA peptide is a peptide sequence as follows:

$XC^*(X)_nC^*(X)_m$, wherein C* indicates a cysteine residue modified to comprise an APBA residue; wherein each instance of X is an amino acid independently selected from D, E, K, R, H, Y, N, Q, S, T, G, A, V, L, I, M, P, F, and W; wherein n is an integer selected from 5, 6, 7, 8, 9, and 10; wherein m is an integer selected from 1, 2, 3, 4, and 5.

In various aspects, a disclosed therapeutic APBA peptide is a peptide having a structure given by the formula:

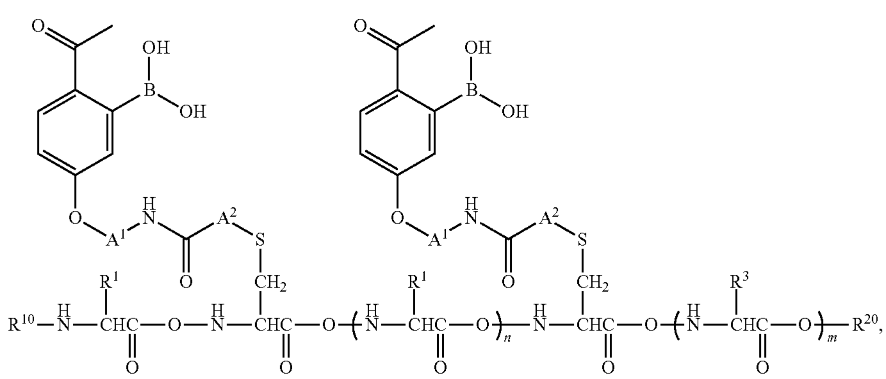

wherein each of $A^1$ and $A^2$ are independently a C1-C6 alkyl; wherein each occurrence of R', $R^2$, and $R^3$ are independently selected from a side chain of an amino acid selected from D, E, K, R, H, Y, N, Q, S, T, G, A, V, L, I, M, P, F, and W; wherein each of $R^{10}$ and $R^{20}$ is selected from hydrogen, an antibiotic residue, a phototoxin residue, and a detectable label residue; wherein n is an integer selected from 5, 6, 7, 8, 9, and 10; and wherein m is an integer selected from 1, 2, 3, 4, and 5.

In a further aspect, a disclosed therapeutic APBA peptide is a peptide having a structure given by the formula:

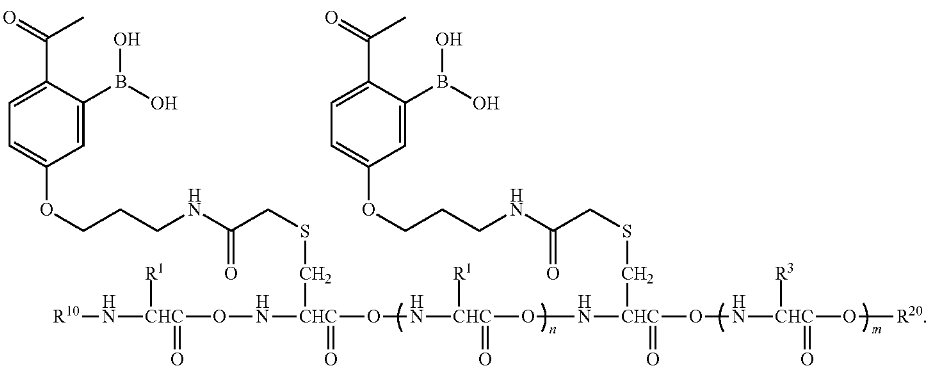

In a further aspect, a disclosed therapeutic APBA peptide is a peptide having a structure given by the formula:

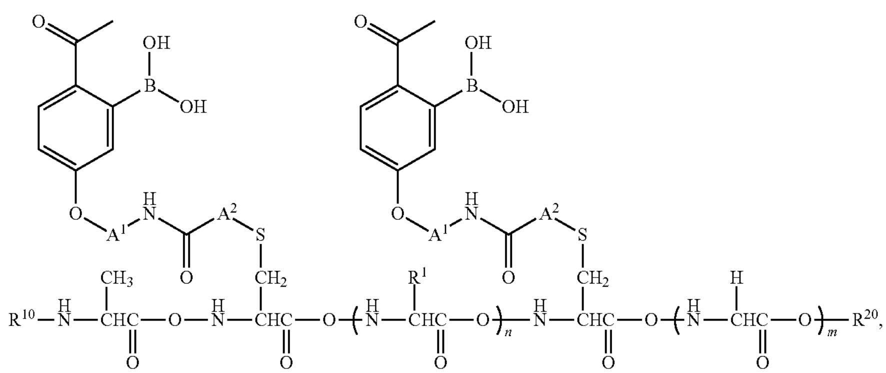

In a further aspect, a disclosed therapeutic APBA peptide is a peptide having a structure given by the formula:

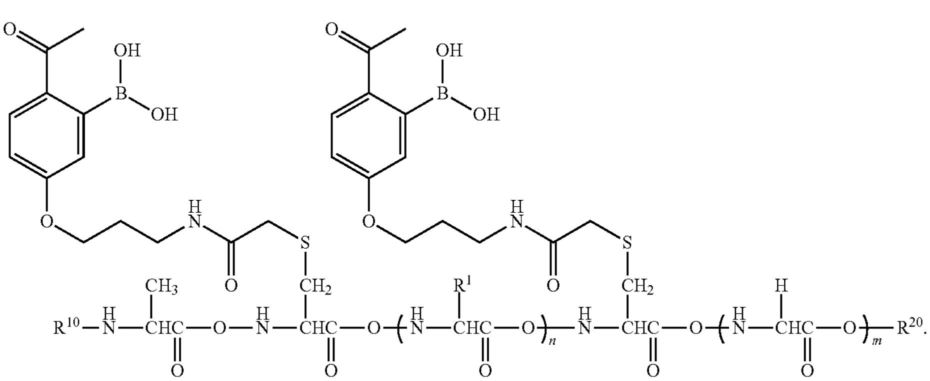

Pharmaceutical Compositions

In various aspects, the present disclosure relates to pharmaceutical compositions comprising a therapeutically effective amount of at least one therapeutic APBA peptide, or a pharmaceutically acceptable salt thereof. As used herein, "pharmaceutically-acceptable carriers" means one or more of a pharmaceutically acceptable diluents, preservatives, antioxidants, solubilizers, emulsifiers, coloring agents, releasing agents, coating agents, sweetening, flavoring and perfuming agents, and adjuvants. The disclosed pharmaceutical compositions can be conveniently presented in unit dosage form and prepared by any of the methods well known in the art of pharmacy and pharmaceutical sciences.

In a further aspect, the disclosed pharmaceutical compositions comprise a therapeutically effective amount of at least one disclosed therapeutic APBA peptide, optionally one or more other therapeutic agent, and optionally one or more adjuvant. The disclosed pharmaceutical compositions include those suitable for oral, rectal, topical, pulmonary, nasal, and parenteral administration, although the most suitable route in any given case will depend on the particular host, and nature and severity of the conditions for which the active ingredient is being administered. In a further aspect, the disclosed pharmaceutical composition can be formulated to allow administration orally, nasally, via inhalation, parenterally, paracancerally, transmucosally, transdermally, intramuscularly, intravenously, intradermally, subcutaneously, intraperitonealy, intraventricularly, intracranially and intratumorally.

As used herein, "parenteral administration" includes administration by bolus injection or infusion, as well as administration by intravenous, intramuscular, intraarterial, intrathecal, intracapsular, intraorbital, intracardiac, intradermal, intraperitoneal, transtracheal, subcutaneous, subcuticular, intraarticular, subcapsular subarachnoid, intraspinal, epidural and intrasternal injection and infusion.

In various aspects, the present disclosure also relates to a pharmaceutical composition comprising a pharmaceutically acceptable carrier or diluent and, as active ingredient, and at least one disclosed therapeutic APBA peptide. In a further aspect, at least one disclosed therapeutic APBA peptide may be formulated into various pharmaceutical forms for administration purposes.

Pharmaceutically acceptable salts can be prepared from pharmaceutically acceptable non-toxic bases or acids. For therapeutic use, salts of the disclosed therapeutic APBA peptide are those wherein the counter ion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not, are contemplated by the present disclosure. Pharmaceutically acceptable acid and base addition salts are meant to comprise the therapeutically active non-toxic acid and base addition salt forms which the disclosed compounds are able to form.

In various aspects, a disclosed therapeutic APBA peptide comprising an acidic group or moiety, e.g., a carboxylic acid group, can be used to prepare a pharmaceutically acceptable salt. For example, such a disclosed compound may comprise an isolation step comprising treatment with a suitable inorganic or organic base. In some cases, it may be desirable in practice to initially isolate a compound from the reaction mixture as a pharmaceutically unacceptable salt and then simply convert the latter back to the free acid compound by treatment with an acidic reagent, and subsequently convert the free acid to a pharmaceutically acceptable base addition salt. These base addition salts can be readily prepared using conventional techniques, e.g., by treating the corresponding acidic compounds with an aqueous solution containing the desired pharmacologically acceptable cations and then evaporating the resulting solution to dryness, preferably under reduced pressure. Alternatively, they also can be prepared by mixing lower alkanolic solutions of the acidic compounds and the desired alkali metal alkoxide together, and then evaporating the resulting solution to dryness in the same manner as before.

Bases which can be used to prepare the pharmaceutically acceptable base-addition salts of the base compounds are those which can form non-toxic base-addition salts, i.e., salts containing pharmacologically acceptable cations such as, alkali metal cations (e.g., lithium, potassium and sodium), alkaline earth metal cations (e.g., calcium and magnesium), ammonium or other water-soluble amine addition salts such as N-methylglucamine-(meglumine), lower alkanolammonium and other such bases of organic amines. In a further aspect, derived from pharmaceutically acceptable organic non-toxic bases include primary, secondary, and tertiary amines, as well as cyclic amines and substituted amines such as naturally occurring and synthesized substituted amines. In various aspects, such pharmaceutically acceptable organic non-toxic bases include, but are not limited to, ammonia, methylamine, ethylamine, propylamine, isopropylamine, any of the four butylamine isomers, betaine, caffeine, choline, dimethylamine, diethylamine, diethanolamine, dipropylamine, diisopropylamine, di-n-butylamine, N,N'-dibenzylethylenediamine, pyrrolidine, piperidine, morpholine, trimethylamine, triethylamine, tripropylamine, tromethamine, 2-diethylaminoethanol, 2-dimethylaminoethanol, ethanolamine, quinuclidine, pyridine, quinoline and isoquinoline; benzathine, N-methyl-D-glucamine, ethylenediamine, N-ethylmorpholine, N-ethylpiperidine, glucamine, glucosamine, methylglucamine, morpholine, piperazine, piperidine, polyamine resins, procaine, purines, theobromine, hydrabamine salts, and salts with amino acids such as, for example, histidine, arginine, lysine and the like. The foregoing salt forms can be converted by treatment with acid back into the free acid form.

In various aspects, a disclosed therapeutic APBA peptide comprising a protonatable group or moiety, e.g., an amino group, can be used to prepare a pharmaceutically acceptable salt. For example, such a disclosed compound may comprise an isolation step comprising treatment with a suitable inorganic or organic acid. In some cases, it may be desirable in practice to initially isolate a compound from the reaction mixture as a pharmaceutically unacceptable salt and then simply convert the latter back to the free base compound by treatment with an basoc reagent, and subsequently convert the free base to a pharmaceutically acceptable acid addition salt. These acid addition salts can be readily prepared using conventional techniques, e.g., by treating the corresponding basic compounds with an aqueous solution containing the desired pharmacologically acceptable anions and then evaporating the resulting solution to dryness, preferably under reduced pressure. Alternatively, they also can be prepared by treating the free base form of the disclosed compound with a suitable pharmaceutically acceptable non-toxic inorganic or organic acid.

Acids which can be used to prepare the pharmaceutically acceptable acid-addition salts of the base compounds are those which can form non-toxic acid-addition salts, i.e., salts containing pharmacologically acceptable anions formed from their corresponding inorganic and organic acids. Exemplary, but non-limiting, inorganic acids include hydrochloric hydrobromic, sulfuric, nitric, phosphoric and the like. Exemplary, but non-limiting, organic acids include acetic, benzenesulfonic, benzoic, camphorsulfonic, citric, ethanesulfonic, fumaric, gluconic, glutamic, isethionic, lactic, maleic, malic, mandelicmethanesulfonic, mucic, pamoic, pantothenic, succinic, tartaric, p-toluenesulfonic acid and the like. In a further aspect, the acid-addition salt comprises an anion formed from hydrobromic, hydrochloric, maleic, phosphoric, sulfuric, and tartaric acids.

In practice, the therapeutic APBA peptides of the present disclosure, or pharmaceutically acceptable salts thereof, of the present disclosure can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present disclosure can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the present disclosure, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

It is especially advantageous to formulate the aforementioned pharmaceutical compositions in unit dosage form for ease of administration and uniformity of dosage. The term "unit dosage form," as used herein, refers to physically discrete units suitable as unitary dosages, each unit containing a predetermined quantity of active ingredient calculated to produce the desired therapeutic effect in association with the required pharmaceutical carrier. That is, a "unit dosage form" is taken to mean a single dose wherein all active and inactive ingredients are combined in a suitable system, such that the patient or person administering the drug to the patient can open a single container or package with the entire dose contained therein, and does not have to mix any components together from two or more containers or packages. Typical examples of unit dosage forms are tablets (including scored or coated tablets), capsules or pills for oral administration; single dose vials for injectable solutions or suspension; suppositories for rectal administration; powder packets; wafers; and segregated multiples thereof. This list of unit dosage forms is not intended to be limiting in any way, but merely to represent typical examples of unit dosage forms.

The pharmaceutical compositions disclosed herein comprise a therapeutic APBA peptide of the present disclosure (or pharmaceutically acceptable salts thereof) as an active ingredient, a pharmaceutically acceptable carrier, and optionally one or more additional therapeutic agents. In various aspects, the disclosed pharmaceutical compositions can include a pharmaceutically acceptable carrier and a disclosed compound, or a pharmaceutically acceptable salt thereof. In a further aspect, a disclosed compound, or pharmaceutically acceptable salt thereof, can also be included in a pharmaceutical composition in combination with one or more other therapeutically active compounds. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Techniques and compositions for making dosage forms useful for materials and methods described herein are described, for example, in the following references: Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modern Pharmaceutics Drugs and the Pharmaceutical Sciences, Vol 40 (Gilbert S. Banker, Christopher T. Rhodes, Eds.).

The therapeutic APBA peptides described herein are typically to be administered in admixture with suitable pharmaceutical diluents, excipients, extenders, or carriers (termed herein as a pharmaceutically acceptable carrier, or a carrier) suitably selected with respect to the intended form of administration and as consistent with conventional pharmaceutical practices. The deliverable compound will be in a form suitable for oral, rectal, topical, intravenous injection or parenteral administration. Carriers include solids or liquids, and the type of carrier is chosen based on the type of administration being used. The compounds may be administered as a dosage that has a known quantity of the compound.

Because of the ease in administration, oral administration can be a preferred dosage form, and tablets and capsules represent the most advantageous oral dosage unit forms in which case solid pharmaceutical carriers are obviously employed. However, other dosage forms may be suitable depending upon clinical population (e.g., age and severity of clinical condition), solubility properties of the specific disclosed compound used, and the like. Accordingly, the disclosed compounds can be used in oral dosage forms such as pills, powders, granules, elixirs, tinctures, suspensions, syrups, and emulsions. In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques.

The disclosed pharmaceutical compositions in an oral dosage form can comprise one or more pharmaceutical excipient and/or additive. Non-limiting examples of suitable excipients and additives include gelatin, natural sugars such as raw sugar or lactose, lecithin, pectin, starches (for example corn starch or amylose), dextran, polyvinyl pyrrolidone, polyvinyl acetate, gum arabic, alginic acid, tylose, talcum, lycopodium, silica gel (for example colloidal), cellulose, cellulose derivatives (for example cellulose ethers in which the cellulose hydroxy groups are partially etherified with lower saturated aliphatic alcohols and/or lower saturated, aliphatic oxyalcohols, for example methyl oxypropyl cellulose, methyl cellulose, hydroxypropyl methyl cellulose, hydroxypropyl methyl cellulose phthalate), fatty acids as well as magnesium, calcium or aluminum salts of fatty acids with 12 to 22 carbon atoms, in particular saturated (for example stearates), emulsifiers, oils and fats, in particular vegetable (for example, peanut oil, castor oil, olive oil, sesame oil, cottonseed oil, corn oil, wheat germ oil, sunflower seed oil, cod liver oil, in each case also optionally hydrated); glycerol esters and polyglycerol esters of saturated fatty acids $C_{12}H_{24}O_2$ to $C_{18}H_{36}O_2$ and their mixtures, it being possible for the glycerol hydroxy groups to be totally or also only partly esterified (for example mono-, di- and triglycerides); pharmaceutically acceptable mono- or multivalent alcohols and polyglycols such as polyethylene glycol and derivatives thereof, esters of aliphatic saturated or unsaturated fatty acids (2 to 22 carbon atoms, in particular 10-18 carbon atoms) with monovalent aliphatic alcohols (1 to 20 carbon atoms) or multivalent alcohols such as glycols, glycerol, diethylene glycol, pentacrythritol, sorbitol, mannitol and the like, which may optionally also be etherified, esters of citric acid with primary alcohols, acetic acid, urea, benzyl benzoate, dioxolanes, glyceroformals, tetrahydrofurfuryl alcohol, polyglycol ethers with C1-C12-alcohols, dimethylacetamide, lactamides, lactates, ethylcarbonates, silicones (in particular medium-viscous polydimethyl siloxanes), calcium carbonate, sodium carbonate, calcium phosphate, sodium phosphate, magnesium carbonate and the like.

Other auxiliary substances useful in preparing an oral dosage form are those which cause disintegration (so-called disintegrants), such as: cross-linked polyvinyl pyrrolidone, sodium carboxymethyl starch, sodium carboxymethyl cellulose or microcrystalline cellulose. Conventional coating substances may also be used to produce the oral dosage form. Those that may for example be considered are: polymerizates as well as copolymerizates of acrylic acid and/or methacrylic acid and/or their esters; copolymerizates of acrylic and methacrylic acid esters with a lower ammonium group content (for example EudragitR RS), copolymerizates of acrylic and methacrylic acid esters and trimethyl ammonium methacrylate (for example EudragitR RL); polyvinyl acetate; fats, oils, waxes, fatty alcohols; hydroxypropyl methyl cellulose phthalate or acetate succinate; cellulose acetate phthalate, starch acetate phthalate as well as polyvinyl acetate phthalate, carboxy methyl cellulose; methyl cellulose phthalate, methyl cellulose succinate, -phthalate succinate as well as methyl cellulose phthalic acid half ester; zein; ethyl cellulose as well as ethyl cellulose succinate; shellac, gluten; ethylcarboxyethyl cellulose; ethacrylate-maleic acid anhydride copolymer; maleic acid anhydride-vinyl methyl ether copolymer; styrol-maleic acid copolymerizate; 2-ethyl-hexyl-acrylate maleic acid anhydride; crotonic acid-vinyl acetate copolymer; glutaminic acid/glutamic acid ester copolymer; carboxymethylethylcellulose glycerol monooctanoate; cellulose acetate succinate; polyarginine.

Plasticizing agents that may be considered as coating substances in the disclosed oral dosage forms are: citric and tartaric acid esters (acetyl-triethyl citrate, acetyl tributyl-, tributyl-, triethyl-citrate); glycerol and glycerol esters (glycerol diacetate, -triacetate, acetylated monoglycerides, castor oil); phthalic acid esters (dibutyl-, diamyl-, diethyl-, dimethyl-, dipropyl-phthalate), di-(2-methoxy- or 2-ethoxyethyl)-phthalate, ethylphthalyl glycolate, butylphthalylethyl glycolate and butylglycolate; alcohols (propylene glycol, polyethylene glycol of various chain lengths), adipates (diethyladipate, di-(2-methoxy- or 2-ethoxyethyl)-adipate; benzophenone; diethyl- and diburylsebacate, dibutylsuccinate, dibutyltartrate; diethylene glycol dipropionate; ethyleneglycol diacetate, -dibutyrate, -dipropionate; tributyl phosphate, tributyrin; polyethylene glycol sorbitan monooleate (polysorbates such as Polysorbar 50); sorbitan monooleate.

Moreover, suitable binders, lubricants, disintegrating agents, coloring agents, flavoring agents, flow-inducing agents, and melting agents may be included as carriers. The pharmaceutical carrier employed can be, for example, a solid, liquid, or gas. Examples of solid carriers include, but are not limited to, lactose, terra alba, sucrose, glucose, methylcellulose, dicalcium phosphate, calcium sulfate, mannitol, sorbitol talc, starch, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In various aspects, a binder can include, for example, starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. In a further aspect, a disintegrator can include, for example, starch, methyl cellulose, agar, bentonite, xanthan gum, and the like.

In various aspects, an oral dosage form, such as a solid dosage form, can comprise a disclosed compound that is attached to polymers as targetable drug carriers or as a prodrug. Suitable biodegradable polymers useful in achieving controlled release of a drug include, for example, polylactic acid, polyglycolic acid, copolymers of polylactic and polyglycolic acid, caprolactones, polyhydroxy butyric acid, polyorthoesters, polyacetals, polydihydropyrans, polycyanoacylates, and hydrogels, preferably covalently crosslinked hydrogels.

Tablets may contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period.

A tablet containing a disclosed compound can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

In various aspects, a solid oral dosage form, such as a tablet, can be coated with an enteric coating to prevent ready decomposition in the stomach. In various aspects, enteric coating agents include, but are not limited to, hydroxypropylmethylcellulose phthalate, methacrylic acid-methacrylic acid ester copolymer, polyvinyl acetate-phthalate and cellulose acetate phthalate. Akihiko Hasegawa "Application of solid dispersions of Nifedipine with enteric coating agent to prepare a sustained-release dosage form" Chem. Pharm. Bull. 33:1615-1619 (1985). Various enteric coating materials may be selected on the basis of testing to achieve an enteric coated dosage form designed ab initio to have a preferable combination of dissolution time, coating thicknesses and diametral crushing strength (e.g., see S. C. Porter et al. "The Properties of Enteric Tablet Coatings Made From Polyvinyl Acetate-phthalate and Cellulose acetate Phthalate", J. Pharm. Pharmacol. 22:42p (1970)). In a further aspect, the enteric coating may comprise hydroxypropylmethylcellulose phthalate, methacrylic acid-methacrylic acid ester copolymer, polyvinyl acetate-phthalate and cellulose acetate phthalate.

In various aspects, an oral dosage form can be a solid dispersion with a water soluble or a water insoluble carrier. Examples of water soluble or water insoluble carrier include, but are not limited to, polyethylene glycol, polyvinylpyrrolidone, hydroxypropylmethylcellulose, phosphatidylcholine, polyoxyethylene hydrogenated castor oil, hydroxypropylmethylcellulose phthalate, carboxymethylethylcellulose, or hydroxypropylmethylcellulose, ethyl cellulose, or stearic acid.

In various aspects, an oral dosage form can be in a liquid dosage form, including those that are ingested, or alternatively, administered as a mouth wash or gargle. For example, a liquid dosage form can include aqueous suspensions, which contain the active materials in admixture with excipients suitable for the manufacture of aqueous suspensions. In addition, oily suspensions may be formulated by suspending the active ingredient in a vegetable oil, for example arachis oil, olive oil, sesame oil or coconut oil, or in a mineral oil such as liquid paraffin. Oily suspensions may also contain various excipients. The pharmaceutical compositions of the present disclosure may also be in the form of oil-in-water emulsions, which may also contain excipients such as sweetening and flavoring agents.

For the preparation of solutions or suspensions it is, for example, possible to use water, particularly sterile water, or physiologically acceptable organic solvents, such as alcohols (ethanol, propanol, isopropanol, 1,2-propylene glycol, polyglycols and their derivatives, fatty alcohols, partial esters of glycerol), oils (for example peanut oil, olive oil, sesame oil, almond oil, sunflower oil, soya bean oil, castor oil, bovine hoof oil), paraffins, dimethyl sulphoxide, triglycerides and the like.

In the case of a liquid dosage form such as a drinkable solutions, the following substances may be used as stabilizers or solubilizers: lower aliphatic mono- and multivalent alcohols with 2-4 carbon atoms, such as ethanol, n-propanol, glycerol, polyethylene glycols with molecular weights between 200-600 (for example 1 to 40% aqueous solution), diethylene glycol monoethyl ether, 1,2-propylene glycol, organic amides, for example amides of aliphatic C1-C6-carboxylic acids with ammonia or primary, secondary or tertiary C1-C4-amines or C1-C4-hydroxy amines such as urea, urethane, acetamide, N-methyl acetamide, N,N-diethyl acetamide, N,N-dimethyl acetamide, lower aliphatic amines and diamines with 2-6 carbon atoms, such as ethylene diamine, hydroxyethyl theophylline, tromethamine (for example as 0.1 to 20% aqueous solution), aliphatic amino acids.

In preparing the disclosed liquid dosage form can comprise solubilizers and emulsifiers such as the following non-limiting examples can be used: polyvinyl pyrrolidone, sorbitan fatty acid esters such as sorbitan trioleate, phosphatides such as lecithin, acacia, tragacanth, polyoxyethylated sorbitan monooleate and other ethoxylated fatty acid esters of sorbitan, polyoxyethylated fats, polyoxyethylated oleotriglycerides, linolizated oleotriglycerides, polyethylene oxide condensation products of fatty alcohols, alkylphenols or fatty acids or also 1-methyl-3-(2-hydroxyethyl)imidazolidone-(2). In this context, polyoxyethylated means that the substances in question contain polyoxyethylene chains, the degree of polymerization of which generally lies between 2 and 40 and in particular between 10 and 20. Polyoxyethylated substances of this kind may for example be obtained by reaction of hydroxyl group-containing compounds (for example mono- or diglycerides or unsaturated compounds such as those containing oleic acid radicals) with ethylene oxide (for example 40 Mol ethylene oxide per 1 Mol glyceride). Examples of oleotriglycerides are olive oil, peanut oil, castor oil, sesame oil, cottonseed oil, corn oil. See also Dr. H. P. Fiedler "Lexikon der Hillsstoffe für Pharmazie, Kostnetik and angrenzende Gebiete" 1971, pages 191-195.

In various aspects, a liquid dosage form can further comprise preservatives, stabilizers, buffer substances, flavor correcting agents, sweeteners, colorants, antioxidants and complex formers and the like. Complex formers which may be for example be considered are: chelate formers such as ethylene diamine retrascetic acid, nitrilotriacetic acid, diethylene triamine pentacetic acid and their salts.

It may optionally be necessary to stabilize a liquid dosage form with physiologically acceptable bases or buffers to a pH range of approximately 6 to 9. Preference may be given to as neutral or weakly basic a pH value as possible (up to pH 8).

In order to enhance the solubility and/or the stability of a disclosed compound in a disclosed liquid dosage form, a parenteral injection form, or an intravenous injectable form, it can be advantageous to employ α-, β- or γ-cyclodextrins or their derivatives, in particular hydroxyalkyl substituted cyclodextrins, e.g. 2-hydroxypropyl-β-cyclodextrin or sulfobutyl-β-cyclodextrin. Also co-solvents such as alcohols may improve the solubility and/or the stability of the compounds according to the present disclosure in pharmaceutical compositions.

In various aspects, a disclosed liquid dosage form, a parenteral injection form, or an intravenous injectable form can further comprise liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Pharmaceutical compositions of the present disclosure suitable injection, such as parenteral administration, such as intravenous, intramuscular, or subcutaneous administration.

Pharmaceutical compositions for injection can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present disclosure suitable for parenteral administration can include sterile aqueous or oleaginous solutions, suspensions, or dispersions. Furthermore, the compositions can be in the form of sterile powders for the extemporaneous preparation of such sterile injectable solutions or dispersions. In some aspects, the final injectable form is sterile and must be effectively fluid for use in a syringe. The pharmaceutical compositions should be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Injectable solutions, for example, can be prepared in which the carrier comprises saline solution, glucose solution or a mixture of saline and glucose solution. Injectable suspensions may also be prepared in which case appropriate liquid carriers, suspending agents and the like may be employed. In some aspects, a disclosed parenteral formulation can comprise about 0.01-0.1 M, e.g. about 0.05 M, phosphate buffer. In a further aspect, a disclosed parenteral formulation can comprise about 0.9% saline.

In various aspects, a disclosed parenteral pharmaceutical composition can comprise pharmaceutically acceptable carriers such as aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include but not limited to water, alcoholic/aqueous solutions, emulsions or suspensions, including saline and buffered media. Parenteral vehicles can include mannitol, normal serum albumin, sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like. In a further aspect, a disclosed parenteral pharmaceutical composition can comprise may contain minor amounts of additives such as substances that enhance isotonicity and chemical stability, e.g., buffers and preservatives. Also contemplated for injectable pharmaceutical compositions are solid form preparations that are intended to be converted, shortly before use, to liquid form preparations. Furthermore, other adjuvants can be included to render the formulation isotonic with the blood of the subject or patient.

In addition to the pharmaceutical compositions described herein above, the disclosed compounds can also be formulated as a depot preparation. Such long acting formulations can be administered by implantation (e.g., subcutaneously or intramuscularly) or by intramuscular injection. Thus, for example, the compounds can be formulated with suitable polymeric or hydrophobic materials (e.g., as an emulsion in an acceptable oil) or ion exchange resins, or as sparingly soluble derivatives, e.g., as a sparingly soluble salt.

Pharmaceutical compositions of the present disclosure can be in a form suitable for topical administration. As used herein, the phrase "topical application" means administration onto a biological surface, whereby the biological surface includes, for example, a skin area (e.g., hands, forearms, elbows, legs, face, nails, anus and genital areas) or a mucosal membrane. By selecting the appropriate carrier and optionally other ingredients that can be included in the composition, as is detailed herein below, the compositions of the present invention may be formulated into any form typically employed for topical application. A topical pharmaceutical composition can be in a form of a cream, an ointment, a paste, a gel, a lotion, milk, a suspension, an aerosol, a spray, foam, a dusting powder, a pad, and a patch. Further, the compositions can be in a form suitable for use in transdermal devices. These formulations can be prepared, utilizing a compound of the present disclosure, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment.

Ointments are semisolid preparations, typically based on petrolatum or petroleum derivatives. The specific ointment base to be used is one that provides for optimum delivery for the active agent chosen for a given formulation, and, preferably, provides for other desired characteristics as well (e.g., emollience). As with other carriers or vehicles, an ointment base should be inert, stable, nonirritating and nonsensitizing. As explained in Remington: The Science and Practice of Pharmacy, 19th Ed., Easton, Pa.: Mack Publishing Co. (1995), pp. 1399-1404, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin and stearic acid. Preferred water-soluble ointment bases are prepared from polyethylene glycols of varying molecular weight.

Lotions are preparations that are to be applied to the skin surface without friction. Lotions are typically liquid or semiliquid preparations in which solid particles, including the active agent, are present in a water or alcohol base. Lotions are typically preferred for treating large body areas, due to the ease of applying a more fluid composition. Lotions are typically suspensions of solids, and oftentimes comprise a liquid oily emulsion of the oil-in-water type. It is generally necessary that the insoluble matter in a lotion be finely divided. Lotions typically contain suspending agents to produce better dispersions as well as compounds useful for localizing and holding the active agent in contact with the skin, such as methylcellulose, sodium carboxymethylcellulose, and the like.

Creams are viscous liquids or semisolid emulsions, either oil-in-water or water-in-oil. Cream bases are typically water-washable, and contain an oil phase, an emulsifier and an aqueous phase. The oil phase, also called the "internal" phase, is generally comprised of petrolatum and/or a fatty alcohol such as cetyl or stearyl alcohol. The aqueous phase typically, although not necessarily, exceeds the oil phase in volume, and generally contains a humectant. The emulsifier in a cream formulation is generally a nonionic, anionic, cationic or amphoteric surfactant. Reference may be made to Remington: The Science and Practice of Pharmacy, supra, for further information.

Pastes are semisolid dosage forms in which the bioactive agent is suspended in a suitable base. Depending on the nature of the base, pastes are divided between fatty pastes or those made from a single-phase aqueous gel. The base in a fatty paste is generally petrolatum, hydrophilic petrolatum and the like. The pastes made from single-phase aqueous gels generally incorporate carboxymethylcellulose or the like as a base. Additional reference may be made to Remington: The Science and Practice of Pharmacy, for further information.

Gel formulations are semisolid, suspension-type systems. Single-phase gels contain organic macromolecules distributed substantially uniformly throughout the carrier liquid, which is typically aqueous, but also, preferably, contain an alcohol and, optionally, an oil. Preferred organic macromolecules, i.e., gelling agents, are crosslinked acrylic acid polymers such as the family of carbomer polymers, e.g., carboxypolyalkylenes that may be obtained commercially under the trademark Carbopol™. Other types of preferred polymers in this context are hydrophilic polymers such as polyethylene oxides, polyoxyethylene-polyoxypropylene copolymers and polyvinylalcohol; modified cellulose, such as hydroxypropyl cellulose, hydroxyethyl cellulose, hydroxypropyl methylcellulose, hydroxypropyl methylcellulose phthalate, and methyl cellulose; gums such as tragacanth and xanthan gum; sodium alginate; and gelatin. In order to prepare a uniform gel, dispersing agents such as alcohol or glycerin can be added, or the gelling agent can be dispersed by trituration, mechanical mixing or stirring, or combinations thereof.

Sprays generally provide the active agent in an aqueous and/or alcoholic solution which can be misted onto the skin for delivery. Such sprays include those formulated to provide for concentration of the active agent solution at the site of administration following delivery, e.g., the spray solution can be primarily composed of alcohol or other like volatile liquid in which the active agent can be dissolved. Upon delivery to the skin, the carrier evaporates, leaving concentrated active agent at the site of administration.

Foam compositions are typically formulated in a single or multiple phase liquid form and housed in a suitable container, optionally together with a propellant which facilitates the expulsion of the composition from the container, thus transforming it into a foam upon application. Other foam forming techniques include, for example the "Bag-in-a-can" formulation technique. Compositions thus formulated typically contain a low-boiling hydrocarbon, e.g., isopropane. Application and agitation of such a composition at the body temperature cause the isopropane to vaporize and generate the foam, in a manner similar to a pressurized aerosol foaming system. Foams can be water-based or aqueous alkanolic, but are typically formulated with high alcohol content which, upon application to the skin of a user, quickly evaporates, driving the active ingredient through the upper skin layers to the site of treatment.

Skin patches typically comprise a backing, to which a reservoir containing the active agent is attached. The reservoir can be, for example, a pad in which the active agent or composition is dispersed or soaked, or a liquid reservoir. Patches typically further include a frontal water permeable adhesive, which adheres and secures the device to the treated region. Silicone rubbers with self-adhesiveness can alternatively be used. In both cases, a protective permeable layer can be used to protect the adhesive side of the patch prior to its use. Skin patches may further comprise a removable cover, which serves for protecting it upon storage.

Examples of patch configuration which can be utilized with the present invention include a single-layer or multi-layer drug-in-adhesive systems which are characterized by the inclusion of the drug directly within the skin-contacting adhesive. In such a transdermal patch design, the adhesive not only serves to affix the patch to the skin, but also serves as the formulation foundation, containing the drug and all the excipients under a single backing film. In the multi-layer drug-in-adhesive patch a membrane is disposed between two distinct drug-in-adhesive layers or multiple drug-in-adhesive layers are incorporated under a single backing film.

Examples of pharmaceutically acceptable carriers that are suitable for pharmaceutical compositions for topical applications include carrier materials that are well-known for use in the cosmetic and medical arts as bases for e.g., emulsions, creams, aqueous solutions, oils, ointments, pastes, gels, lotions, milks, foams, suspensions, aerosols and the like, depending on the final form of the composition. Representative examples of suitable carriers according to the present invention therefore include, without limitation, water, liquid alcohols, liquid glycols, liquid polyalkylene glycols, liquid esters, liquid amides, liquid protein hydrolysates, liquid alkylated protein hydrolysates, liquid lanolin and lanolin derivatives, and like materials commonly employed in cosmetic and medicinal compositions. Other suitable carriers according to the present invention include, without limitation, alcohols, such as, for example, monohydric and polyhydric alcohols, e.g., ethanol, isopropanol, glycerol, sorbitol, 2-methoxyethanol, diethyleneglycol, ethylene glycol, hexyleneglycol, mannitol, and propylene glycol; ethers such as diethyl or dipropyl ether; polyethylene glycols and methoxypolyoxyethylenes (carbowaxes having molecular weight ranging from 200 to 20,000); polyoxyethylene glycerols, polyoxyethylene sorbitols, stearoyl diacetin, and the like.

Topical compositions of the present disclosure can, if desired, be presented in a pack or dispenser device, such as an FDA-approved kit, which may contain one or more unit dosage forms containing the active ingredient. The dispenser device may, for example, comprise a tube. The pack or dispenser device may be accompanied by instructions for administration. The pack or dispenser device may also be accompanied by a notice in a form prescribed by a governmental agency regulating the manufacture, use, or sale of pharmaceuticals, which notice is reflective of approval by the agency of the form of the compositions for human or veterinary administration. Such notice, for example, may include labeling approved by the U.S. Food and Drug Administration for prescription drugs or of an approved product insert. Compositions comprising the topical composition of the invention formulated in a pharmaceutically acceptable carrier may also be prepared, placed in an appropriate container, and labeled for treatment of an indicated condition.

Another patch system configuration which can be used by the present invention is a reservoir transdermal system design which is characterized by the inclusion of a liquid compartment containing a drug solution or suspension separated from the release liner by a semi-permeable membrane and adhesive. The adhesive component of this patch system can either be incorporated as a continuous layer between the membrane and the release liner or in a concentric configuration around the membrane. Yet another patch system configuration which can be utilized by the present invention is a matrix system design which is characterized by the inclusion of a semisolid matrix containing a drug solution or suspension which is in direct contact with the release liner. The component responsible for skin adhesion is incorporated in an overlay and forms a concentric configuration around the semisolid matrix.

Pharmaceutical compositions of the present disclosure can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in molds.

Pharmaceutical compositions containing a compound of the present disclosure, and/or pharmaceutically acceptable salts thereof, can also be prepared in powder or liquid concentrate form.

The pharmaceutical composition (or formulation) may be packaged in a variety of ways. Generally, an article for distribution includes a container that contains the pharmaceutical composition in an appropriate form. Suitable containers are well known to those skilled in the art and include materials such as bottles (plastic and glass), sachets, foil blister packs, and the like. The container may also include a tamper proof assemblage to prevent indiscreet access to the contents of the package. In addition, the container typically has deposited thereon a label that describes the contents of the container and any appropriate warnings or instructions.

The disclosed pharmaceutical compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Pharmaceutical compositions comprising a disclosed compound formulated in a compatible pharmaceutical carrier may also be prepared, placed in an appropriate container, and labeled for treatment of an indicated condition.

The exact dosage and frequency of administration depends on the particular disclosed compound, a product of a disclosed method of making, a pharmaceutically acceptable salt, solvate, or polymorph thereof, a hydrate thereof, a solvate thereof, a polymorph thereof, or a stereochemically isomeric form thereof; the particular condition being treated and the severity of the condition being treated; various factors specific to the medical history of the subject to whom the dosage is administered such as the age; weight, sex, extent of disorder and general physical condition of the particular subject, as well as other medication the individual may be taking; as is well known to those skilled in the art.

Furthermore, it is evident that said effective daily amount may be lowered or increased depending on the response of the treated subject and/or depending on the evaluation of the physician prescribing the compounds of the present disclosure.

Depending on the mode of administration, the pharmaceutical composition will comprise from 0.05 to 99% by weight, preferably from 0.1 to 70% by weight, more preferably from 0.1 to 50% by weight of the active ingredient, and, from 1 to 99.95% by weight, preferably from 30 to 99.9% by weight, more preferably from 50 to 99.9% by weight of a pharmaceutically acceptable carrier, all percentages being based on the total weight of the composition.

In the treatment conditions which require of a microbial infection an appropriate dosage level will generally be about 0.01 to 1000 mg per kg patient body weight per day and can be administered in single or multiple doses. In various aspects, the dosage level will be about 0.1 to about 500 mg/kg per day, about 0.1 to 250 mg/kg per day, or about 0.5 to 100 mg/kg per day. A suitable dosage level can be about 0.01 to 1000 mg/kg per day, about 0.01 to 500 mg/kg per day, about 0.01 to 250 mg/kg per day, about 0.05 to 100 mg/kg per day, or about 0.1 to 50 mg/kg per day. Within this range the dosage can be 0.05 to 0.5, 0.5 to 5.0 or 5.0 to 50 mg/kg per day. For oral administration, the compositions are preferably provided in the form of tablets containing 1.0 to 1000 mg of the active ingredient, particularly 1.0, 5.0, 10, 15, 20, 25, 50, 75, 100, 150, 200, 250, 300, 400, 500, 600, 750, 800, 900 and 1000 mg of the active ingredient for the symptomatic adjustment of the dosage of the patient to be treated. The compound can be administered on a regimen of 1 to 4 times per day, preferably once or twice per day. This dosing regimen can be adjusted to provide the optimal therapeutic response.

Such unit doses as described hereinabove and hereinafter can be administered more than once a day, for example, 2, 3, 4, 5 or 6 times a day. In various aspects, such unit doses can be administered 1 or 2 times per day, so that the total dosage for a 70 kg adult is in the range of 0.001 to about 15 mg per kg weight of subject per administration. In a further aspect, dosage is 0.01 to about 1.5 mg per kg weight of subject per administration, and such therapy can extend for a number of weeks or months, and in some cases, years. It will be understood, however, that the specific dose level for any particular patient will depend on a variety of factors including the activity of the specific compound employed; the age, body weight, general health, sex and diet of the individual being treated; the time and route of administration; the rate of excretion; other drugs that have previously been administered; and the severity of the particular disease undergoing therapy, as is well understood by those of skill in the area.

A typical dosage can be one 1 mg to about 100 mg tablet or 1 mg to about 300 mg taken once a day, or, multiple times per day, or one time-release capsule or tablet taken once a day and containing a proportionally higher content of active ingredient. The time-release effect can be obtained by capsule materials that dissolve at different pH values, by capsules that release slowly by osmotic pressure, or by any other known means of controlled release.

It can be necessary to use dosages outside these ranges in some cases as will be apparent to those skilled in the art. Further, it is noted that the clinician or treating physician will know how and when to start, interrupt, adjust, or terminate therapy in conjunction with individual patient response.

The present disclosure is further directed to a method for the manufacture of a medicament for anti-microbial activity (e.g., treatment of one or more microbial infections) in mammals (e.g., humans) comprising combining one or more disclosed therapeutic APBA peptides with a pharmaceutically acceptable carrier or diluent. Thus, in one aspect, the present disclosure further relates to a method for manufacturing a medicament comprising combining at least one disclosed therapeutic APBA peptide with a pharmaceutically acceptable carrier or diluent.

The disclosed pharmaceutical compositions can further comprise other therapeutically active compounds, which are usually applied in the treatment of the above mentioned pathological or clinical conditions.

It is understood that the disclosed compositions can be prepared from the disclosed therapeutic APBA peptides. It is also understood that the disclosed compositions can be employed in the disclosed methods of using.

As already mentioned, the present disclosure relates to a pharmaceutical composition comprising a therapeutically effective amount of a disclosed therapeutic APBA peptide, a pharmaceutically acceptable salt thereof, and a pharmaceutically acceptable carrier. Additionally, the present disclosure relates to a process for preparing such a pharmaceutical composition, characterized in that a pharmaceutically acceptable carrier is intimately mixed with a therapeutically effective amount of a compound according to the present disclosure.

As already mentioned, the present disclosure also relates to a pharmaceutical composition comprising a disclosed compound, a product of a disclosed method of making, a pharmaceutically acceptable salt, a hydrate thereof, a solvate thereof, a polymorph thereof, and one or more other drugs in the treatment, prevention, control, amelioration, or reduction of risk of diseases or conditions for a disclosed compound or the other drugs may have utility as well as to the use of such a composition for the manufacture of a medicament. The present disclosure also relates to a combination of disclosed therapeutic APBA peptide, a pharmaceutically acceptable salt thereof, and a therapeutic agent that is known to treat a microbial infection. The present disclosure also relates to such a combination for use as a medicine. The present disclosure also relates to a product comprising (a) disclosed therapeutic APBA peptide, or a pharmaceutically acceptable salt thereof, and (b) an additional antimicrobial therapeutic agent, as a combined preparation for simultaneous, separate or sequential use in the treatment or prevention of a condition in a mammal, including a human, the treatment or prevention of which is affected or facilitated by the modulatory effect of the disclosed compound and the additional therapeutic agent. The different drugs of such a combination or product may be combined in a single preparation together with pharmaceutically acceptable carriers or diluents, or they may each be present in a separate preparation together with pharmaceutically acceptable carriers or diluents.

Methods of Using Therapeutic APBA Peptides

In various aspects, the present disclosure provides methods of treating an infectious disease comprising administration of a therapeutically effective amount of a disclosed APBA therapeutic peptide or a disclosed pharmaceutical composition to a subject in need thereof. It is understood that reference to a disclosed APBA therapeutic peptide is inclusive of the disclosed APBA therapeutic peptide, as well as pharmaceutically acceptable salt, hydrate, solvate, or polymorph forms thereof and a disclosed APBA therapeutic peptide further comprising an an antibiotic residue, a phototoxin residue, and/or a detectable label residue; and reference to a disclosed pharmaceutical composition is inclusive of a pharmaceutical composition comprising a disclosed APBA therapeutic peptide or pharmaceutically acceptable salt, hydrate, solvate, or polymorph forms of a disclosed APBA therapeutic peptide, and pharmaceutical compositions comprising a disclosed APBA therapeutic peptide further comprising an an antibiotic residue, a phototoxin residue, and/or a detectable label residue.

It is understood that treating an infectious is inclusive of treating, preventing, ameliorating, controlling or reducing the risk of a variety of bacterial infections, including an infection associated with Gram positive bacteria, Gram negative bacteria, or mycobacteria, wherein the patient or subject would benefit from an antibacterial agent. For example, a treatment can include binding a disclosed APBA therapeutic peptide, optionally further comprising an antibiotic residue, a phototoxin residue, and/or a detectable label residue, to a target bacteria in a subject infected with said target bacteria, and wherein the disclosed APBA therapeutic peptide via binding and/or binding with delivery of an an antibiotic residue, a phototoxin residue, and/or a detectable label residue to the target bacteria. In one aspect, provided is a method of treating or preventing a bacterial infection in a subject comprising the step of administering to the subject at least one disclosed APBA therapeutic peptide or at least one disclosed pharmaceutical composition in a dosage and amount effective to treat the disorder in the subject.

Also provided is a method for the treatment of one or more disorders associated with infection by a target bacteria wherein inhibiting binding of a disclosed APBA therapeutic peptide can sterilize or decrease the presence of the pathogenic bacteria in a subject comprising the step of administering to the subject at least one disclosed APBA therapeutic peptide or at least one disclosed pharmaceutical composition in a dosage and amount effective to treat the disorder in the subject.

Also provided is a method for the treatment of a bacterial infection in a vertebrate animal comprising the step of administering to the mammal at least one disclosed compound, composition, or medicament. In some aspects, the vertebrate animal is a mammal.

In a further aspect, the vertebrate animal is a fish, a bird, or a mammal. In a still further aspect, the vertebrate animal is a livestock animal. In yet a further aspect, the vertebrate animal is a companion animal. In an even further aspect, the vertebrate animal is a farm animal. In a still further aspect, the vertebrate animal is a zoo animal. In yet a further aspect, the vertebrate animal is a laboratory animal. In an even further aspect, the vertebrate animal is an aquaculture fish. In a still further aspect, the vertebrate animal is selected from *Bison* sp., *Bos* sp., *Canis* sp., *Capra* sp., *Equus* sp., *Felis* sp., *Gallus* sp., *Lama* sp., *Meleagris* sp., *Oryctolagus* sp., *Ovis* sp., and *Sus* sp.

In a further aspect, the vertebrate animal has been diagnosed with a need for treatment of the infectious disease prior to the administering step.

In a further aspect, the disclosure relates to a method for the treatment of an infectious disease in a vertebrate animal, further comprising the step of identifying a vertebrate animal in need of treatment of the infectious disease.

In a further aspect, administering comprises mixing an effective amount of a disclosed APBA therapeutic peptide with the food of the vertebrate animal. In a still further aspect, administering comprises administering enterally an effective amount of the disclosed APBA therapeutic peptide with the food of the vertebrate animal. In yet a further aspect, administering comprises administering an oral bolus of an effective amount of the disclosed APBA therapeutic peptide with the food of the vertebrate animal.

In various aspects, administering to a vertebrate animal comprises intravenous administration or parenteral administration to the vertebrate animal.

In a further aspect, the infectious disease treated in the vertebrate animal is selected from dental infection, dermatitis, diarrhea, ear infection, gastritis, gastroenteritis, genitourinary infection, intestinal infection, lung infection, ocular infection, oral infection, otitis, osteo-articular infection, pharyngitis, papules, pneumonia conjunctivitis, pruritius, pustules, pyoderma, pyothorax, respiratory infection, salmonellosis, septicemia, skin infection, soft tissue infection, ulcer, urinary tract infection, and wound infection.

In a further aspect, the disclosure relates to a method for the treatment of an infectious disease in a vertebrate animal, further comprising administering to the vertebrate animal a therapeutically effective amount of second active agent. In a still further aspect, the second active agent is an antibacterial agent. In yet a further aspect, the antibacterial agent is pencillin, a cephalosporin, a sulfonamide, a tetracycline, a lincosamide, an aminoglycoside, or a fluoroquinolone, or combinations thereof. In an even further aspect, the antibacterial agent comprises a compound selected from amoxicillin, ampicillin, azithromycin, cefovecin, cephalexin, chloramphenicol, ciprofloxacin, clavulanic acid, cloxacillin, clindamycin, doxycycline, enrofloxacin, erythromycin, gentamicin, ibafloxacin, kanamycin, lincomycin, marbofloxacin, metronidazole, minocycline, neomycin, novobiocin, ofloxacin, orbifloxacin, oxytetracycline, penicillin G, rifampin, sulfadimethoxine, sulfadiazine, tetracycline, tiamulin, ticarcillin, trimethoprim, and tylosin, or combinations thereof.

The disclosed APBA therapeutic peptides are further useful in a method for the prevention, treatment, control, amelioration, or reduction of risk of the bacterial infections noted herein. The disclosed APBA therapeutic peptides are further useful in a method for the prevention, treatment, control, amelioration, or reduction of risk of the aforementioned bacterial infections in combination with other agents.

In one aspect, the disclosed APBA therapeutic peptides can be used in combination with one or more other drugs in the treatment, prevention, control, amelioration, or reduction of risk of bacterial infections for which disclosed APBA therapeutic peptides or the other drugs can have utility, where the combination of the drugs together are safer or more effective than either drug alone. Such other drug(s) can be administered, by a route and in an amount commonly used therefor, contemporaneously or sequentially with a compound of the present disclosure. When a compound of the present disclosure is used contemporaneously with one or more other drugs, a pharmaceutical composition in unit dosage form containing such other drugs and a disclosed compound is preferred. However, the combination therapy can also include therapies in which a disclosed compound and one or more other drugs are administered on different overlapping schedules. It is also contemplated that when used in combination with one or more other active ingredients, the disclosed APBA therapeutic peptides and the other active ingredients can be used in lower doses than when each is used singly.

Accordingly, the pharmaceutical compositions include those that contain one or more other active ingredients, in addition to a compound of the present disclosure.

The above combinations include combinations of a disclosed compound not only with one other active compound, but also with two or more other active compounds. Likewise, disclosed APBA therapeutic peptides can be used in combination with other drugs that are used in the prevention, treatment, control, amelioration, or reduction of risk of the bacterial infections for which disclosed APBA therapeutic peptides are useful. Such other drugs can be administered, by a route and in an amount commonly used therefor, contemporaneously or sequentially with a compound of the present disclosure. When a compound of the present disclosure is used contemporaneously with one or more other drugs, a pharmaceutical composition containing such other drugs in addition to a disclosed compound is preferred. Accordingly, the pharmaceutical compositions include those that also contain one or more other active ingredients, in addition to a compound of the present disclosure.

The weight ratio of a disclosed compound to the second active ingredient can be varied and will depend upon the effective dose of each ingredient. Generally, an effective dose of each will be used. Thus, for example, when a compound of the present disclosure is combined with another agent, the weight ratio of a disclosed compound to the other agent will generally range from about 1000:1 to about 1:1000, preferably about 200:1 to about 1:200. Combinations of a compound of the present disclosure and other active ingredients will generally also be within the aforementioned range, but in each case, an effective dose of each active ingredient should be used.

In such combinations a disclosed compound and other active agents can be administered separately or in conjunction. In addition, the administration of one element can be prior to, concurrent to, or subsequent to the administration of other agent(s).

Accordingly, the disclosed APBA therapeutic peptides can be used alone or in combination with other agents which are known to be beneficial in the subject indications or other drugs that affect receptors or enzymes that either increase the efficacy, safety, convenience, or reduce unwanted side effects or toxicity of the other agents. The disclosed APBA therapeutic peptide and the other agent can be coadministered, either in concomitant therapy or in a fixed combination.

In one aspect, the compound can be employed in combination with antibacterial or antimicrobial agents, and combinations thereof, and the like, or the subject compound can be administered in conjunction with the use of physical methods such as with debridement of a wound or infected tissue.

In the treatment of an infectious disease condition, an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level can be about 0.01 to 250 mg/kg per day, about 0.05 to 100 mg/kg per day, or about 0.1 to 50 mg/kg per day. Within this range the dosage can be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds can be administered on a regimen of 1 to 4 times per day, preferably once or twice per day. This dosage regimen can be adjusted to provide the optimal therapeutic response. It will be understood, however, that the specific dose level and frequency of dosage for any particular patient can be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Thus, in one aspect, the disclosure relates to methods for treating a bacterial infection in at least one cell, comprising the step of contacting the at least one cell with at least one compound of the disclosure, in an amount effective to alter the response in the at least one cell. In a further aspect, the cell is mammalian, for example human. In a further aspect, the cell has been isolated from a subject prior to the contacting step. In a further aspect, contacting is via administration to a subject.

Infectious diseases treatable by the presently disclosed APBA therapeutic peptides can be caused by a variety of bacteria and protozoa. In some embodiments, the infection is a bacterial infection. Exemplary microbial infections that can be treated by the method of the presently disclosed APBA therapeutic peptides include, but are not limited to, infections caused by *Staphylococcus aureaus, Enterococcus faecalis, Bacillus anthracis*, a *Streptococcus* species (e.g., *Streptococcus pyogenes* and *Streptococcus pneumoniae*), *Escherichia coli, Pseudomonas aeruginosa, Burkholderia cepacia*, a *Proteus* species (e.g., *Proteus mirabilis* and *Proteus vulgaris*), *Klebsiella pneumoniae, Acinetobacter baumannii, Strenotrophomonas maltophillia, Mycobacterium tuberculosis, Mycobacterium bovis*, other mycobacteria of the tuberculosis complex, and non-tuberculous mycobacteria, including *Mycobacterium ulcerans, Mycobacterium avium* and *Mycobacterium abscessus.*

An infectious disease that is associated world-wide with a high level of morbidity and mortality is a mycobaterial infection. Mycobacterial infections can cause different diseases such as tuberculosis ("TB"). Additionally, mycobacterial diseases can cause overwhelming, disseminated disease in immunocompromised patients and is the leading killer of people who are HIV infected. In spite of the efforts of numerous health organizations worldwide, the eradication of mycobacterial diseases has never been achieved, nor is eradication imminent. Based on currently available data, about one fourth of the world's population is infected with TB (CDC data; see https://www.cdc.gov/tb/statistics/default.htm; accessed on Oct. 10, 2018). Moreover, in 2016, 10.4 million people around the world became sick with TB disease and there were 1.7 million TB-related deaths worldwide (CDC data op. cit.).

Although over 37 species of *Mycobacterium* have been identified, more than 95% of all human infections are caused by seven species of mycobacteria: *M. tuberculosis, M. avium intracellulare, M. abscessus, M. kansasii, M. fortuitum, M. chelonae*, and *M. leprae*. Cases of human tuberculosis are predominantly caused by mycobacterial species comprising *M. tuberculosis, M. bovis*, or *M. africanum*. Infection is typically initiated by the inhalation of infectious particles, which are able to reach the terminal pathways in the lungs. Following engulfment by alveolar macrophages, the bacilli are able to replicate freely, with eventual destruction of the phagocytic cells. A cascade effect ensues wherein destruction of the phagocytic cells causes additional macrophages and lymphocytes to migrate to the site of infection, where they too are ultimately eliminated.

Mycobacteria can be classified into several major groups for purpose of diagnosis and treatment: *M. tuberculosis* complex (MTBC), which can cause tuberculosis (*M. tuberculosis, M. bovis, M. africanum*, and *M. microti*); *M. leprae*, which causes Hansen's disease or leprosy; and Nontuberculous mycobacteria (NTM) are all the other mycobacteria, which can cause pulmonary disease resembling tuberculosis, lymphadenitis, skin disease, or disseminated disease. MTBC members are causative agents of human and animal tuberculosis. Species in this complex include: *M. tuberculosis*, the major cause of human tuberculosis, *M. bovis, M. bovis* BCG, *M. africanum, M. canetti, M. caprae, M. microti*, and *M. pinnipedii.*

In a further aspect, the present disclosure provides methods of treating a mycobacterial infections, including those caused by mycobacteria such as *M. tuberculosis, M. bovis, M. bovis* BCG, *M. africanum, M. canetti, M. caprae, M. microti, M. pinnipedii, M. avium, M. avium paratuberculosis, M. avium silvaticum, M. avium "homninissuis", M. colombiense, M. asiaticum, M. gordonae, M. gastri, M. kansasii, M. hiberniae, M. nonchromogenicum, M. terrae, M. triviale, M. ulcerans, M. pseudoshottsii, M. shottsii, M. triplex, M. genavense, M. florentinum, M. lentiflavum, M. palustre, M. kubicae, M. parascrofulaceum, M. heidelbergense, M. interjectum, M. simiae, M. branderi, M. cookii, M. celatum, M. bohemicum, M. haemophilum, M. malmoense, M. szulgai, M. leprae, M. lepraemurium, M. lepromatosis, M. botniense, M. chimaera, M. conspicuum, M. doricum, M. farcinogenes, M. heckeshornense, M. intracellulare, M. lacus, M. marinum, M. monacense, M. montefiorense, M. murale, M. nebraskense, M. saskatchewanense, M. scrofulaceum, M. shimoidei, M. tusciae, M. xenopi, M. intermedium, M. abscessus, M. chelonae, M. bolletii, M. fortuitum, M. fortuitum subsp. acetamidolyticum, M. boenickei, M. peregrinum, M. porcinum, M. senegalense, M. septicum, M. new orleansense, M. houstonense, M. mucogenicum, M. mageritense, M. brisbanense, M. cosmeticum, M. parafortuitum, M. austroafricanum, M. diernhoferi, M. hodleri, M. neoaurum, M. frederiksbergense, M. aurum, M. vaccae, M. chitae, M. fallax, M. confluentis, M. flavescens, M. madagascariense, M. phlei, M. smnegmatis, M. goodii, M. wolinskyi, M. thermoresistibile, M. gadium, M. komossense, M. obuense, M. sphagni, M. agri, M. aichiense, M. alvei, M. arupense, M. brumae, M. canariasense, M. chubuense, M. conceptionense, M. duvalii, M. elephantis, M. gilvum, M. hassiacum, M. holsaticum, M. immunogenum, M. massiliense, M. moriokaense, M. psychrotolerans, M. pyrenivorans, M. vanbaalenii, M. pulveris, M. arosiense, M. aubagnense, M. caprae, M. chlorophenolicum, M. fluoroanthenivorans, M. kumamotonense, M. novocastrense, M. parmense, M. phocaicum, M. poriferae, M. rhodesiae, M. seoulense*, and *M. tokaiense.*

In a further aspect, the present disclosure provides methods of treating an infectious disease such as a mycobacterial infection. In various aspects, the mycobacterial infection can be associated with a *Mycobacterium tuberculosis* infection. In a still further aspect, the *Mycobacterium tuberculosis* infection is associated with infection by an MDR strain of *Mycobacterium tuberculosis*. In a yet further aspect, the *Mycobacterium tuberculosis* infection is associated with infection by an XDR strain of *Mycobacterium tuberculosis.*

In a further aspect, the present disclosure provides methods of treating an infectious disease such as a Gram positive bacterial infection. In a still further aspect, the Gram positive bacteria is selected from *Bacillus* sp. *Clostridium* sp., *Corynebacterium* sp, *Enterococcus* sp., *Mycoplasma* sp., *Staphylococcus* sp., and *Streptococcus* sp. In yet a further aspect, the Gram positive bacteria is vancomycin resistant *Enterococcus* sp. (VRE). In an even further aspect, the Gram positive bacteria is methicillin resistant *Staphylococcus* sp. (MRS). In a still further aspect, the Gram positive bacteria is selected from *Bacillus anthracis, Bacillus cereus, Bacillus subtilis, Clostridium difficile, Clostridium tetani, Clostridium botulinum, Clostridium perfringens, Corynebacterium diphtheria, Enterococcus faecalis, Enterococcus faecium, Listeria monocytogenes, Listeria ivanovii, Micrococcus luteus, Mycoplasma genitalium, Mycoplasma pneumoniae, Staphylococcus aureus, Staphylococcus epidermidis, Staphylococcus saprophyticus, Staphylococcus hyicus, Staphylococcus intermedius, Streptococcus pneumoniae*, and *Streptococcus pyogenes*. In yet a further aspect, the Gram positive bacteria is selected from *Bacillus anthracis, Bacillus subtilis, Enterococcus faecalis, Staphylococcus aureus, Streptococcus pneumoniae*, and *Streptococcus pyogenes*. In an even further aspect, the Gram positive bacteria is selected from vancomycin resistant *Enterococcus faecalis*, vancomycin resistant methicillin resistant *Enterococcus faecium, Staphylococcus aureus* (MRSA), methicillin resistant *Staphylococcus epidermidis* (MRSE), macrolide resistant *Streptococcus pneumoniae* (Mac-R SPN) and penicillin resistant *Streptococcus pneumonia* (PRSP).

In a further aspect, the present disclosure provides methods of treating an infectious disease such as a Gram negative bacterial infection. In a still further aspect, the Gram negative bacteria is selected from *Acinetobacter* sp., *Aeromonas* sp., *Burkholderia* sp., *Bordetella* sp., *Citrobacter* sp., *Chlamydia* sp., *Enterobacter* sp., *Escherichia* sp., *Francisella* sp., *Haemophilus* sp., *Klebsiella* sp., *Legionella* sp., *Moraxella* sp., *Neisseria* sp., *Proteus* sp., *Pseudomonas* sp., *Rickettsia* sp., *Salmonella* sp., *Shigella* sp., *Stenotrophomonas* sp., *Vibrio* sp., and *Yersinia* sp. In yet a further aspect, the Gram negative bacteria is selected from *Acinetobacter baumannii, Aeromonas hydrophila, Bordetella pertussis, Bordetella parapertussis, Bordetella bronchiseptica, Burkholderia cepacia, Citrobacter freundii, Chlamydia pneumoniae, Chlamydia trachomatis, Chlamydia psittaci, Enterobacter aerogenes, Enterobacter cloacae, Enterobacter sakazakii, Escherichia coli, Francisella tularensis, Haemophilus influenzae, Haemophilus aegypticus, Haemophilus ducreyi, Klebsiella edwardsii, Klebsiella pneumoniae, Legionella pneumophilia, Moraxella catarrhalis, Neisseria meningitidis, Neisseria gonorrhoeae, Proteus mirabilis, Proteus vulgaris, Pseudomonas aeruginosa, Rickettsia rickettsii, Rickettsia akari, Rickettsia conorrii, Rickettsia sibirica, Rickettsia australis, Rickettsia felis, Rickettsia japonica, Rickettsia africae, Rickettsia prowazekii, Rickettsia typhi, Salmonella enterica, Shigella boydii, Shigella dysenteriae, Shigella flexneri, Shigella sonnei, Stenotrophomonas maltophilia, Vibrio cholerae, Vibrio parahaemolyticus, Vibrio vulnificus, Vibrio fluvialis, Yersinia pestis, Yersina enterocolitica*, and *Yersina pseudotuberculosis*.

In a further aspect, the Gram negative bacteria is a multi-drug resistant Gram negative bacteria strain (MDR-GNB). In a still further aspect, the multi-drug resistant Gram negative bacteria strain (MDR-GNB) is resistant to at least one anti-microbial agent selected from amikacin, tobramycin, cefepime, ceftazidime, imipenem, meropenem, piperacillin-tazobactam, ciprofloxacin, levofloxacin, tigecycline, and polymyxin B. In yet a further aspect, the multi-drug resistant Gram negative bacteria strain (MDR-GNB) is selected from *Acinetobacter* sp., *Enterobacter* sp., *Klebsiella* sp., and *Pseuodomonas* sp. In an even further aspect, the multi-drug resistant Gram negative bacteria strain (MDR-GNB) is selected from *Acinetobacter baumannii, Enterobacter aerogenes, Klebsiella pneumoniae*, and *Pseudomonas aeruginosa*. In a still further aspect, the multi-drug resistant Gram negative bacteria strain (MDR-GNB) is *Enterobacter* sp.

In a further aspect, the present disclosure provides methods of treating an infectious disease selected from atypical pneumonia, bacterial meningitis, bronchitis, cholera, dental infection, dermatitis, diarrhea, diphtheria, dysentery, ear infection, endocarditis, gastritis, gastroenteritis, genital infection, genitourinary infection, infection associated with an indwelling device, intestinal infection, leprosy, listeriosis, lung infection, nocosomial infection, ocular infection, oral infection, otitis, osteo-articular infection, osteomyelitis, pharyngitis, papules, pharyngitis, pneumonia, pneumonia conjunctivitis, pruritius, pustules, pyoderma, pyothorax, respiratory infection, *Salmonellosis*, septicemia, sexually transmitted disease, sinusitis, skin infection, skin and soft tissue infection ("SSTI"), soft tissue infection, tetanus, tuberculosis, typhus, ulcer, urinary tract infection, and wound infection. In a still further aspect, the infectious disease is selected from endocarditits, osteomyelitis, skin and soft tissue infection ("SSTI"), and infection associated with an indwelling device. In yet a further aspect, the infectious disease is endocarditits. In an even further aspect, the infectious disease is osteomyelitis. In a still further aspect, the infectious disease is an SSTI. In yet a further aspect, the SSTI is a complicated SSTI (cSSTI). In an even further aspect, the infectious disease is associated with an indwelling device.

In a further aspect, the present disclosure provides methods of treating an infectious disease such in a human subject comprising administering a disclosed compound or a disclosed pharmaceutical composition, and further comprising administering to the human subject a therapeutically effective amount of a second active agent. In a still further aspect, the second active agent comprises at least one antibacterial agent. In yet a further aspect, the antibacterial agent comprises a compound selected from amoxicillin, ampicillin, azithromycin, aztreonam, azlocillin, bacitracin, carbenicillin, cefaclor, cefadroxil, cefamandole, cefazolin, cephalexin, cefdinir, cefditorin, cefepime, cefixime, cefoperazone, cefotaxime, cefoxitin, cefpodoxime, cefprozil, ceftazidime, ceftibuten, ceftizoxime, ceftriaxone, cefuroxime, chloramphenicol, cilastin, ciprofloxacin, clarithromycin, clavulanic acid, clinafloxacin, clindamycin, clofazimine, cloxacillin, colistin, cycloserin, dalbavancin, dalfopristin, demeclocycline, dicloxacillin, dirithromycin, doxycycline, erythromycin, enrofloxacin, enoxacin, enviomycin, ertepenem, ethambutol, ethionmide, flucloxacillin, fosfomycin, furazolidone, gatifloxacin, gentamicin, imipenem, isoniazid, kanamycin, levofloxacin, linezolid, lomefloxacin, loracarbef, mafenide, moxifloxacin, meropenem, metronidazole, mezlocillin, minocycline, mupirocin, nafcillin, nalidixic acid, neomycin, netilmicin, nitrofurantoin, norfloxacin, ofloxacin, oritavancin, oxytetracycline, penicillin, piperacillin, platensimycin, polymixin B, pyrazinamide, quinupristin, retapamulin, rifabutin, rifampin, rifapentine, roxithromycin, sparfloxacin, spectinomycin, sulbactam, sulfacetamide, sulfamethizole, sulfamethoxazole, teicoplanin, telithromycin, telavancin, temafloxacin, tetracycline, thioacetazone, thioridazine, ticarcillin, tinidazole, tobramycin, torezolid, tosufloxacin, trimethoprim, troleandomycin, trovafloxacin, and vancomycin, or combinations thereof.

In a further aspect, the present disclosure provides methods of treating an infectious disease such in a human subject comprising administering a disclosed compound or a disclosed pharmaceutical composition, and further comprising administering to the human subject a therapeutically effective amount of an anti-tuberculosis agent. In a still further aspect, the anti-tuberculosis agent is selected from amikacin, amoxicillin-clavulanic acid, bedaquiline, capreomycin, ciprofloxacin, clarithromycin, clofazimine, cycloserine, ethambutol, ethionamide, gatifloxacin, imipenem, isoniazid, kanamycin, levofloxacin, meropenem, moxifloxacin, ofloxacin, OPC-7683, para-aminosalicylic acid, pretomanid, pyrazinamide, rifampin, rifapentine, rifabutin, SQ109, streptomycin, sudoterb, terizidone, thiacetazone, viomycin, and combinations thereof. In a yet further aspect, the anti-tuberculosis agent is an aminoglycoside antibiotic, such as kanamycin A, amikacin, tobramycin, dibekacin, gentamicin, sisomicin, netilmicin, neomycin B, neomycin C, paromomycin and streptomycin. In an even further aspect, the anti-tuberculosis agent is a fluroquinolone, such as moxifloxacin, levofloxacin, sparfloxacin, nalidixic acid, ciprofloxacin, cinoxacin, oxolinic acid, piromidic acid, pipemidic acid, rosoxacin, enoxacin, fleroxacin, lomefloxacin, nadifloxacin, norfloxacin, ofloxacin, perfloxacin, rufloxacin, balofloxacin, grepafloxacin, pazufloxacin, temafloxacin, tosufloxacin, clinafloxacin, gatlifloxacin, sitafloxacin, prulifloxacin, delafloxacin, JNJ-Q2, nemofloxacin, danofloxacin, difloxacin, enrofloxacin, ibafloxacin, marbofloxacin, orbifloxacin, sarafloxacin and trovafloxacin. In a still further aspect, the anti-tuberculosis agent is a nitroimidazole antibiotic, such as metronidazole, tinidazole and nimorazole.

In a further aspect, the present disclosure provides methods of treating an infectious disease such in a human subject comprising administering a disclosed compound or a disclosed pharmaceutical composition, and further comprising administering to the human subject a therapeutically effective amount of an immunomodulatory agent. In a still further aspect, the immunomodulatory agent is a cytokine, an interleukin, a chemokine, or combinations thereof. In a yet further aspect, the immunomodulatory agent is selected from IL-2, IL-7 and IL-12, IFN-α, IFN-β, IFN-ε, IFN-κ, IFN-ω, IFN-γ, IFN-γ 1b, CCL3, CCL26, CXCL7, and combinations thereof.

In a further aspect, the administering is co-administering of the disclosed compound and the antibacterial agent. In a still further aspect, the co-administration is administration in a substantially simultaneous manner of the disclosed compound and the antibacterial agent. In yet a further aspect, the co-administration is administration in a substantially sequential manner of the disclosed compound and the antibacterial agent.

In a further aspect, the administration in a substantially simultaneous manner comprises a single dose form containing a fixed ratio of the compound and the antibacterial agent. In a still further aspect, the single dose form is a capsule or a tablet. In yet a further aspect, the single dose form is an ampule for a single intravenous administration.

In various aspects, the disclosed APBA therapeutic peptides can have a mechanism of antimicrobial action and/or may bind to and/or inhibit one or more bacterial target molecules or macromolecular complexes containing a bacterial target molecule. Mechanisms of action may include inhibiting or interfering with a biological or biochemical pathway of the bacterium. Exemplary pathways include, but are not limited to, protein synthesis, cell wall synthesis, DNA replication, transcription, and cell division. It will be appreciated that biological and biochemical pathways are not mutually exclusive and that some biological or biochemical pathways may be considered to be subsets or sub-pathways of other biological or biochemical pathways. Mechanisms of action include, but are not limited to, inhibiting protein synthesis (e.g., by binding ribosomal RNA or proteins, blocking tRNA binding to the ribosome-mRNA complex, inhibiting peptidyl transferase), inhibiting or interfering with synthesis of a cell wall component (e.g., inhibition of peptidoglycan synthesis, disruption of peptidoglycan cross-linkage, disruption of movement of peptidoglycan precursors, disruption of mycolic acid or arabinoglycan synthesis), cell membrane disruption, inhibiting or interfering with nucleic acid synthesis of processing, acting as "antimetabolites" and either inhibiting an essential bacterial enzyme or competing with a substrate of an essential bacterial enzyme, inhibiting or interfering with cell division.

Molecules, or macromolecular complexes containing them, that may be targets for antibiotics include, but are not limited to, peptidoglycans, penicillin binding proteins, lipopolysaccharides, ribosomes or ribosomal subunits or RNA or protein components thereof (23 S rRNA, 16S rRNA, proteins of the 30S or 50S subunit), DNA-dependent DNA polymerase, DNA-dependent RNA polymerase, microbial type I topoisomerase, microbial type II topoisomerase (e.g., topoisomerase IV or gyrase), enzymes involved in cell division such as FtsZ, etc.

In various aspects, the disclosed APBA therapeutic peptides inhibit bacterial protein synthesis. The bacterial species may be of any one or more types, e.g., gram-negative bacteria, gram-positive bacteria, atypical bacteria, and/or acid fast bacteria. Suitable organisms can include, but are not limited to members of the following genuses: *Actinomyces, Staphylococcus, Streptococcus, Enterococcus, Erysipelothrix, Neisseria, Branhamella, Listeria, Bacillus, Corynbacterium, Erysipelothrix, Gardnerella, Mycobacterium, Nocardia, Enterobacteriaceae, Escherichia, Salmonella, Shigella, Yersinia, Enterobacter, Klebsiella, Citrobacter, Serratia, Providencia, Proteus, Morganella, Edwardsiella, Erwinia, Vibrio, Aeromonas, Helicobacter, Campylobacter, Eikenella, Pasteurella, Pseudomonas, Burkholderia, Stenotrophomonas, Acinetobacter, Ralstonia, Alcaligenes, Moraxella, Mycoplasma, Legionella, Francisella, Brucella, Haemophilus, Bordetella, Clostridium, Bacteroides, Porphyromonas, Prevotella, Fusobacterium, Borrelia, Chlamydia, Rickettsia, Ehrlichia, Bartonella, Trichomonas*, and *Treponema*.

In various aspects of the disclosure the bacteria are species that are causative agents of disease in humans and/or animals. Examples include, but are not limited to, *Acinetobacter baumannii, Aeromonas hydrophila, Bacillus anthracis, Bacillus anthracis sterne, Bacillus subtilis, Burkholderia cepacia, Escherichia coli, Enterobacter cloacae, Enterococcus faecalis, Francisella tularensis, Campylobacter jejuni, Haemophilus influenzae, Klebsiella pneumoniae, Klebsiella oxytoca, Legionella pneumophila, Pasteurella multocida, Proteus mirabilis, Proteus vulgaris, Mycobacterium tuberculosis, Morganella morganii, Helicobacter pylori, Neisseria meningitides, Neisseria gonorrhoeae, Chlamydia trachomatis, Pseudomonas aeruginosa, Salmonella enterica, Salmonella typhimurium, Staphylococcus aureus, Staphylococcus epidermidis, Streptococcus pneumoniae, Streptococcus pyogenes, Strenotrophomonas maltophilia, Streptococcus agalactiae*, and *Yersinia pestis*.

Manufacture of a Medicament

In various aspects, the present disclosure pertains to uses of a disclosed APBA therapeutic peptide, or a pharmaceutically acceptable salt thereof, in the manufacture of a medicament with a pharmaceutically acceptable carrier or diluent for the treatment of a disorder associated with a microbial infection in a mammal, e.g., a human. In a further aspect, the present disclosure pertains to methods for the manufacture of a medicament to treat an infection associated with an antibiotic resistant microbe comprising combining at least one disclosed compound, or a pharmaceutically acceptable salt thereof in the manufacture of a medicament with a pharmaceutically acceptable carrier or diluent.

In one aspect, the disclosure relates to a medicament comprising one or more disclosed APBA therapeutic peptides; or a pharmaceutically acceptable salt, hydrate, solvate, or polymorph thereof.

In various aspect, the disclosure relates methods for the manufacture of a medicament for the treatment of a disorder associated with a microbial infection in a mammal (e.g., treatment of one or more bacterial infections) in mammals (e.g., humans) comprising combining one or more disclosed APBA therapeutic peptides, or a pharmaceutically acceptable salt, solvate, hydrate, or polymorph thereof, and at least one additional therapeutic agent with a pharmaceutically acceptable carrier.

Kits

In a further aspect, the present disclosure relates to kits comprising at least one disclosed compound, or a pharmaceutically acceptable salt, hydrate, solvate, or polymorph thereof, and one or more of: (a) at least one agent known to treat a disorder associated with a microbial infection; or (b) instructions for treating a disorder associated with a microbial infection.

The disclosed APBA therapeutic peptides and/or pharmaceutical compositions comprising the disclosed APBA therapeutic peptides can conveniently be presented as a kit, whereby two or more components, which may be active or inactive ingredients, carriers, diluents, and the like, are provided with instructions for preparation of the actual dosage form by the patient or person administering the drug to the patient. Such kits may be provided with all necessary materials and ingredients contained therein, or they may contain instructions for using or making materials or components that must be obtained independently by the patient or person administering the drug to the patient. In further aspects, a kit can include optional components that aid in the administration of the unit dose to patients, such as vials for reconstituting powder forms, syringes for injection, customized IV delivery systems, inhalers, etc. Additionally, a kit can contain instructions for preparation and administration of the compositions. The kit can be manufactured as a single use unit dose for one patient, multiple uses for a particular patient (at a constant dose or in which the individual compounds may vary in potency as therapy progresses); or the kit may contain multiple doses suitable for administration to multiple patients ("bulk packaging"). The kit components may be assembled in cartons, blister packs, bottles, tubes, and the like.

In a further aspect, the disclosed kits can be packaged in a daily dosing regimen (e.g., packaged on cards, packaged with dosing cards, packaged on blisters or blow-molded plastics, etc.). Such packaging promotes products and increases patient compliance with drug regimens. Such packaging can also reduce patient confusion. The present invention also features such kits further containing instructions for use.

In a further aspect, the present disclosure also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration.

In various aspects, the disclosed kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

It is contemplated that the disclosed kits can be used in connection with the disclosed methods of making, the disclosed methods of using or treating, and/or the disclosed compositions.

Research Tools

The disclosed APBA therapeutic peptides and pharmaceutical compositions have activity as anti-microbial therapeutic agents. As such, the disclosed APBA therapeutic peptides are also useful as research tools. Accordingly, one aspect of the present disclosure relates to a method of using a disclosed APBA therapeutic peptide as a research tool, the method comprising conducting a biological assay using a disclosed APBA therapeutic peptide in an anti-microbial assay and determining microbial growth. Accordingly, disclosed APBA therapeutic peptides can also be used to evaluate new chemical compounds. Thus another aspect of the invention relates to a method of evaluating a test compound in a biological assay, comprising: (a) conducting a biological assay with a test compound to provide a first assay value; (b) conducting the biological assay with a disclosed APBA therapeutic peptide to provide a second assay value; wherein step (a) is conducted either before, after or concurrently with step (b); and (c) comparing the first assay value from step (a) with the second assay value from step (b). Still another aspect of the invention relates to a method of studying a biological system, e.g., a model animal for a clinical condition, the method comprising: (a) contacting the biological system with a disclosed APBA therapeutic peptide; and (b) determining the effects caused by the compound on the biological system or sample.

Without further elaboration, it is believed that one skilled in the art can, based on the above description, utilize the present disclosure to its fullest extent. The following specific embodiments and examples are, therefore, to be construed as merely illustrative, and not limitative of the remainder of the disclosure in any way whatsoever.

EXAMPLES

The following examples are provided to illustrate embodiments of the present invention but are by no means intended to limit its scope.

The examples described herein will be understood by one of ordinary skill in the art as exemplary protocols. One of ordinary skill in the art will be able to modify the below procedures appropriately and as necessary.

Example 1

Methods and Experimental Procedures

Materials and Instrumentation

The Ph.D.™-C7C Phage Display Peptide Library Kit and the *E. coli* K12 ER2738 strain were purchased from New England Biolabs. All ER2738 cultures were grown in the presence of 20 μg/mL tetracycline. Chemical reagents for small molecule, library synthesis and confirmation and peptide synthesis were purchased from various vendors and used as received. The fluorescent gel was imaged on a BioRad ChemiDoc MP Imaging System. The *S. aureus*

(ATCC 6538) and MRSA (ATCC 43300) were purchased from Microbiologics as a lyophilized pellet. The wild-type *A. baumannii* (AB5075) is a virulent and multidrug resistant clinical isolate that has been established as a pathogenic model strain and the LOS deficient *A. baumannii* (5075 LOS−) was established from AB5075 through selection for colistin resistance. NMR data of the small molecule was collected on a VNMRS 500 MHz NMR spectrometer. Peptide synthesis was performed on a Tribute peptide synthesizer from Protein Technologies and purified via reverse-phase high performance liquid chromatography (RP-HPLC) on a Waters Prep LC with a Jupiter C18 Column (Phenomenex). Mass spectrometry data were generated using an Agilent 6230 LC TOF mass spectrometer. Fluorescence images were captured on a Zeiss Axio Observer A1 inverted microscope. Flow cytometry analysis was performed on a BD FACSAria cell sorter. Photoinactivation was performed with a X-Cite 120Q (120-Watt lamp) excitation light source accompanied with the Zeiss microscope. Jurkat T lymphocytes were a gift from the Johnson lab at Boston College, HEK293T cells were a gift from the Weerapana lab at Boston College, and mammalian cell cytotoxicity was evaluated on a SpectraMax M5 plate reader along with fluorescence anisotropy.

APBA-L& and Peptide Synthesis

Figure 7:
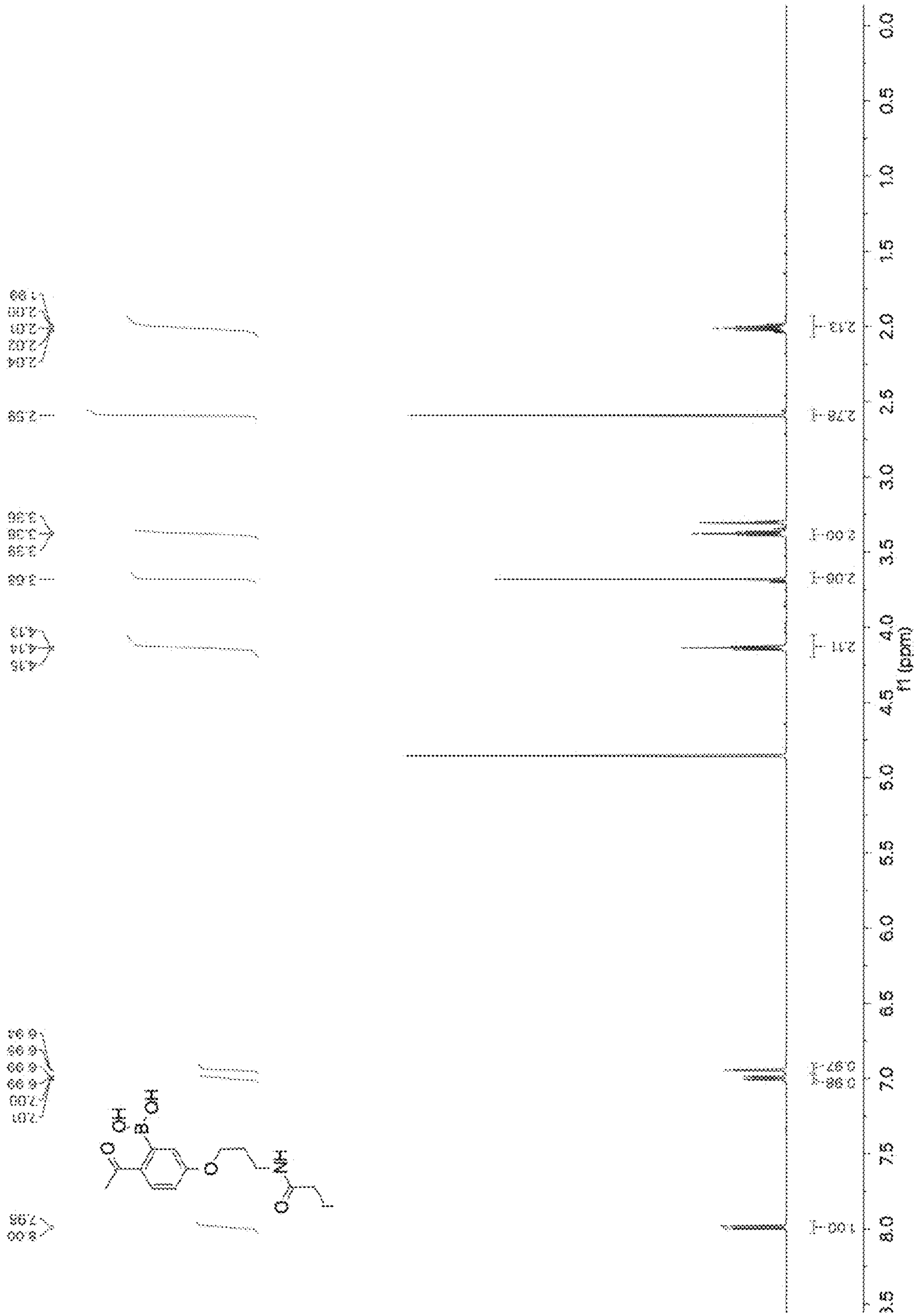
FIG. 7 shows the $^{1}$H-NMR of APBA-IA (5).
Figure 8:
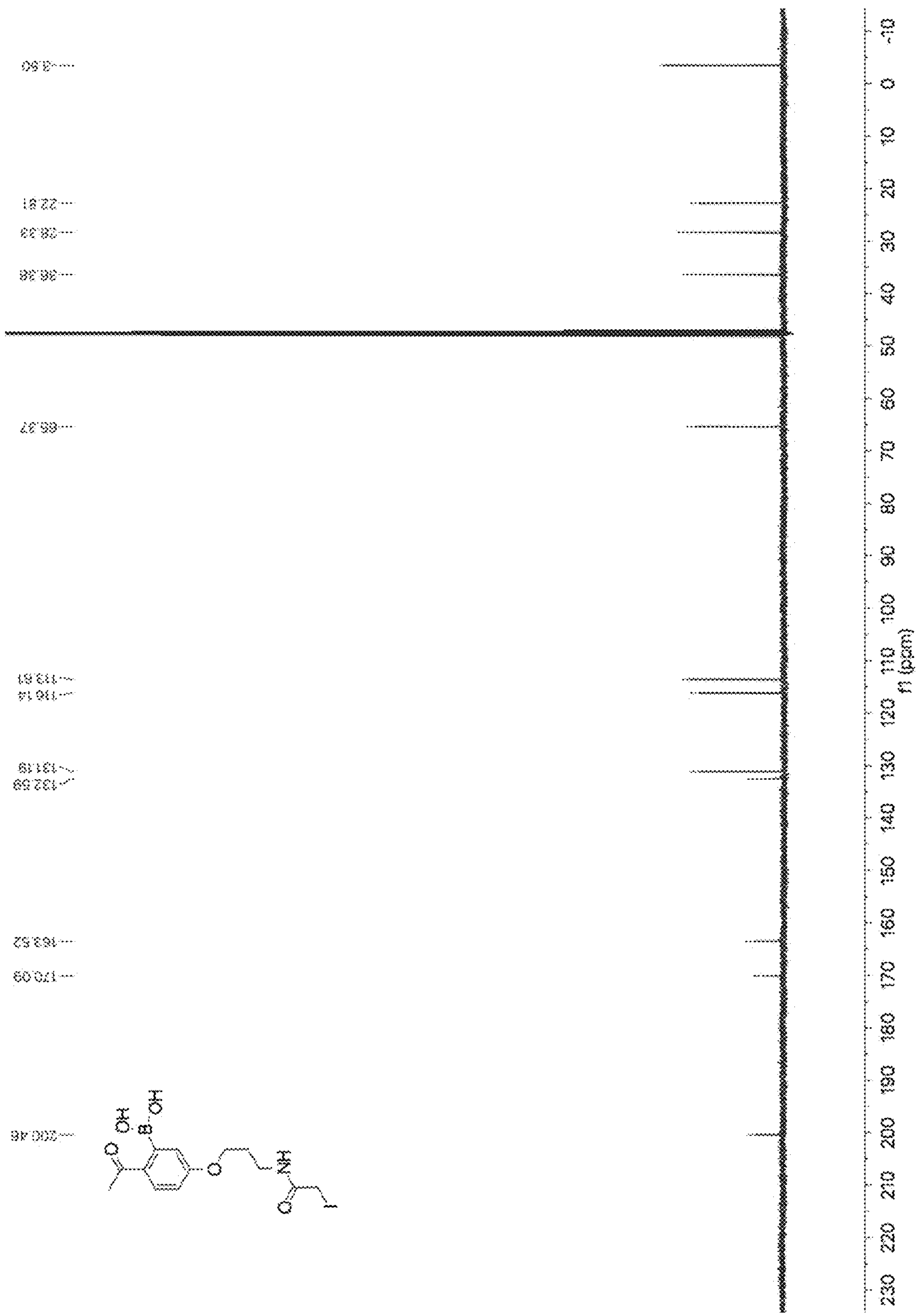
FIG. 8 shows $^{13}$C-NMR of APBA-IA (5).

Details of the small molecule synthetic route and peptide synthesis are provided in FIGS. 6-8 and in the description below.

APBA-Dimer Library Synthesis

The Ph.D.™-C7C Phage Display Peptide Library (5 μL, ~$1\times10^{13}$ pfu/mL) was subjected to reduction in the presence of iTCEP (25 μL), in a total volume of 200 μL in TBS (pH 8.5) for 48 hours at 4° C. APBA-IA (2 mM, 2 μL from a 200 mM DMSO stock) was added to the reduced phage and allowed to conjugate for 2 hours at room temperature. The labeled phage was removed from iTCEP and precipitated to remove excess labeling reagent with ⅙ volume 20% (w/v) PEG-8000, 2.5 M NaCl for 5 hours at 4° C. Precipitated phage was re-dissolved in PBS (pH 7.4, 100 μL) and the phage titer was calculated according to the M13 Titer Protocol provided by New England Biolabs.

Fluorescent Gel Analysis

APBA-IA and Biotin-IA labeled library phage (~$1\times10^{10}$ pfu/mL) were subjected to labeling with Scz-FITC (2 mM), synthesized previously, for 1 hour followed by precipitation. Phage samples were heat denatured at 95° C. for 5 minutes. Samples were subjected to 15% SDS-PAGE for 50 minutes, allowing the lower molecular weight PVIII protein to run off the gel, and imaged.

Panning Against Whole Cells

*S. aureus* was grown in LB medium to an $OD_{600}$~1.0 (~$1\times10^{9}$ cfu/mL). The cells (1 mL) were washed with chilled PBS containing 0.05% Tween (PBST) twice and resuspended in PBS (pH 7.4) with 10 mg/mL BSA present. The APBA-labeled phage library (~$1\times10^{10}$ pfu) was added to the cell suspension and allowed to incubate on ice for 1 hour. The cells were washed three times with PBST and three times with PBS to remove unbound phage. Cell-bound phage were incubated with 200 μL elution buffer (Glycine-HCl, pH 2.2, 1 mg/mL) for 15 minutes followed by centrifugation of the cells. The supernatant was removed and neutralized with 150 μL Tris-HCl (pH 9.1). All Eppendorf tubes utilized in the panning procedure were blocked with 10 mg/mL BSA before use. Centrifugation of cells was performed at 5,000 rcf for 5 minutes. The eluted bound phage solution was added to early-log phase ER2738 and amplified for 4.5 hours followed by precipitation to isolate the amplified phage. The amplified phage were labeled with APBA-IA and subjected to the next round of panning. The phage titer was calculated before and after each round of panning to determine the input and output population. Individual phage colonies from each round of panning were amplified in ER2738. Phage DNA was isolated using a Qiagen miniprep kit and sent for sequencing analysis by Eton Bioscience, Inc. The screens against *S. aureus* with the unmodified C7C library and the IA-alkylated library (C7C-IA) were performed following the same protocol. The C7C-IA library was prepared using the same protocol described for the APBA-dimer library preparation. The screen against *A. baumannii* (LOS−) was performed following the same protocol; however, a negative screen was introduced against *A. baumannii* (LOS+) starting in the second round. In the negative screen, the phage library was incubated with *A. baumannii* (LOS+) for 1 hour, the supernatant was removed and subsequently subjected to the positive screen against *A. baumannii* (LOS−).

Flow Cytometry Analysis

Figures 14A, 14B, 14C:
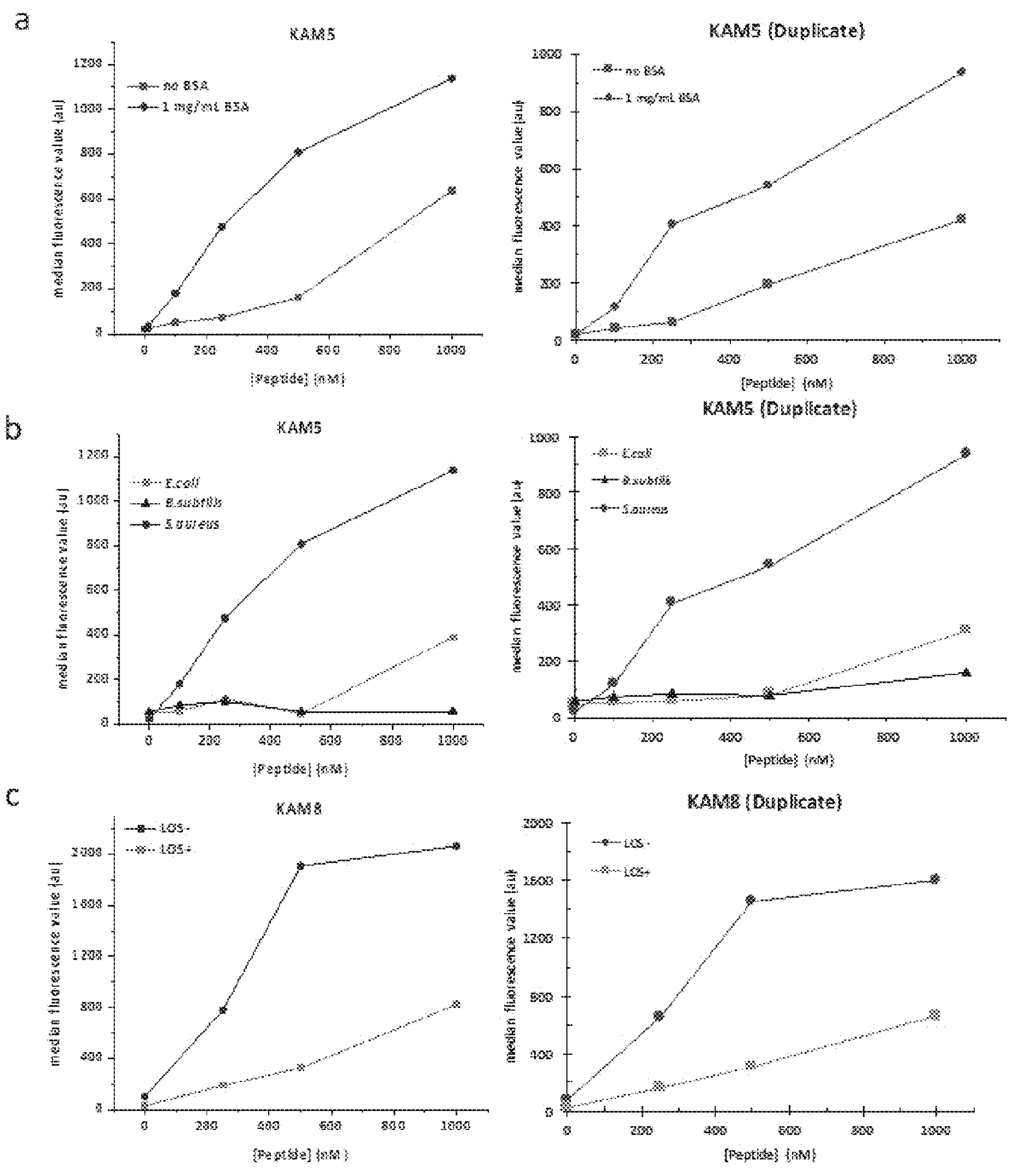
FIGS. 14A-14C show duplicate flow cytometry experiments demonstrating consistent results between trials. Data sets on the left are presented in the main text figures while their duplicate datasets are presented on the right. (A) *S. aureus* staining by KAM5 (FIG. 2B and Duplicate) (B) Bacterial species selectivity studies of KAM5 (FIG. 3A and Duplicate) (C) *A. baumannii* staining by KAM8 (FIG. 5A and Duplicate).

Each bacterial strain was grown to an $OD_{600}$~0.5, washed and diluted with PBS (pH 7.4). The cells (~$1\times10^{7}$ cfu/mL) were incubated with various concentrations of FAM-labeled peptide with or without BSA in PBS. After incubation for 1 hour, samples were subjected to cytometric analysis. Data obtained was analyzed via BD FACSDiva software and median fluorescent values were computed from the generated histograms. All flow cytometry experiments were repeated and generated consistent results (see FIG. 14).

Fluorescence Microscopy

Each bacterial strain was grown to an $OD_{600}$~1.0, washed and diluted with PBS (pH 7.4). The cells (~$1\times10^{9}$ cfu/mL) were incubated with various concentrations of TAMRA-labeled peptide with or without BSA in PBS for 1 hour. The same microscopy procedure described was implemented using filter set 20 HE (excitation: BP 546/12, emission: BP 607/80) suitable for detection of TAMRA fluorescence and images were processed consistently using ImageJ software.

Photoinactivation of Bacteria

Each bacterial strain was grown to an $OD_{600}$~0.7, washed and diluted with PBS (pH 7.4). The cells (~$1\times10^{8}$ cfu/mL) were incubated with eosin-conjugated peptides and various controls for 15 minutes. Half of the bacterial suspension was removed and placed in a 96-well plate (Corning 3595). The well was subjected to photoirradiation on the Zeiss microscope using the 20× objective and fluorescein filter to emit blue light for 15 minutes. Cells were diluted in LB media, spread on LB agar plates and incubated overnight at 37° C. The *A. baumannii* (LOS−) strain was spread on LB agar (+10 μg/mL polymyxin b) and incubated for 24 hours. The amount of cell killing was calculated by comparing the amount of colonies of treated bacteria to an untreated PBS control. All experiments were repeated and the average cell killing of two trials was plotted.

Example 2

Synthesis of APBA-L&

Figure 6:
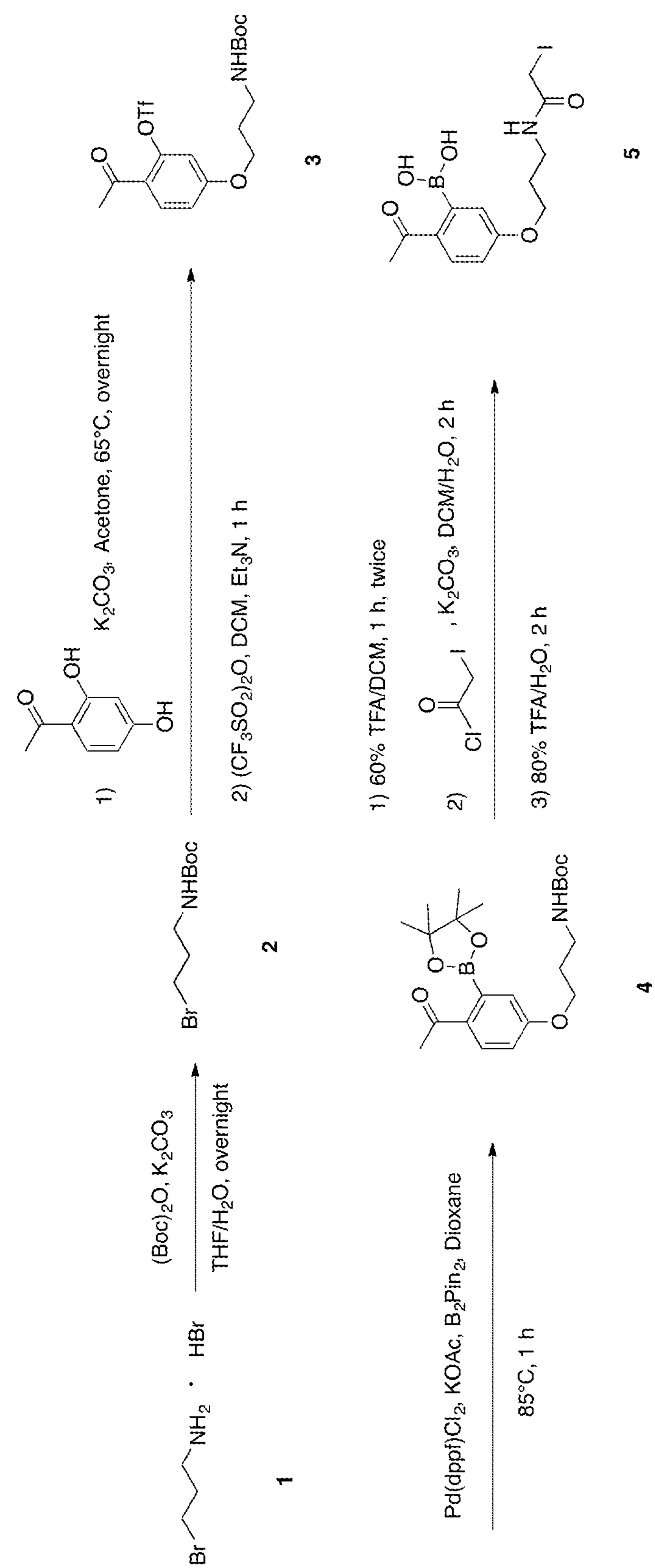
FIG. 6 shows the synthetic scheme of APBA-IA (5).

Synthesis of tert-butyl (3-bromopropyl)carbamate (2) (see FIG. 6)

3-Bromopropylamine hydrobromide (molecule 1 shown in FIG. 6, 7.00 g, 32.0 mmol) was dissolved in 60 mL 10% $Na_2CO_3$ solution and placed on ice for 5 min, to which Boc-anhydride (6.50 g, 29.8 mmol in 60 mL THF) was added. The reaction was kept at room temperature overnight.

THF in the reaction mixture was then evaporated. The residual solution was acidified to pH 3 by 1 N HCl and the product was extracted with EtOAc (3×150 mL). The organic layers were combined and washed with saturated brine (200 mL) and dried over sodium sulfate. Solvent removal yielded a white solid (6.40 g, 90% yield). $^1$H NMR (500 MHz, Chloroform-d) δ 4.79 (br, 1H), 3.40 (t, J=6.5 Hz, 2H), 3.22 (q, J=6.4 Hz, 2H), 2.01 (m, J=6.6 Hz, 2H), 1.39 (s, 9H). $^{13}$C NMR (126 MHz, Chloroform-d) δ 155.95, 79.29, 38.96, 32.70, 30.74, 28.34. MS-ESI$^+$: calculated for $C_4H_9BrNO_2$ $[M-^tBu+H]^+$ 181.9817, found 181.9795.

Synthesis of 2-acetyl-5-(3-((tert-butoxycarbonyl) amino)propoxy)phenyltrifluoro-methanesulfonoate (3) (see FIG. 6)

Molecule 2 (3.00 g, 12.6 mmol) and 2,4-Dihydroxyacetophenone (2.13 g, 14.0 mmol) (see FIG. 6) were dissolved in 30 mL of acetone. $K_2CO_3$ (7.74 g, 56.0 mmol) was added and the reaction was allowed to reflux at 65° C. overnight. Acetone was then evaporated and the residue was dissolved in 100 mL water. The product was extracted with EtOAC (3×100 mL). The organic layers were combined and washed with saturated brine (150 mL) and dried over sodium sulfate. Solvent removal yielded an off-white solid (3.78 g). 2.00 g of the crude product was directly dissolved in 40 mL dry DCM. Triethylamine (2.17 g, 21.5 mmol) was added to the solution and the mixture was kept at −78° C. for 5 min. Trifluoromethane sulfonic anhydride (3.52 g, 12.4 mmol) was added slowly during 5 min. The reaction was warmed up to room temperature and allowed to stir for 1 hr. The reaction was subsequently quenched with 40 mL saturated sodium bicarbonate. The mixture was stirred for 5 min and the product was extracted with DCM (3×100 mL). The combined organic layer was washed with brine (100 mL) and dried over sodium sulfate. The solvent was removed and the product was purified via silica gel column chromatography using EtOAc/Hexane (1:4) to give the desired product as a light orange solid (2.29 g, 78% yield over two steps). $^1$H NMR (600 MHz, Chloroform-d) δ 7.82 (d, J=8.7 Hz, 1H), 6.96-6.91 (dd, 1H), 6.80 (d, J=2.4 Hz, 1H), 4.71 (br, 1H), 4.08 (t, J=6.1 Hz, 2H), 3.32 (q, J=6.5 Hz, 2H), 2.58 (s, 3H), 2.01 (m, J=6.3 Hz, 2H), 1.43 (s, 9H). BC NMR (151 MHz, Chloroform-d) δ 195.12, 162.98, 156.13, 148.62, 132.86, 124.24, 119.82, 117.69, 113.82, 109.46, 79.60, 66.79, 37.68, 29.60, 29.26, 28.50. MS-ESI$^+$: calculated for $C_{13}H_{15}F_3NO_7S$ $[M-^tBu+H]^+$ 386.0521, found 386.0494.

Synthesis of tert-butyl (3-(4-acetyl-3-(4,4,5,5-tetramethyl-1,3,2-dioxaborolan-2-yl)phenoxyl) propyl)carbamate (4) (see FIG. 6)

Molecule 3 (1.00 g, 2.27 mmol), bis(pinacolato)diboron (1.40 g, 5.51 mmol), [1,1'-bis(diphenylphosphino)ferrocene] dichloropalladium(II) (0.20 g, 0.27 mmol) and potassium acetate (0.8 g, 8.16 mmol) (see FIG. 6) were dissolved in 20 mL of anhydrous dioxane, to which ~100 mg of 3 Å molecular sieves were added. The reaction was bubbled with argon for 15 min and allowed to stir for 1 hr at 85° C. The reaction was cooled down and 50 mL of water was added to the reaction. The product was extracted with EtOAc (3×100 mL). The combined organic layer was washed with brine (100 mL) and dried over sodium sulfate. The solvent was removed and the product was purified via silica gel column chromatography using EtOAc/Hexane (3:7) to give the desired product as a light yellow viscous liquid (0.81 g, 85% yield). $^1$H NMR (500 MHz, Chloroform-d) δ 7.69 (d, J=8.6 Hz, 1H), 6.88 (d, J=2.5 Hz, 1H), 6.77 (dd, J=8.6, 2.6 Hz, 1H), 4.91 (br, 1H), 3.98 (t, J=6.1 Hz, 2H), 3.21 (q, J=6.5 Hz, 2H), 2.46 (s, 3H), 1.89 (m, J=6.9 Hz, 2H), 1.36 (d, J=1.6 Hz, 21H). BC NMR (126 MHz, Chloroform-d) δ 198.26, 162.41, 155.99, 133.47, 130.68, 117.92, 113.83, 83.49, 83.48, 79.03, 65.80, 37.64, 29.39, 28.33, 24.86. MS-ESI$^+$: calculated for $C_{16}H_{23}BNO_5$ $[M-Pin-H_2O+H]^+$ 320.1669, found 320.1857.

Synthesis of (2-acetyl-5-(3-(2-iodoacetamido) propoxy)phenyl)boronic acid (5) (see FIG. 6)

Molecule 4 (250 mg, 0.60 mmol) was dissolved in 2 mL of DCM, to which was added 3 mL TFA (see FIG. 6). The reaction was stirred at room temperature for 1 hr. TFA and DCM were removed and the residue was treated with 60% TFA/DCM (5 mL) for another hour. After solvent removal, $K_2CO_3$ (500 mg, 2.89 mmol) was added to the residue. The mixture was dissolved in DCM/$H_2O$ (2:1, 6 mL) and kept on ice for 20 min. Iodoacetyl chloride (533 mg, 2.62 mmol) was added slowly during 5 min to the reaction. The mixture was allowed to stir at room temperature for 2 hr. The solution was acidified to pH 3 by 1 N HCl and the product was extracted with DCM (3×100 mL). The combined organic layer was washed with brine (100 mL) and dried over sodium sulfate. DCM was removed and the residue was treated with TFA/$H_2O$ for 2 h. After solvent removal, the crude material was re-dissolved in 10 mL Acetonitrile/H2O (2:3) solution and purified via RP-HPLC. The product is a white solid after lyophilization (85 mg, 35% yield over three steps). $^1$H NMR (500 MHz, Methanol-$d_4$) δ 7.99 (d, J=8.6 Hz, 1H), 7.00 (dd, J=8.6, 2.6 Hz, 1H), 6.94 (d, J=2.5 Hz, 1H), 4.14 (t, J=6.2 Hz, 2H), 3.68 (s, 2H), 3.38 (t, J=6.7 Hz, 2H), 2.59 (s, 3H), 2.01 (m, J=6.5 Hz, 2H). $^{13}$C NMR (126 MHz, Methanol-$d_4$) δ 200.46, 170.09, 163.52, 132.59, 131.19, 116.14, 113.61, 65.37, 36.38, 28.33, 22.81, -3.50. MS-ESI$^+$: calculated for $C_{13}H_{16}BINO_4$ $[M-H_2O+H]^+$ 388.0217, found 388.0473.

Example 3

General Methods for Pulse-Chase Confirmation and Phage-Binding Microscopy Pulse-Chase Confirmation of Phage Labeling Streptavidin agarose resin (25 μL/sample) was washed with PBS (pH 7.4) and blocked with 10 mg/mL BSA via incubation for 1 hour. APBA-IA labeled library was subjected to subsequent labeling with Biotin-IA (2 mM) for 2 hours followed by precipitation. Biotin-IA labeled and APBA-IA/Biotin-IA labeled phage (200 μL, ~$1\times10^{10}$ pfu/mL) were subjected to the streptavidin resin for 1 hour. Non-reduced and reduced phage, without small molecule labeling, were also analyzed. Unbound phage was removed from resin and the phage titer was calculated. The titer was compared to that of phage not subjected to streptavidin to generate a percent capture. The average percent capture and standard deviation of three trials was plotted. Wild-type phage, with no library insert, was subjected to the same analysis for comparison.

Phage-Binding Microscopy

For the screen against *S. aureus*, individual phage variants in which sequence repetition was observed were reduced and labeled with APBA-IA. *S. aureus* was grown to an $OD_{600}$~1.0, washed and diluted with PBS (pH 7.4). The cells (~$1\times10^9$ cfu/mL) were incubated with $10^6$, $10^8$ and $10^{10}$ pfu/mL of each labeled phage hit for 1 hour in the presence of 10 mg/mL BSA. Fluorescein labeled anti-M13 major coat protein antibody (1 μg, Santa Cruz Biotechnology) was added to the bacterial suspension, incubated for 30 minutes and directly subjected to fluorescence microscopy analysis. Antibody binding to *S. aureus*, with no phage present, was also analyzed to assess any background fluorescence. White light and fluorescent images were obtained on the Zeiss microscope equipped with filter set 44 (excitation: BP 475/40, emission: BP 530/50) suitable for detection of fluorescein fluorescence. Images were captured using the 100× oil immersion objective with a 500 ms exposure time. All images were processed consistently using ImageJ software.

Example 4

Peptide Synthesis and MTT Assay

Peptide Synthesis

Solid phase peptide synthesis was performed on a rink amide resin using Fmoc chemistry. An alloc-protected diaminopropionic acid residue was installed at the C-terminus for on-resin coupling of a fluorophore, followed by a triple glycine linker and the peptide hit sequence at the N-terminus. 5(6)-FAM, 5(6)-TAMRA and 5(6)-carboxyeosin were conjugated to the peptide on resin by first removing the alloc protecting group with tetrakis(triphenylphosphine) palladium(0) and phenylsilane in DCM followed by subsequent HBTU-mediated amide bond coupling in 0.4 M NMM/DMF. The peptides were cleaved off resin and globally deprotected with reagent B (88% TFA, 5% H2O, 2% triisopropylsilane, 5% phenol). Crude peptides were obtained via ether precipitation and purified by RP-HPLC. For cysteine alkylation, each peptide hit was treated with 3 equivalents of APBA-IA in the presence of TCEP (2 eq) in 2 M NMM/DMF for 3 hours and purified via RP-HPLC. All peptides were characterized with LC-MS to confirm their identities and excellent purities (>95%).

MTT Assay

Jurkat cells were cultured in RPMI 1640 (containing 10% FBS, 2 mM glutamine, 1% Penicillin/Streptomycin) and maintained at $5\times10^5$ cells/mL. Cells were diluted in RPMI and distributed to a 96-well plate (Corning 3595) at 50,000 cells/well (200 μL/well). 2 μL of a 100× DMSO solution of KAM5-Eosin (200 μM) and KAM8-Eosin (200 μM) was added to each well and incubated for 24 hours. A positive control for viability of DMSO treated cells along with a positive control for cytotoxicity of camptothecin at 50 μM (5 mM DMSO stock) were included. For photoirradiation, the cells were incubated with the compound of interest for 15 minutes, each well was irradiated for 15 minutes (see photoinactivation protocol-paragraph 0053) and the plate was returned to the incubator for the remainder of the 24 hour incubation. Cells were centrifuged for 5 minutes (180 rcf) and the supernatant culture medium was carefully removed. 100 μL of 3-(4,5-dimethylthiazol-2-yl)-2,5-diphenyltetrazolium bromide (MTT, 0.5 mg/mL in RPMI) was added to each well and incubated for 4 hours followed by the addition of 10% SDS in 0.01 M HCl (100 μL) and incubation overnight.

HEK293T cells were grown in complete DMEM (containing 10% FBS, 2 mM glutamine and 1% Penicillin/Streptomycin) to about 80% confluency in a 150 mm dish. Cells were removed from the plate with 0.25% trypsin protease solution (containing EDTA) at 37° C. for 5 minutes and pelleted (3,500 rpm, 5 minutes). Cells were diluted in DMEM, distributed to a 96-well plate (Corning 3595) at 30,000 cells/well (100 μL/well) and incubated for 24 hours to allow for cell adherence. 1 μL of 100× DMSO solutions were added to each well and incubations/photoirradiation were performed as described above. After 24 hours, the supernatant culture medium was carefully removed and the cells were incubated with 100 μL MTT (0.5 mg/mL in RPMI) for 4 hours followed by the addition of 10% SDS in 0.01 M HCl (100 μL) and incubation overnight.

All incubations were performed at 37° C. and 5% $CO_2$. Absorbance readings were measured at 570 nm and cell viability was normalized to the DMSO control as an average of three trials for non-irradiated samples and an average of two trials for photoirradiated samples with standard deviations.

Example 5

Modification of the C7C Library to Display APBA Warheads

The utilization of APBA to bind biological amines via reversible covalent conjugation to give iminoboronates has recently been demonstrated. In comparison to the corresponding imine, an iminoboronate exhibits much greater thermodynamic stability with typical $K_d$ values in the low millimolar range (1-10 mM). Despite the thermodynamic stabilization, the iminoboronate formation displays accelerated kinetics in both forward and backward directions, leading to quick equilibrium. This dynamic conjugation, analogous to hydrogen bonds, proves to be a powerful mechanism to promote ligand binding to biological targets. Specifically, the present invention shows that incorporating an APBA warhead into cationic peptides can yield selective probes of gram-positive bacteria, which readily label a target bacterium in serum via a combination of reversible covalent and noncovalent interactions. It is envisioned that introducing such reversible covalent warheads into phage libraries could give a versatile platform to allow discovery of specific probes for diverse bacterial species and strains.

Figure 1B:
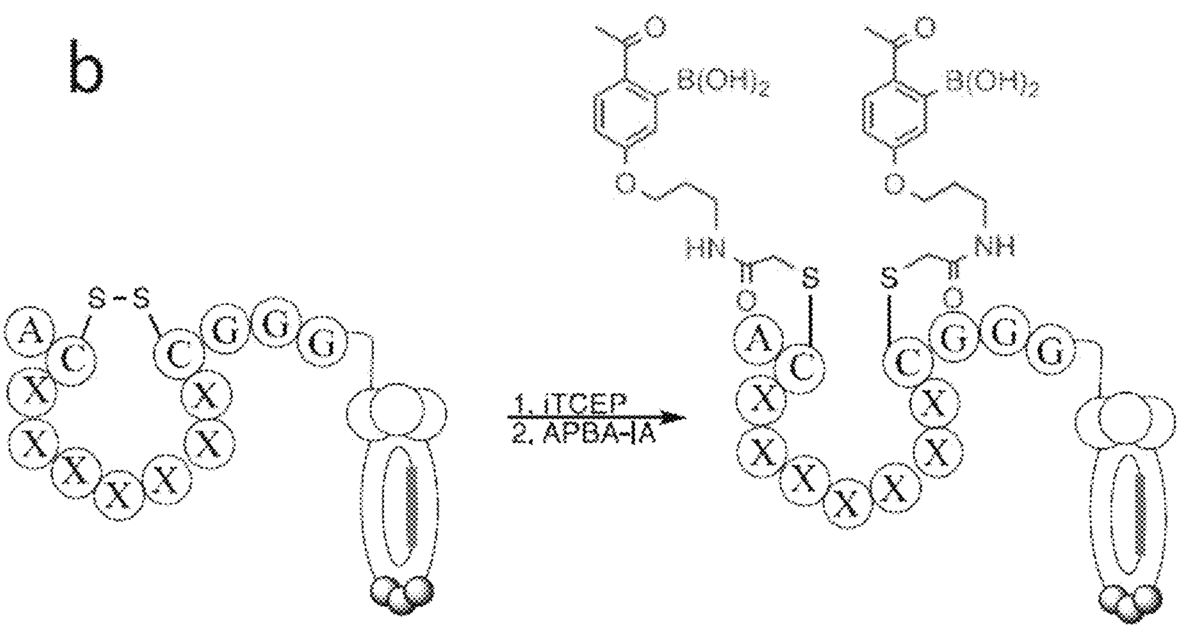
Figure 9:
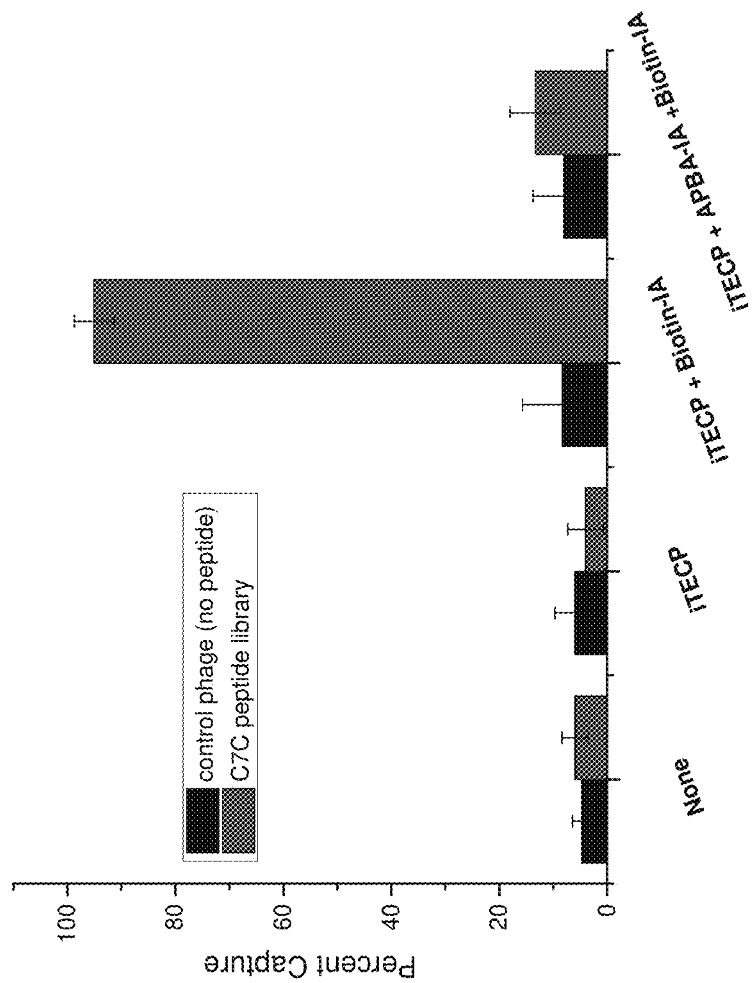
FIG. 9 shows pulse-chase confirmation of APBA-IA labeling on library phage.

The phage library chosen for modification was the commercially available Ph.D.-C7C library, which displays disulfide-cyclized peptides with seven randomized residues that are fused to the pIII minor coat protein of the M13 phage. The library was modified with APBA moieties via disulfide reduction and selective cysteine alkylation originally described by Derda and coworkers. Briefly, the disulfide bond of the C7C peptides was selectively reduced on phage with immobilized TCEP (iTCEP) for 48 hours at 4° C. The reduced cysteines were then alkylated with an APBA derivative, namely APBA-IA, for 2 hours to yield the APBA-dimer library (FIG. 1B). The details of APBA-IA synthesis can be found in FIGS. 6-8. The extent of APBA-IA labeling was monitored by a pulse-chase assay in which biotin-iodoacetamide (Biotin-IA) treatment and streptavidin capture after APBA-IA labeling allowed quantification of phage that APBA-IA failed to label. The minimal streptavidin capture of the APBA-IA treated phage indicates complete labeling of cysteines by APBA-IA (FIG. 9). More direct evidence of APBA conjugation was established by treating the modified phage with a fluorophore labeled semicarbazide (Scz-FITC, FIGS. 1C and 1D), which we recently reported to conjugate with APBA chemoselectively to form diazaborines. The labeled phage was heat denatured and the coat proteins were subjected to fluorescence gel electrophoresis analysis. Reduced phage with and without Biotin-IA labeling were included as negative controls to confirm on the APBA-semicarbazide conjugation. For the APBA labeled phage, a single distinct band was observed that corresponds to the pIII protein (FIG. 1D), which is known to run on SDS-PAGE with an apparent molecular weight of 60-65 kDa, larger than its actual molecular weight of 43 kDa. Notably, no fluorescent labeling of the pIII protein was observed for the negative controls as expected.

Example 6

Panning Against *S. aureus* with the APBA-Dimer Library

Figures 2A, 2B, 2C, 2D:
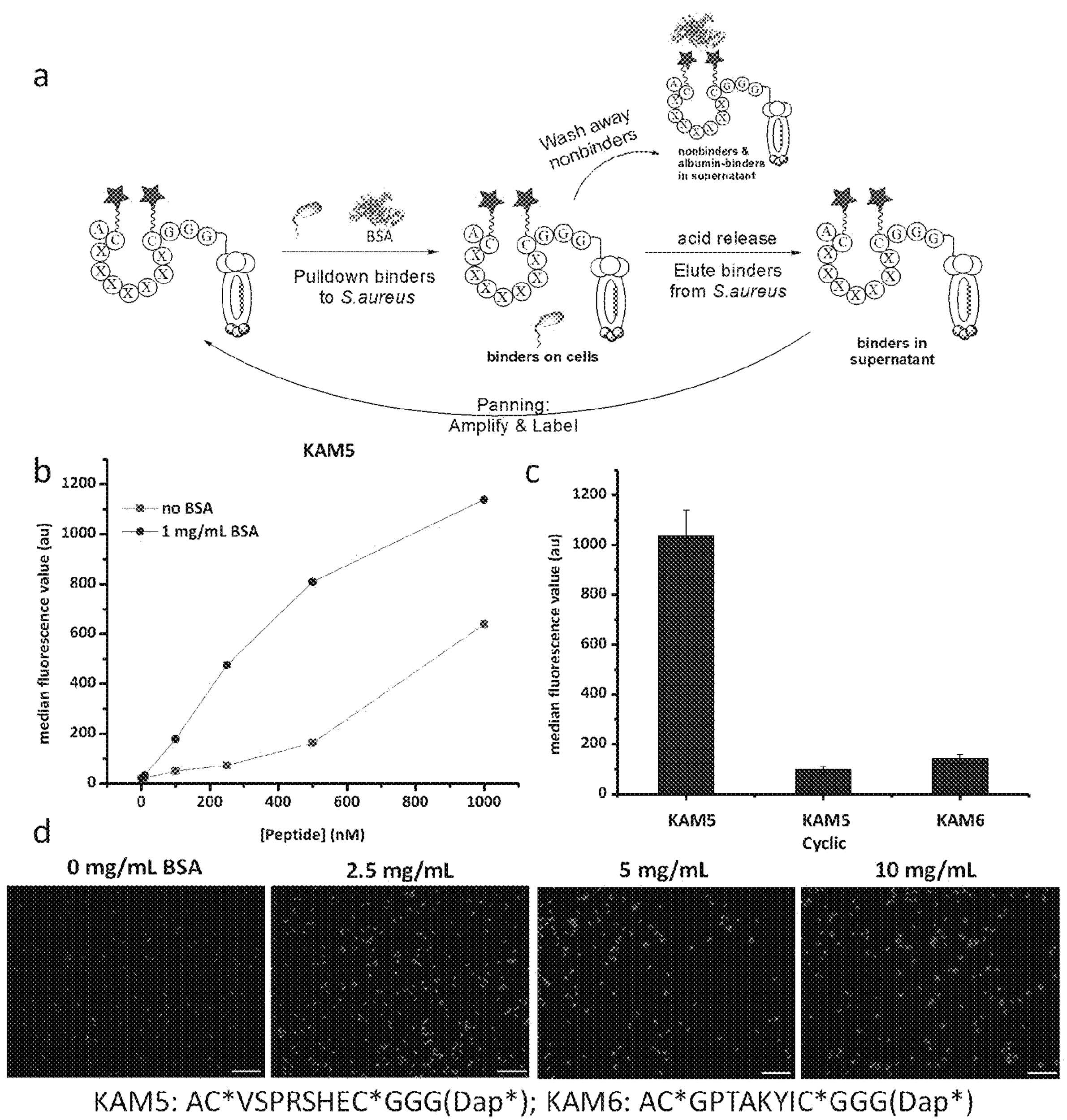
FIGS. 2A-2D show phage display against *S. aureus*. (A). Schematic representation of panning against live bacterial cells (SEQ ID NOS: 271-274, respectively, in order of appearance). Stars denote APBA-IA modification. (B). Flow cytometry analysis of fluorescein labeled KAM5 in for staining *S. aureus* cells. Data of replicate experiments are given in FIGS. 14A-14C, which shows consistent results. (C). Flow cytometry comparison of KAM5 to KAM5 Cyclic (no APBA modification) and a naive APBA dimer peptide KAM6. All peptides were labeled with fluorescein and used for cell staining at 1 μM concentration and in the presence of 1 mg/mL BSA. (D). Microscopic images of *S. aureus* cells stained with 2 μM KAM5 (SEQ ID NOS: 275-276, respectively, in order of appearance). TAMRA labeled KAM5 was used for microscopy due to better photostability of the fluorophore. Scale bar: 10 μm.
Figure 10:
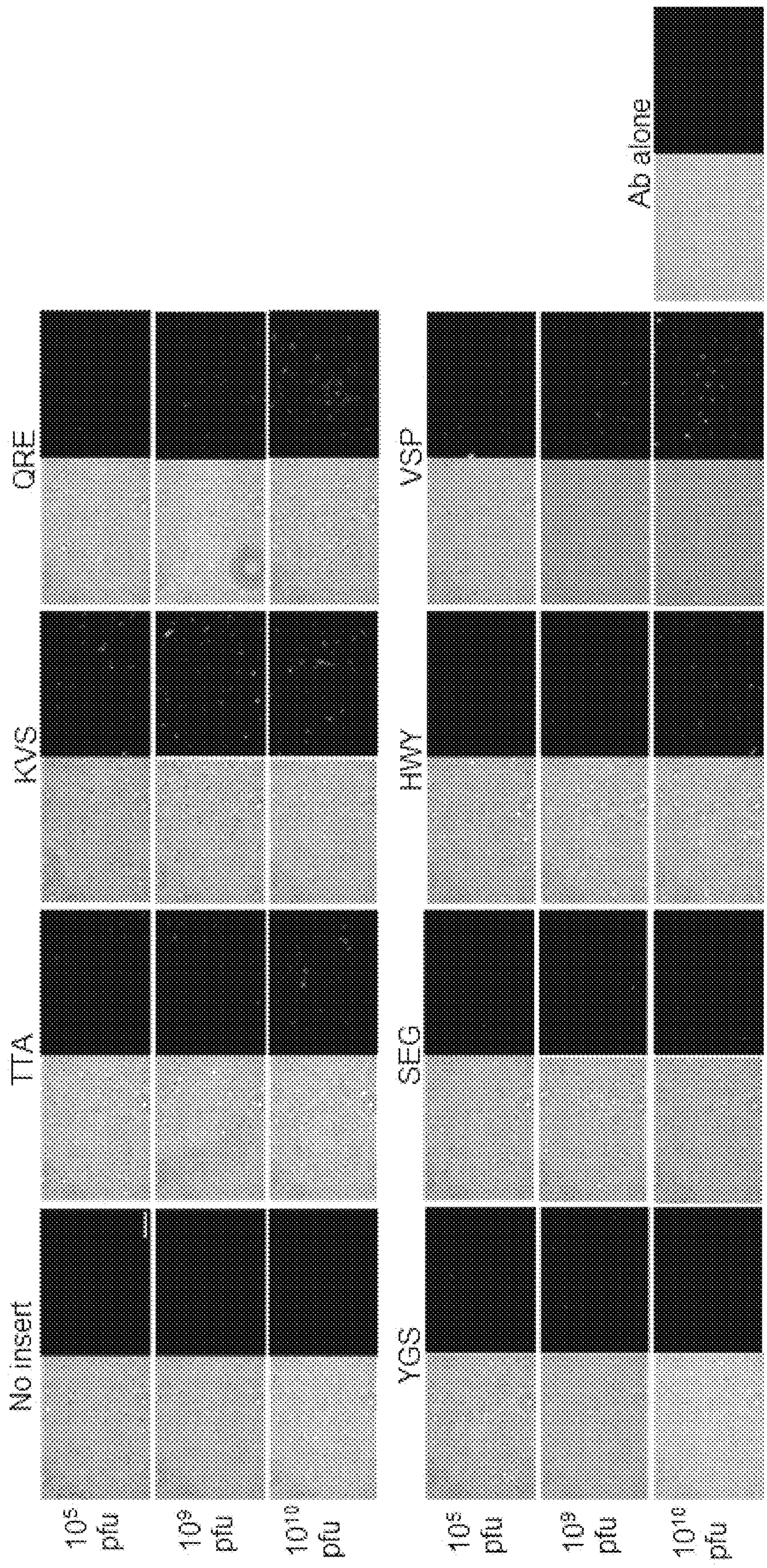
FIG. 10 shows fluorescence microscopy studies of phage binding to *S. aureus* assessed using anti-M13 antibody (FITC labeled). Each phage variant is designated as the first three letters of the heptapeptide sequence. Scale bar: 10 μm.
Figure 11A:
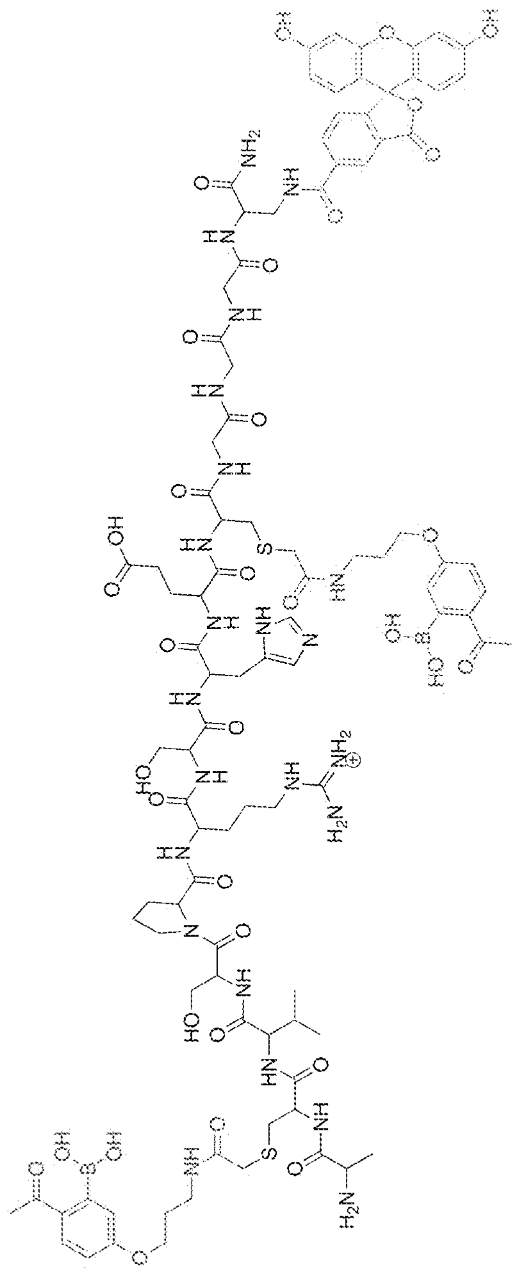
FIGS. 11A-11B show (A) structure and (B) LC-MS characterization of KAM5 with a fluorescein label. The results are shown as an example to demonstrate the purity and integrity of the peptides used for this study.
Figure 11B:
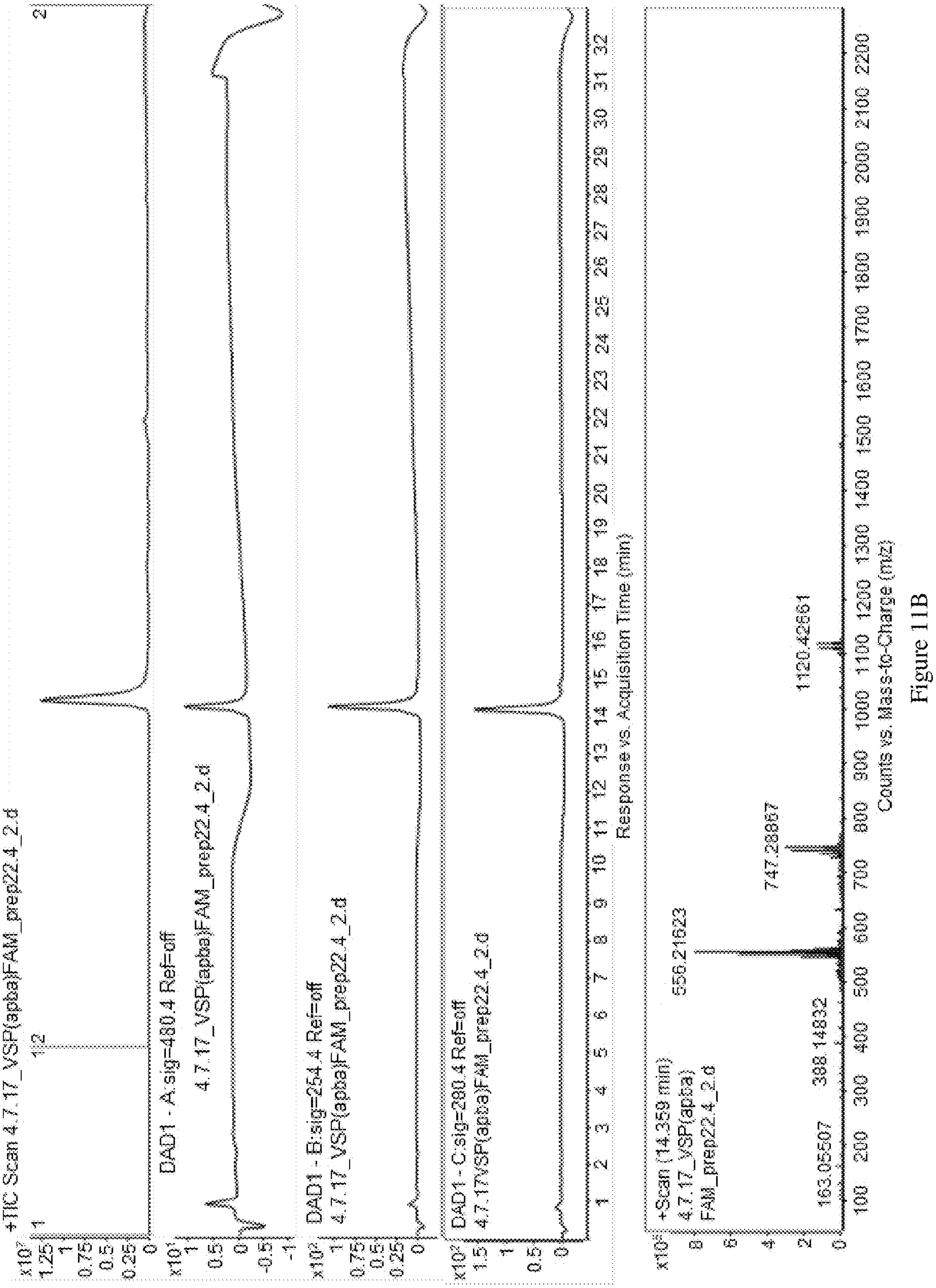

Panning phage libraries directly against live bacterial cells presents an intriguing alterative to panning against target biomolecules. However, earlier efforts along this front have only yielded low affinity (sub to low millimolar) peptide probes. It was postulated that panning the APBA-dimer library against *S. aureus* has the potential to discover highly potent and selective peptide probes for this bacteria because it is known to overexpress lysine modified phosphoglycerol (Lys-PG) to afford resistance to host defense peptides. In fact, Lys-PG synthesis is one of the critical features of *S. aureus* that makes it a prevalent pathogen. To avoid interference of endogenous proteins, which can compete for iminoboronate formation, the APBA-dimer library was screened against *S. aureus* cells in a suspension containing 10 mg/mL bovine serum albumin (BSA) as an internal competitor (FIG. 2A). Three rounds of affinity selection were initiated with an input population of $10^{10}$ plaque forming units (pfu) in each round along with extensive washing steps to eliminate non-binders and strong albumin binders by centrifugation. Acid treatment, which is known to disrupt iminoboronate formation, was used to release bound phage from *S. aureus*. The output population typically ranged from $10^3$ to $10^5$ pfu for *S. aureus* panning. The recovered phage were amplified, labeled with APBA-IA and subjected to the next round of panning. After each round of panning, 10-20 colonies were randomly selected from the output population and subjected to sequencing. Several peptide sequences were observed repeatedly in round 2 and round 3 even within this small set of colonies subjected for sequencing (Table 1). To determine which sequences merited further pursuit, a phage-based microscopy experiment was performed. The individual phage hits were modified with APBA-IA, incubated with *S. aureus*, and subsequently treated with a FITC-labeled anti-M13 antibody, which binds to the pVIII protein of the M13 phage. The phage-bound *S. aureus* was imaged via fluorescence microscopy to determine which phage sequences elicited the most potent bacterial labeling (FIG. 10). From these results, the five peptide hits that displayed the brightest images were selected and synthesized via solid phase peptide synthesis (KAM1-KAM5, Table 2). Synthesis was performed on a rink amide resin incorporating an orthogonally protected diaminopropionic acid (Dap) residue on the C-terminus, which allowed for on-resin coupling of fluorescein or rhodamine as a fluorescent reporter. A triple glycine linker was installed between Dap and the core C7C peptide to minimize interference of the fluorophore. After peptide synthesis, the pair of cysteines was subsequently modified with APBA-IA. The purity and identity of the final peptides were assessed via LC-MS analysis (Table 3, FIGS. 11A-11B).

Table 1 below shows sequences (SEQ ID NOS: 1-83, respectively, in order of columns) of the peptide hits for *S. aureus* binding (a) from round 2. (b) from round 3. (c) recurring sequences and frequency.

| a | | |
|---|---|---|
| Hit # | DNA Sequence | Peptide Sequence |
| 1 | GCTTGTACGACTGCTGCGTCGCGTTTGTGC | ACTTAASRLC |
| 2 | GCTTGTCCTGATGGTTTGAGTCCGCGTTGC | ACPDGLSPRC |
| 3 | GCTTGTCCGACGAGTAATAATCGGGAGTGC | ACPTSNNREC |
| 4 | GCTTGTAATTTTACTAAGACGTTTCGTTGC | ACNFTKTFRC |
| 5 | GCTTGTAAGGTGAGTAAGATGGAGCGTTGC | ACKVSKMERC |
| 6 | n/a | Blank |
| 7 | GCTTGTAAGTTTGATTCGACGAGGTATTGC | ACKFDSTRYC |
| 8 | GCTTGTCTTGAGCTTTTTCATTCGTCGTGC | ACLELFHSSC |
| 9 | GCTTGTACGAATCCTGTGACTGCTCGGTGC | ACTNPVTARC |
| 10 | GCTTGTACGAATACGCTGCCTAAGCTGTGC | ACTNTLPKLC |
| 11 | GCTTGTCAGAGGGAGATGACGCATATGTGC | ACQREMTHMC |
| 12 | GCTTGTATGAATCCGCGGGGTAATTTGTGC | ACMNPRGNLC |
| 13 | GCTTGTTATGGTTCTATGTCGAGTATGTGC | ACYGSMSSMC |
| 14 | n/a | Blank |
| 15 | GCTTGTCAGAGGGAGATGACGCATATGTGC | ACQREMTHMC |
| 16 | GCTTGTACGACTGCTGCGTCGCGTTTGTGC | ACTTAASRLC |
| 17 | GCTTGTGCTAGGGTTCATTCGTTGGGTTGC | ACARVHSLGC |
| 18 | GCTTGTAATCCGACTTCGCTTAATTCGTGC | ACNPTSLNSC |

-continued

| | | |
|---|---|---|
| 19 | GCTTGTAGTACGAATAGTAATATTGTGTGC | ACSTNSN VC |
| 20 | GCTTGTAATACTCAGTCGAAGCATGAGTGC | ACNTQSKHEC |

b

| Hit # | DNA Sequence | Peptide Sequence |
|---|---|---|
| 1 | GCTTGTACGACTGCTGCGTCGCGTTTGTGC | ACTTAASRLC |
| 2 | GCTTGTAAGGTGAGTAAGATGGAGCGTTGC | ACKVSKMERC |
| 3 | GCTTGTACGACTGCTGCGTCGCGTTTGTGC | ACTTAASRLC |
| 4 | GCTTGTAGTGAGGGTAGGGCTTATGCTTGC | ACSEGRAYAC |
| 5 | GCTTGTCATTGGTATTCTAGTAAGGCTTGC | ACHWYSSKAC |
| 6 | GCTTGTCATTGGTATTCTAGTAAGGCTTGC | ACHWYSSKAC |
| 7 | GCTTGTGTTTCTCCGAGGAGTCATGAGTGC | ACVSPRSHEC |
| 8 | GCTTGTCAGAGGGAGATGACGCATATGTGC | ACQREMTHMC |
| 9 | GCTTGTACGACTGCTGCGTCGCGTTTGTGC | ACTTAASRLC |
| 10 | GCTTGTACGACTGCTGCGTCGCGTTTGTGC | ACTTAASRLC |
| 11 | GCTTGTACGACTGCTGCGTCGCGTTTGTGC | ACTTAASRLC |
| 12 | GCTTGTTATGGTTCTATGTCGAGTATGTGC | ACYGSMSSMC |
| 13 | GCTTGTGTTTCTCCGAGGAGTCATGAGTGC | ACVSPRSHEC |
| 14 | GCTTGTGTTTCTCCGAGGAGTCATGAGTGC | ACVSPRSHEC |
| 15 | GCTTGTGTTTCTCCGAGGAGTCATGAGTGC | ACVSPRSHEC |
| 16 | GCTTGTAGTGAGGGTAGGGCTTATGCTTGC | ACSEGRAYAC |
| 17 | GCTTGTAAGTATTCTCATTCTAGTTCTTGC | ACKYSHSSSC |
| 18 | GCTTGTCATTGGTATTCTAGTAAGGCTTGC | ACHWYSSKAC |
| 19 | GCTTGTACGAAGTTGATGCATGGTTGGTGC | ACTKLMHGWC |
| 20 | GCTTGTAGTGAGGGTAGGGCTTATGCTTGC | ACSEGRAYAC |

c

| Peptide Sequence | Round 2 Frequency | Round 3 Frequency |
|---|---|---|
| ACTTAASRLC | 2 | 5 |
| ACKVSKMERC | 1 | 1 |
| ACQREMTHMC | 2 | 1 |
| ACYGSMSSMC | 1 | 1 |
| ACSEGRAYAC | 0 | 3 |
| ACHWYSSKAC | 0 | 3 |
| ACVSPRSHEC | 0 | 4 |

Table 2 below shows synthesized peptide hits from *S. aureus* screening (SEQ ID NOS: 84-88, respectively, in order of appearance).

| NAME | PEPTIDE SYNTHESIZED |
|---|---|
| KAM1 | AC$_m$TTAASRLC$_m$GGGDap* |
| KAM2 | AC$_m$KVSKMERC$_m$GGGDap* |
| KAM3 | AC$_m$QREMTHMC$_m$GGGDap* |
| KAM4 | AC$_m$HWYSSKAC$_m$GGGDap* |
| KAM5 | AC$_m$VSPRSHEC$_m$GGGDap* |

$C_m$: APBA-IA modified cysteine; *: fluorophore modified.

Table 3 below shows mass-spec data of peptides prior to (a) and after (b) APBA-IA labeling (SEQ ID NOS: 89-106, respectively, in order of appearance). Dap*: FAM labeled; Dap*: TAMRA labeled; Dap*: Eosin labeled. Cm: APBA-IA modified cysteine.

a

| NAME | PEPTIDE SYNTHESIZED | Calculated mass | Observed mass |
|---|---|---|---|
| KAM1 | ACTTAASRLCGGGDap* | 1610.74 $[M+H]^+$ | 1610.63 $[M+H]^+$ |
| KAM2 | ACKVSKMERCGGGDap* | 1769.72 $[M+H]^+$ | 1769.72 $[M+H]^+$ |
| KAM3 | ACQREMTHMCGGGDap* | 1824.64 $[M+H]^+$ | 1824.74 $[M+H]^+$ |
| KAM4 | ACHWYSSKACGGGDap* | 885.45 $[M+H]^{2+}$ | 885.32 $[M+H]^{2+}$ |
| KAM5 | ACVSPRSHECGGGDap* | 1703.64 $[M+H]^+$ | 1703.63 $[M+H]^+$ |
| | ACVSPRSHECGGGDap* | 878.87 $[M+H]^{2+}$ | 878.84 $[M+H]^{2+}$ |
| | ACVSPRSHECGGGDap* | 2018.38 $[M+H]^+$ | 2018.05 $[M+H]^+$ |
| | ACVSPRSHECGGGDap(alloc) | 1428.60 $[M+H]^+$ | 1428.58 $[M+H]^+$ |
| KAM6 | ACGPTAKYICGGGDap* | 1641.58 $[M+H]^+$ | 1641.65 $[M+H]^+$ |

b

| NAME | PEPTIDE SYNTHESIZED | Calculated mass | Observed mass |
|---|---|---|---|
| KAM1 | AC$_m$TTAASRLC$_m$GGGDap* | 1073.93 $[M-H_2O+H]^{2+}$ | 1073.92 $[M-H_2O+H]^{2+}$ |
| KAM2 | AC$_m$KVSKMERC$_m$GGGDap* | 1144.48 $[M-2H_2O+H]^{2+}$ | 1144.46 $[M-2H_2O+H]^{2+}$ |
| KAM3 | AC$_m$QREMTHMC$_m$GGGDap* | 1180.59 $[M-H_2O+H]^{2+}$ | 1180.92 $[M-H_2O+H]^{2+}$ |
| KAM4 | AC$_m$HWYSSKAC$_m$GGGDap* | 1153.44 $[M-H_2O+H]^{2+}$ | 1153.92 $[M-H_2O+H]^{2+}$ |
| KAM5 | AC$_m$VSPRSHEC$_m$GGGDap* | 1120.43 $[M-2H_2O+H]^{2+}$ | 1120.42 $[M-2H_2O+H]^{2+}$ |
| | AC$_m$VSPRSHEC$_m$GGGDap* | 1138.48 $[M-2H_2O+H]^{2+}$ | 1138.44 $[M-2H_2O+H]^{2+}$ |
| | AC$_m$VSPRSHEC$_m$GGGDap* | 1268.78 $[M-2H_2O+H]^{2+}$ | 1268.71 $[M-2H_2O+H]^{2+}$ |
| | AC$_m$VSPRSHEC$_m$GGGDap(alloc) | 1947.74 $[M-2H_2O+H]^+$ | 1947.82 $[M-2H_2O+H]^+$ |
| KAM6 | AC$_m$GPTAKYIC$_m$GGGDap* | 1088.95 $[M-H_2O+H]^{2+}$ | 1089.43 $[M-H_2O+H]^{2+}$ |

Example 7

Characterization of Peptide Hits

Figures 12A, 12B, 12C, 12D:
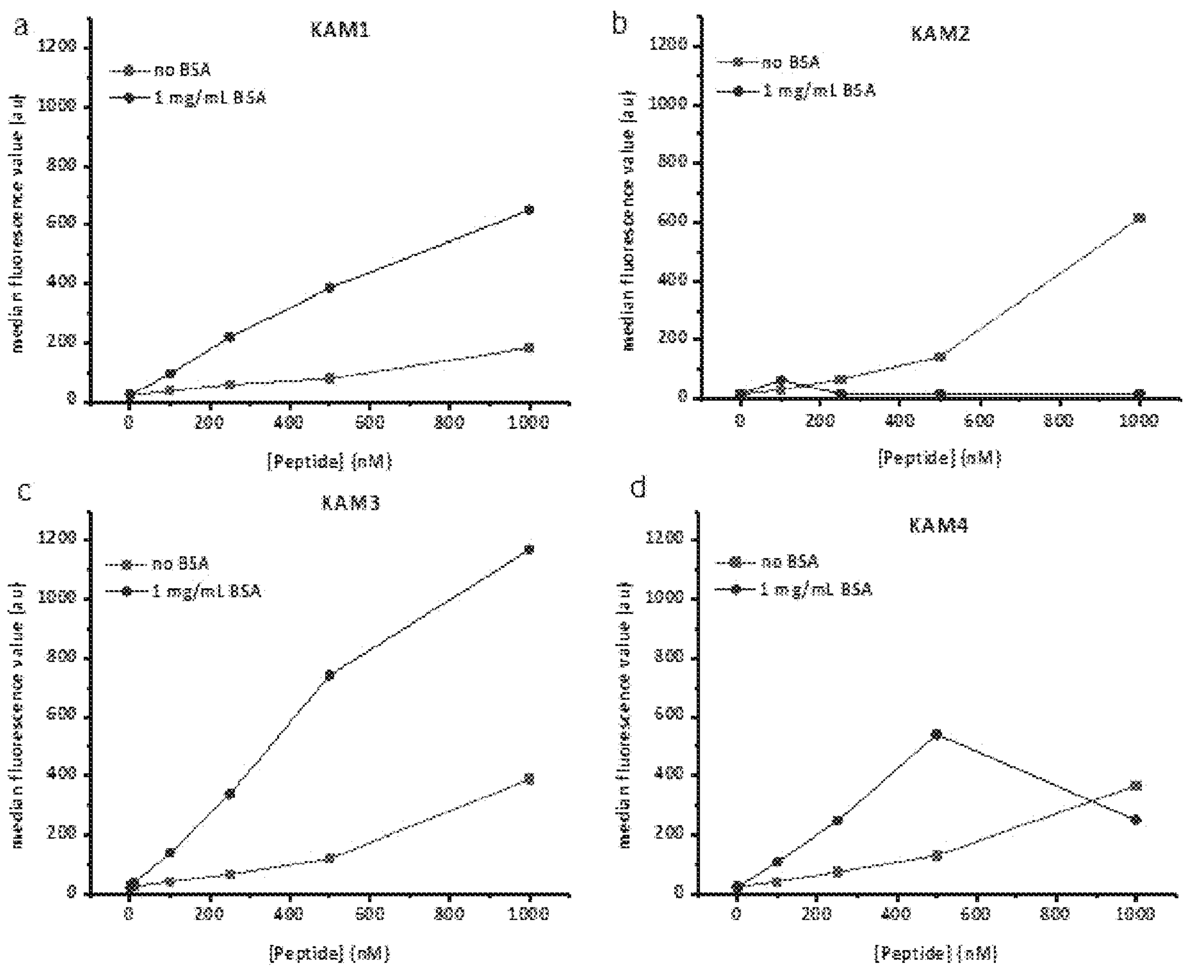
FIGS. 12A-12D show flow cytometry analysis of *S. aureus* staining by KAM1 (A), KAM2(B), KAM3(C), and KAM4 (D) in presence and absence of BSA.
Figures 13A, 13B:
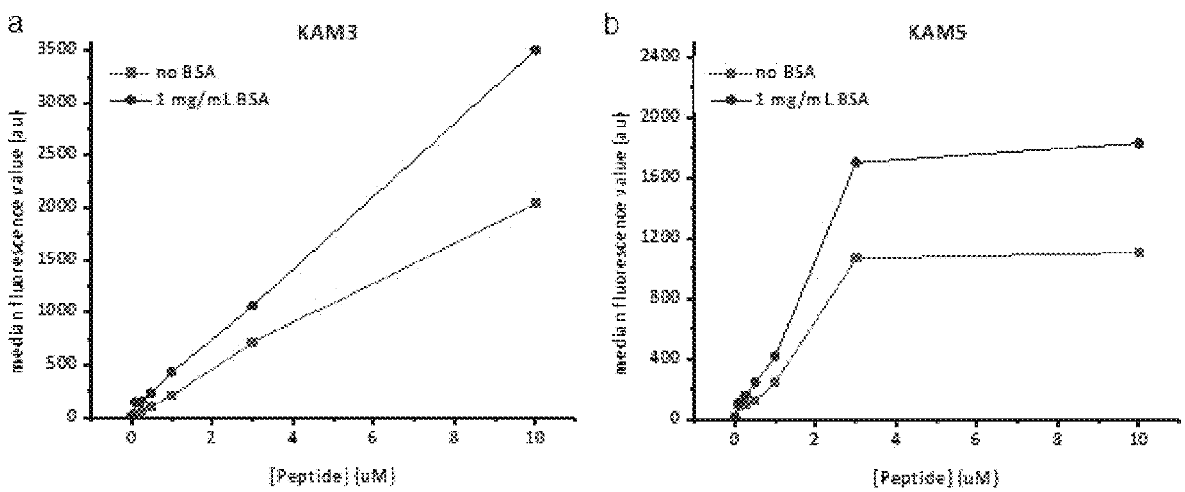
FIGS. 13A-13B show flow cytometry analysis of *S. aureus* staining by KAM3 (A) and KAM5 (B) up to 10 μM in concentration. Results are shown for with and without BSA.
Figure 15:
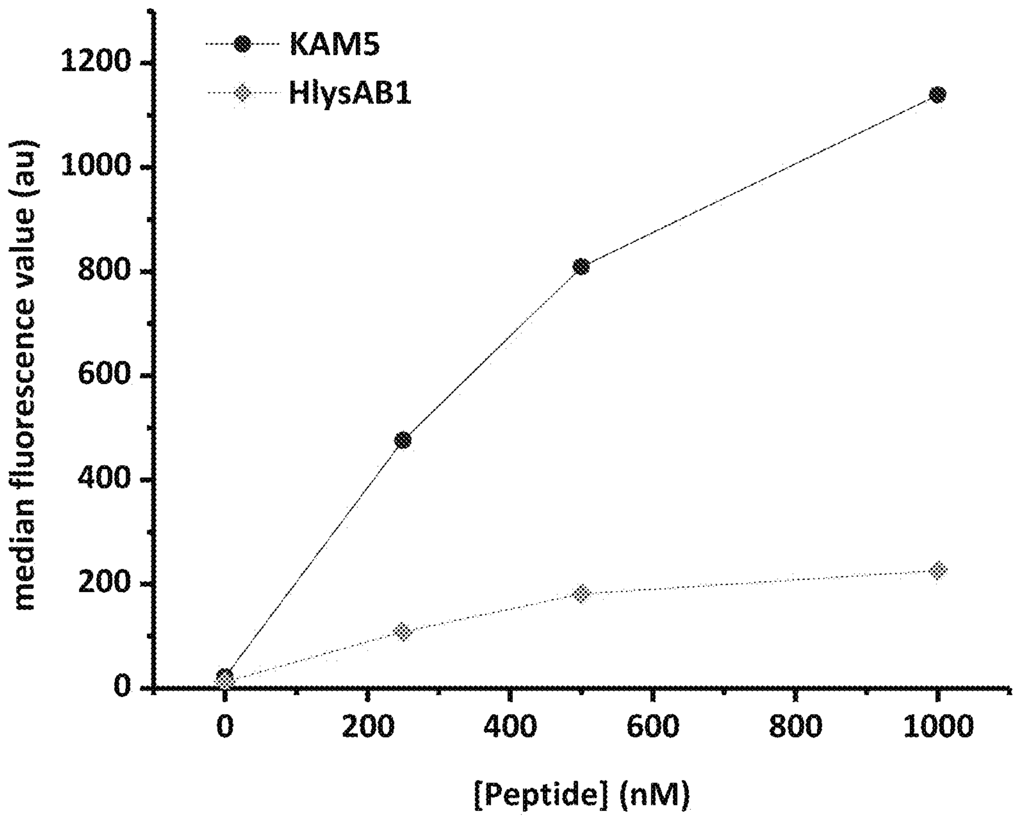
FIG. 15 shows concentration profile of KAM5 staining *S. aureus* in comparison to that of a previously reported peptide for *S. aureus* labeling (Hlys-AB1). All samples were prepared to have 1 mg/mL BSA.

To assess *S. aureus* binding, flow cytometry was used to measure the median fluorescence intensity of the cells that each peptide hit gave. All five peptide hits showed significant binding to *S. aureus* cells at sub-micromolar concentrations (FIG. 2B, FIGS. 12A-12B; FIGS. 13A-13B; and FIGS. 14A-14B). Interestingly, all peptides except KAM2 afforded even stronger fluorescence staining of the bacteria in the presence of 1 mg/mL BSA than otherwise. Analysis of the bacterial binding curve of KAM5 gave an estimated $EC_{50}$ of ~1.5 μM for staining *S. aureus* cells (FIG. 13B (KAM5)). The bacterial binding potency displayed by KAM5 is orders of magnitude better than the peptides borne out of previous phage display efforts with natural peptide libraries, which only yielded sub to low mM binders. The *S. aureus* binding potency of KAM5 is also much greater than that of Hlys-AB1, a rationally designed peptide that incorporates a single APBA motif (FIG. 15). Importantly, a negative control peptide KAM6, which was not selected from the screen and contains a random heptapeptide sequence, showed no bacterial staining under the same experimental conditions (FIG. 2C). Furthermore, the cyclic precursor of KAM5 (KAM5-Cyclic which has no APBA moieties) elicited little *S. aureus* staining as well, demonstrating the importance of the APBA warhead (FIG. 2C).

Figures 16A, 16B:
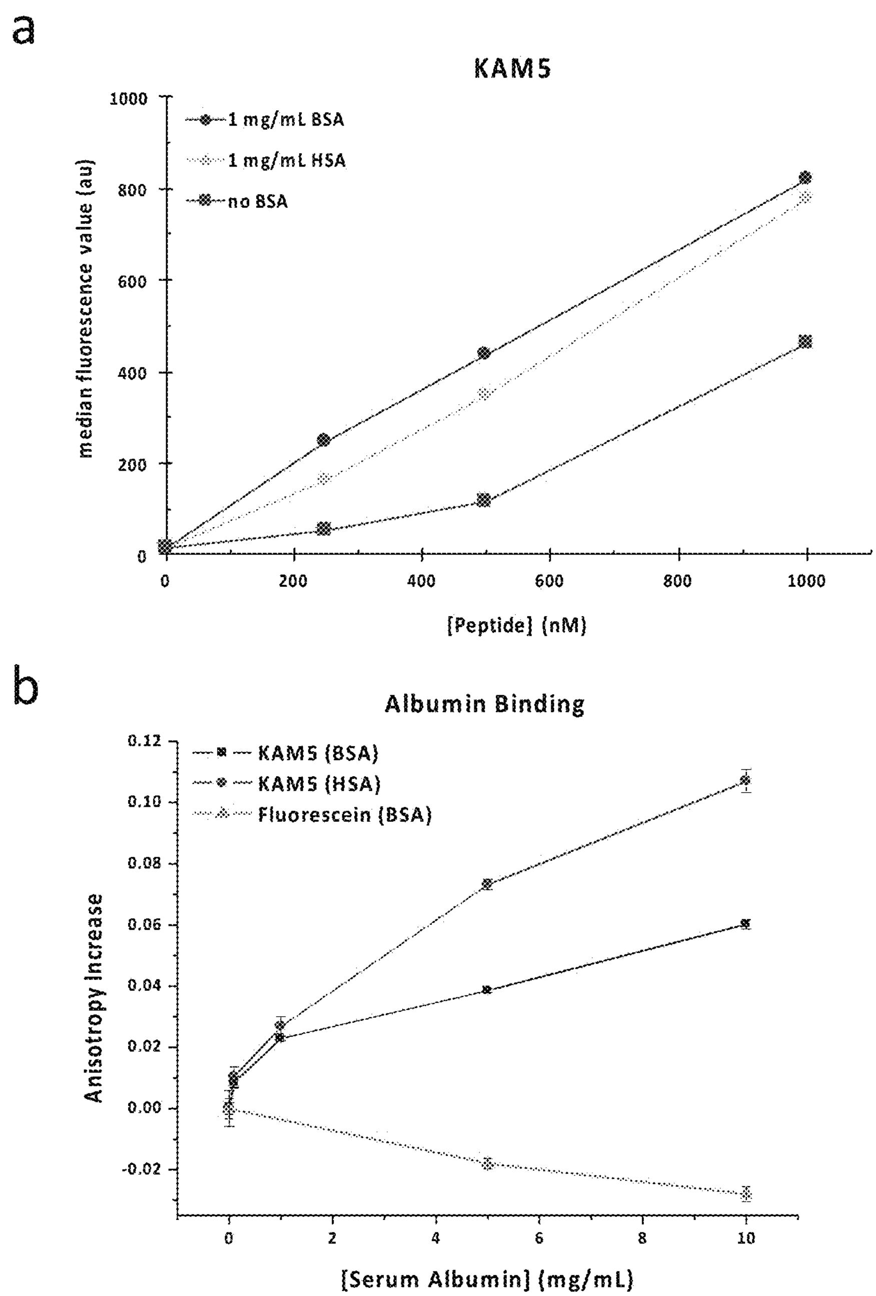
FIGS. 16A-16B show further evaluation of the protein-enhanced bacterial staining by KAM5. (A) Flow cytometry comparison of HSA and BSA in enhancing KAM5 binding to *S. aureus*. (B) Assessing protein binding of KAM5 using fluorescence anisotropy, for which various concentrations of BSA or HSA were delivered to a 96-well plate (Corning 3603) in PBS (pH 7.4). Peptide was added at a final concentration of 500 nM and incubated for 1 hour. Anisotropy values were measured (Ex: 495 nm, Em: 532 nm) and plotted as an average of three trials with standard deviations. Fluorescein was used as a negative control. The results clearly show binding of KAM5 to these serum proteins.

The cell staining ability of KAM5 was also evaluated via fluorescence microscopy with a TAMRA labeled peptide. The microscopy studies yielded results consistent with those of flow cytometry: KAM5 at 2 μM concentration gave strong fluorescence staining of *S. aureus* cells and the addition of BSA up to 10 mg/mL did not inhibit the bacterial staining by KAM5. On the contrary, the BSA addition elicited stronger fluorescence staining of the bacteria, consistent with the flow cytometry results (FIG. 2D). The protein-enhanced bacterial binding by KAM5 is not BSA-specific as similar enhancement was observed with human serum albumin (HSA) as well (FIGS. 16A-16B). To better understand this phenomenon, KAM5 was measured binding to these serum proteins via a fluorescence anisotropy experiment (FIGS. 16A-16B). KAM5 did show binding to both BSA and HAS at high protein concentrations, which is perhaps not surprising given these proteins display a large number of surface lysine residues. These results suggest that BSA/HSA may enhance KAM5 binding to *S. aureus* by forming ternary complexes, although the detailed mechanism requires further investigation.

Figures 3A, 3B:
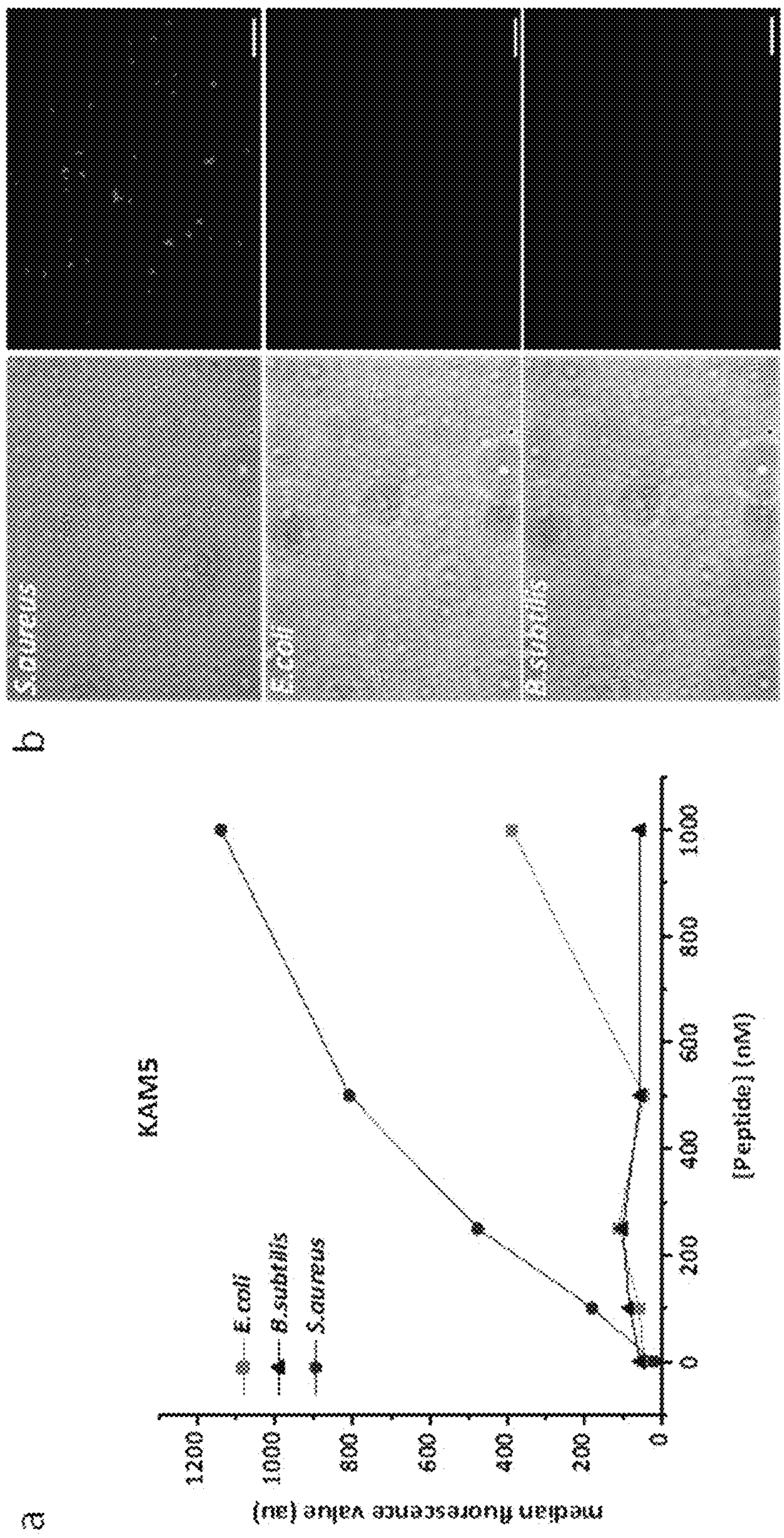
FIGS. 3A-3B show selective binding of KAM5 to *S. aureus* over other bacterial species. *B. subtilis* & *E. coli* were used as representative gram-positive and gram-negative bacteria species. (A). Results of flow cytometry analysis with fluorescein labeled KAM5 in the presence of 1 mg/mL BSA. Replicate data set is given in FIG. 14, which shows consistent results. (B). Results of microscopy analysis using TAMRA labeled KAM5 (10 Scale bar: 10 μm.
Figure 17:
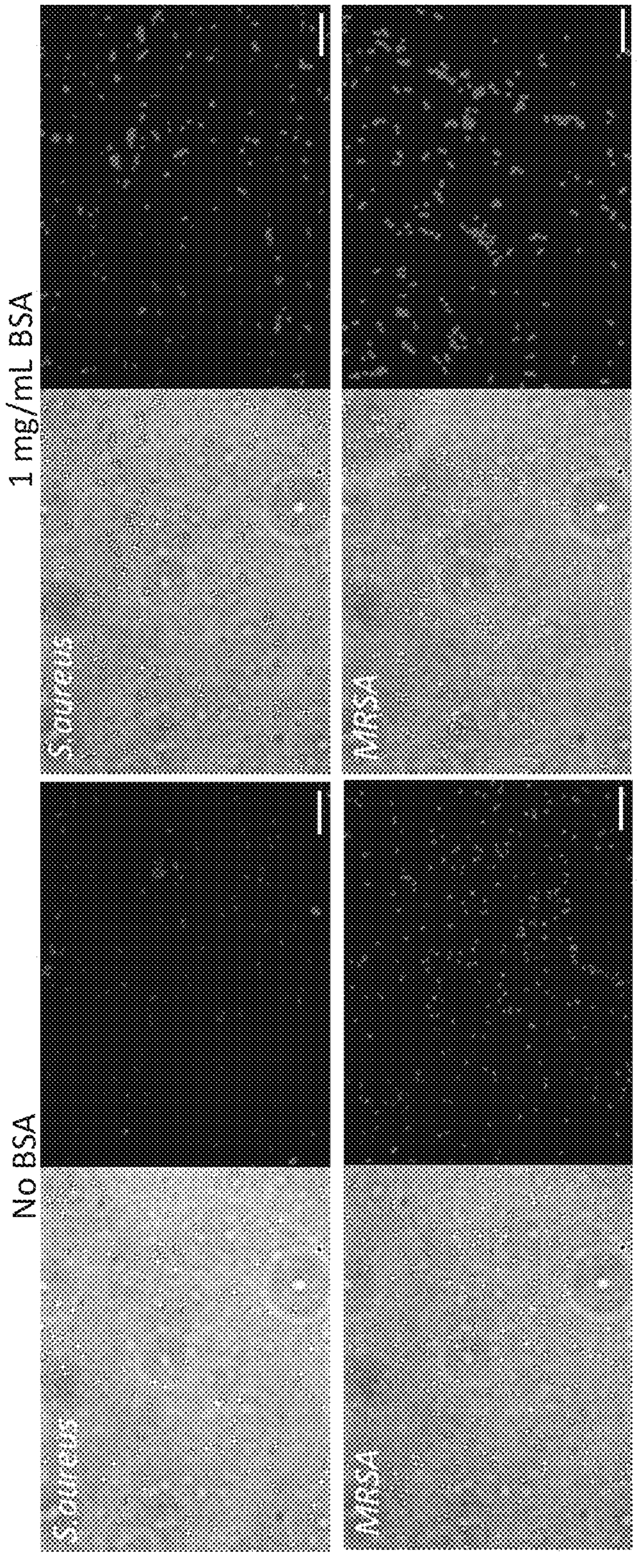
FIG. 17 shows microscopic images of *S. aureus* and MRSA treated with TAMRA labeled KAM5 at 2 μM concentration. Scale bar: 10 μm.

Further analysis of KAM5 showed equally potent staining of a methicillin-resistant strain of *S. aureus* (ATCC 43300) in comparison to the strain (ATCC 6358) used in phage display (FIG. 17). This is consistent with our hypothesis that KAM5 binds the bacteria via covalent conjugation to Lys-PG, which is present on essentially all *S. aureus* strains, although its percentage may vary. The bacterial selectivity of KAM5 toward different bacterial species was further analyzed. Specifically, KAM5 labeling of *Escherichia coli*, a model gram-negative bacterium, and *Bacillus subtilis*, a model gram-positive bacterium, was assessed via flow cytometry (FIG. 3A) and fluorescence microscopy (FIG. 3B). The data revealed negligible staining of these control bacterial species with up to 10 μM peptide, highlighting the desirable species selectivity towards *S. aureus*.

Example 8

Comparison to Control Phage Libraries

Figure 18:
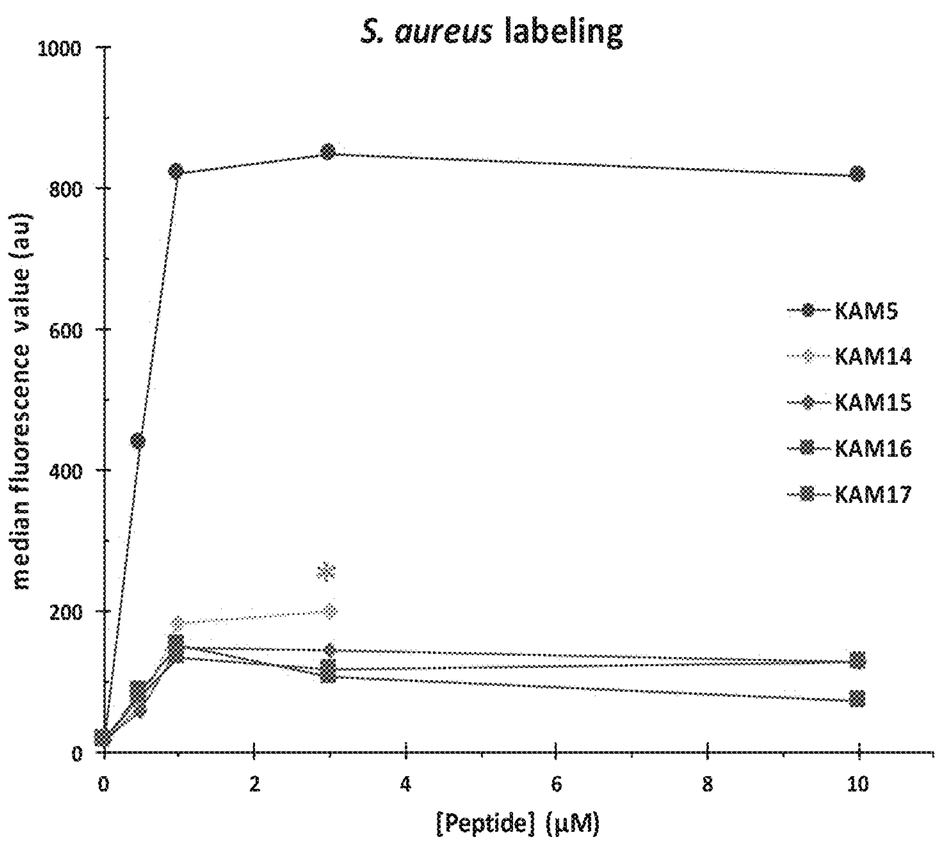
FIG. 18 shows flow cytometry analysis of KAM14-17 for *S. aureus* staining in comparison to KAM5. The results clearly show the superior potency of the iminoboronate-capable peptide KAM5 for labeling *S. aureus* cells. *Note: KAM14 was only analyzed up to 3 μM due to aggregation at higher concentrations.

To directly assess the advantage of the APBA modified phage library, parallel screening was performed for *S. aureus* binding using the unmodified C7C library, as well as a C7C-derived library in which the reduced cysteines were alkylated with simple iodoacetamide (C7C-IA library). The *S. aureus* panning experiments were performed by following the same protocol used for the APBA-dimer library. Three rounds of panning of the unmodified C7C library did yield two repeating sequences (Table 4). However, when synthesized and characterized using flow cytometry, neither of these peptides showed significant bacterial staining up to 10 μM (FIG. 18), the highest concentration allowed by the flow cytometry instrument. Even if they did bind *S. aureus* at higher concentrations, their affinity for the bacteria would be much lower than that of KAM5. It is worth noting that the final output population of the C7C library, in comparison to the APBA-dimer library, contains a proportionally larger number of blank sequences (no peptide displayed), which presumably came from the original, imperfectly created C7C library and did not get selected out during the panning process. The higher percentage of blank sequences suggests that the unmodified C7C library offers few potent binders or "real hits" for *S. aureus*. Similarly, after three rounds of panning, the C7C-IA library gave a larger number of blank sequences as well, yet only one sequence showing repeats (Table 5). Characterization of this recurring sequence, as well as a randomly picked sequence out of the round 3 output population, failed to show bacterial staining up to 10 μM (Table 6, FIG. 18). The failure of these control libraries is consistent with earlier phage display efforts where screening of natural peptide libraries was only able to yield sub-to-low millimolar binders of bacteria at best. Collectively, the comparative study presented here clearly showcases the advantage of phage display with dynamic covalent binding motifs.

Table 4 below shows sequences (SEQ ID NOS 107-146, respectively, in order of columns) obtained from panning the unmodified C7C library against *S. aureus* (a) from round 2. (b) from round 3. (c) recurring sequences and frequency.

| a | | |
|---|---|---|
| Hit # | DNA Sequence | Peptide Sequence |
| 1 | n/a | Blank |
| 2 | GCTTGTTCTACTTTGGCGCAGCGTGCGTGC | ACSTLAQRAC |
| 3 | GCTTGTCCGAAGTCGAGTATTGATCCGTGC | ACPKSSIDPC |
| 4 | GCTTGTACTAAGGATAGTCCGGGGCTTTGC | ACTKDSPGLC |
| 5 | n/a | Blank |
| 6 | GCTTGTCTGAATGCTGTTACGGAGAAGTGC | ACLNAVTEKC |
| 7 | n/a | Blank |
| 8 | GCTTGTGGGCTTAATGTTTCGACTCATTGC | ACGLNVSTHC |
| 9 | GCTTGTTGGTTGAGTGCGGCGGCGCAGTG | ACWLSAAAQC |
| 10 | n/a | Blank |

| b | | |
|---|---|---|
| Hit # | DNA Sequence | Peptide Sequence |
| 1 | n/a | Blank |
| 2 | GCTTGTTCTGCGTATGATAGGCCTCTTTGC | ACSAYDRPLC |
| 3 | n/a | Blank |
| 4 | GCTTGTGCTAAGATTTTTACTGGTTGTTGC | ACAKIFTGCC |
| 5 | GCTTGTTCGCCTTGGAATCCTTCGCATTGC | ACSPWNPSHC |
| 6 | GCTTGTACGGGTGCTTCTAATAATACTTGC | ACTGASNNTC |

-continued

| | | |
|---|---|---|
| 7 | GCTTGTTCGCCTTGGAATCCTTCGCATTGC | ACSPWNPSHC |
| 8 | GCTTGTGCTAAGATTTTTACTGGTTGTTGC | ACAKFTGCC |
| 9 | GCTTGTACGTCTGGTCCTGCTCTTACGTGC | ACTSGPALTC |
| 10 | n/a | Blank |
| 11 | GCTTGTGCTAAGATTTTTACTGGTTGTTGC | ACAKFTGCC |
| 12 | n/a | Blank |
| 13 | GCTTGTCGGCCGACTAATGGGTTTGCGTGC | ACRPTNGAAC |
| 14 | n/a | Blank |
| 15 | GCTTGTCAGTTGGTTCCTGGGGCTTATTGC | ACQLVPGAYC |
| 16 | GCTTGTACTCATCTGCATAAGCGTACGTGC | ACTHLHKRTC |
| 17 | GCTTGTTCGACGTTGTCGCAGCCTGCGTGC | ACSTLSQPAC |
| 18 | n/a | Blank |
| 19 | n/a | Blank |
| 20 | GCTTGTTCGCCTTGGAATCCTTCGCATTGC | ACSPWNPSHC |

c

| Peptide Sequence | Round 2 Frequency | Round 3 Frequency |
|---|---|---|
| ACAKFTGCC | 0 | 3 |
| ACSPWNPSHC | 0 | 3 |

Table 5 below shows sequences (SEQ ID NOS: 147-185, respectively, in order of columns) obtained from panning the C7C-IA library against *S. aureus* (a) from round 2. (b) from round 3. (c) recurring sequences and frequency.

a

| Hit # | DNA Sequence | Peptide Sequence |
|---|---|---|
| 1 | n/a | Blank |
| 2 | GCTTGTAAGCAGACTTATCCGCAGAGTTGC | ACKQTYPQSC |
| 3 | n/a | Blank |
| 4 | GCTTGTGCTACTCATGGGTTGGATAGGTGC | ACATHGLDRC |
| 5 | GCTTGTGAGAAGGAGGATAGTAGGAGGTGC | ACEKEDSRRC |
| 6 | GCTTGTTTGACTCTTCTGATGGAGGCGTGC | ACLTLLMEAC |
| 7 | n/a | Blank |
| 8 | GCTTGTACTCCGCATTCGCTGCATGCGTGC | ACTPHSLHAC |
| 9 | GCITGTAAGACTTCTGAGAAGACGAGTTGC | ACKTSEKTSC |
| 10 | n/a | Blank |

b

| Hit # | DNA Sequence | Peptide Sequence |
|---|---|---|
| 1 | GCTTGTACTTCTCCGGTTAAGACTCTITGC | ACTSPVKTLC |
| 2 | n/a | Blank |
| 3 | GCTTGTCATCGGCCTCATGAGGCGATGTGC | ACHRPHEAMC |
| 4 | GCTTGTCATGGTCCGAGGGCGTCTCAGTGC | ACHGPRASQC |

-continued

| | | |
|---|---|---|
| 5 | n/a | Blank |
| 6 | GCTTGTTTTAAGCATTCTAAGTTTGCGTGC | ACFKHSKFAC |
| 7 | GCTTGTAATCAGCTGATGAATTTGACTTGC | ACNGLMNLTC |
| 8 | n/a | Blank |
| 9 | GCTTGTCATCGGCCTCATGAGGCGATGTGC | ACHRPHEAMC |
| 10 | GCTTGTGATCATAGGACGCGGCCGTGGTGC | ACOHRTRPWC |
| 11 | n/a | Blank |
| 12 | n/a | Blank |
| 13 | GCTTGTCATCGGCCTCATGAGGCGATGTGC | ACHRPHEAMC |
| 14 | GCTTGTCCGACGGAGCTGCATTTTCATTGC | ACPTELHFHC |
| 15 | n/a | Blank |
| 16 | GCTTGTCATCGGCCTCATGAGGCGATGTGC | ACHRPHEAMC |
| 17 | GCTTGTACTAAGATGACGCTTCATTGC | ACTKMTLHC |
| 18 | n/a | Blank |
| 19 | gcttgtcagcatggtacgactcatggttgc | ACQHGTTHGC |
| 20 | GCTTGTATTCGTGATCAGAATATGCGGTGC | ACIRDQNMRC |

c

| Peptide Sequence | Round 2 Frequency | Round 3 Frequency |
|---|---|---|
| ACHRPHEAMC | C | 4 |

Table 6 below shows sequences (SEQ ID NOS: 186-189, respectively, in order of appearance) and mass-spec data of representative peptide hits from *S. aureus* screening with the C7C library (a) and C7C-IA library (b). KAM14 and KAM15 are the two recurring sequences from round 3 of the C7C library. The C7C-IA library only yielded one recurring sequence (KAM16) after round 3. An additional peptide (KAM17) was randomly chosen from the round 3 output population for analysis.

a

| NAME | PEPTIDE SYNTHESIZED | Calculated mass | Observed mass |
|---|---|---|---|
| KAMM | ACAKIFTGCCGGGDap* | 1628.83 $[M+H]^+$ | 1628.53 $[M+H]^+$ |
| KAMIS | ACSPWNPSHCGGGDap* | 1714.80 $[M+H]^+$ | 1714.53 $[M+H]^+$ |

b

| NAME | PEPTIDE SYNTHESIZED | Calculated mass | Observed mass |
|---|---|---|---|
| KAM16 | $AC_m$HRPHEAM$C_m$GGGDap* | 1883.69 $[M+H]^+$ | 1883.64 $[M+H]^+$ |
| KAM17 | $AC_m$TSPVKTL$C_m$GGGDap* | 1751.92 $[M+H]^+$ | 1751.67 $[M+H]^+$ |

Dap*: FAM labeled Dap, Cm: IA modified cysteine.

Example 9

Generating a Targeted Antibiotic for *S. aureus*

Figures 4A, 4B, 4C, 4D:
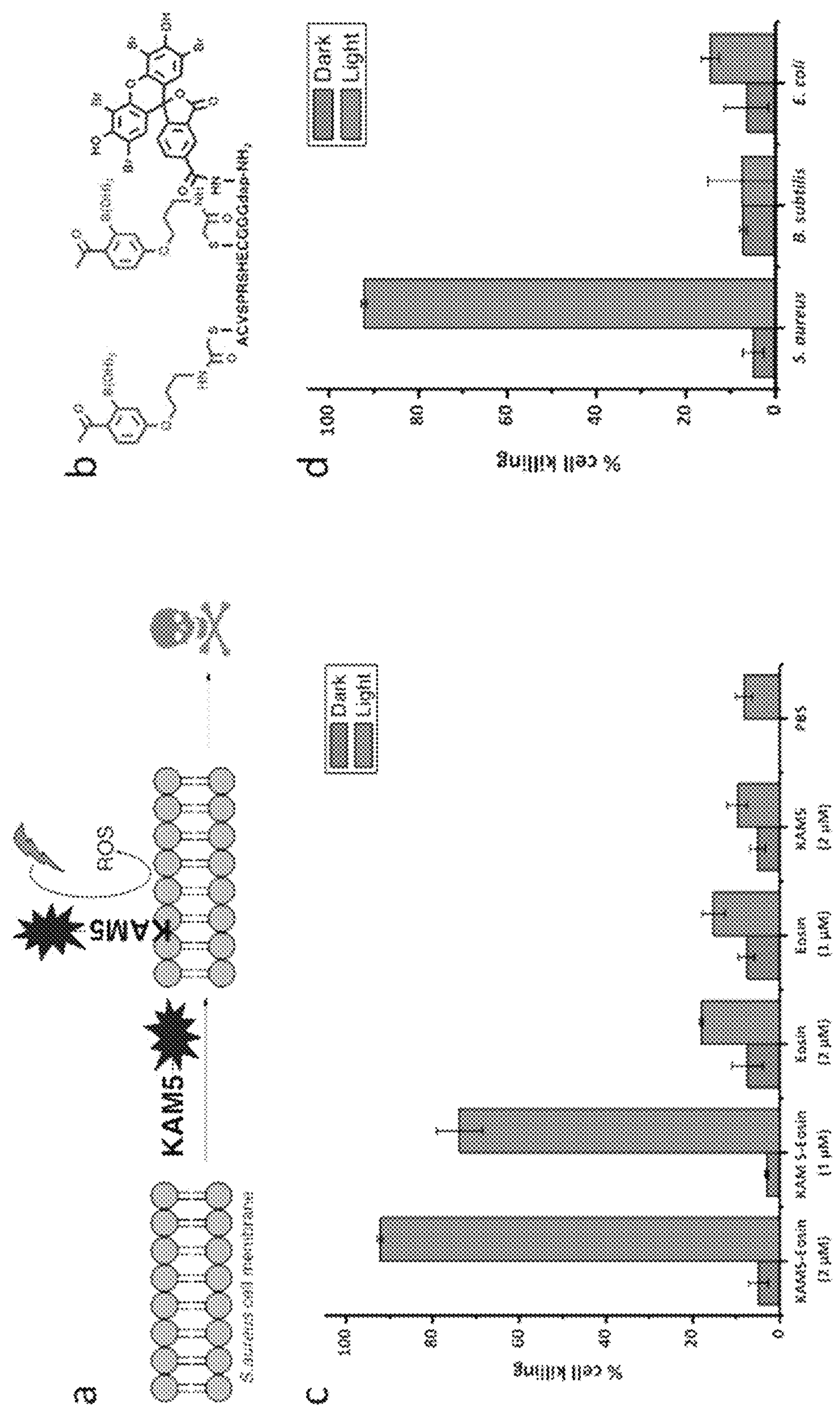
FIGS. 4A-4D show conjugation of a phototoxin to induce targeted killing of *S. aureus*. (A). Cartoon representation of photodynamic therapy with KAM5-Eosin. (B). Structure of KAM5-Eosin (SEQ ID NO: 277). (C). Percent killing of *S. aureus* by KAM5-Eosin and controls with and without photoirradiation. (D). Percent killing of several bacterial species with KAM5-Eosin (2 μM) to highlight the *S. aureus* specificity.
Figure 19:
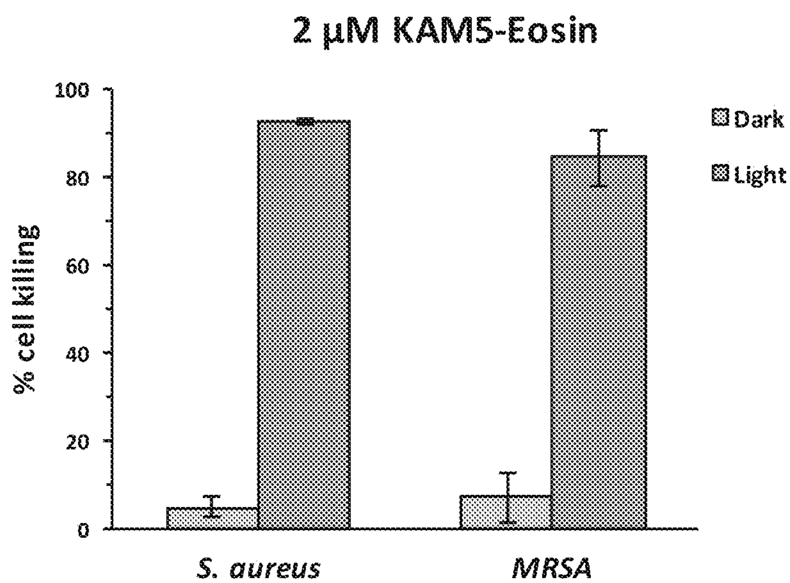
FIG. 19 shows KAM5-Eosin showing comparable potency for killing MRSA versus the strain of *S. aureus* used in phage selection of KAM5.
Figure 20A:
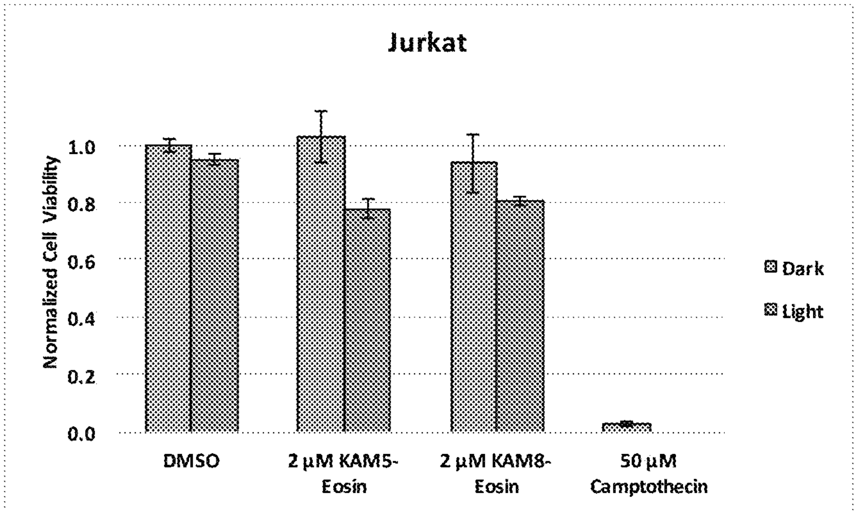
FIGS. 20A-20B show MTT assay to assess mammalian cell toxicity on Jurkat (A) and HEK293T (B) cells after treatment for 24 hrs. Note that, for HEK 293T cells, photoirradiation alone resulted in some extent of cell killing. However, the peptide addition elicited no additional cell killing indicating lack of toxicity.
Figure 20B:
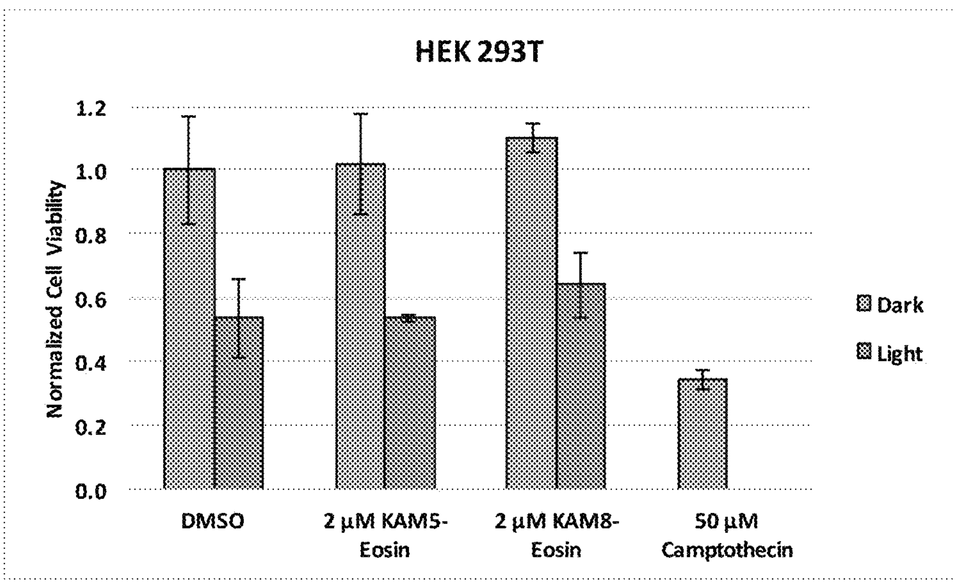

A potent and selective *S. aureus* binder has the potential to serve as a directing element to develop targeted antibiotics. The preferential binding of KAM5 towards *S. aureus* over serum proteins as well as other bacterial species makes it an excellent candidate for delivering a nonselective antibiotic to target cells. In this study, KAM5 was conjugated to eosin, a phototoxin that upon photoirradiation triggers the production of reactive oxygen species (ROS), killing cells in close proximity (FIG. 4A). There has been considerable interest in developing photoinactivation strategies for pathogenic bacteria, which has been encouraged by the technological advances and therapeutic successes achieved in photodynamic therapy. Delivery of a photosensitizer in a species-specific manner would maximize the benefit and minimize the side effect of photodynamic therapy in treating bacterial infections, particularly when the infection site hosts human commensal bacteria. Eosin was conjugated to KAM5 via the Dap residue, similar to the fluorophore labeling protocol (FIG. 4B). The conjugate was then assessed for photodynamic inactivation of *S. aureus* via a titering assay. When *S. aureus* was mixed with 1 μM and 2 μM KAM5-Eosin and then exposed to blue light for 15 minutes, 74% and 92% cell killing was observed respectively (FIG. 4C). Importantly, eosin alone at these concentrations did not elicit cell death nor did KAM5 without the photosensitizer. Extending the bactericidal assay into other strains of *S. aureus* revealed that KAM5-Eosin worked equally well against the MRSA strain with comparable percentage of cell killing under the same experimental conditions (FIG. 19). As expected from the cell binding specificity of KAM5, the cell killing of KAM5-Eosin was specific to *S. aureus* as no significant cell death was observed for *B. subtilis* and *E. coli* treated with 2 μM peptide followed by photoirradiation (FIG. 4D). Furthermore, no mammalian cell toxicity by KAM5-Eosin was observed via an MTT assay against HEK 293T cells and Jurkat cells with or without photoirradiation (FIGS. 20A-20B). These results clearly demonstrate the feasibility of developing species-selective antibiotics.

Example 10

Strain-Specific Targeting of *A. baumannii*

Figures 5A, 5B, 5C, 5D:
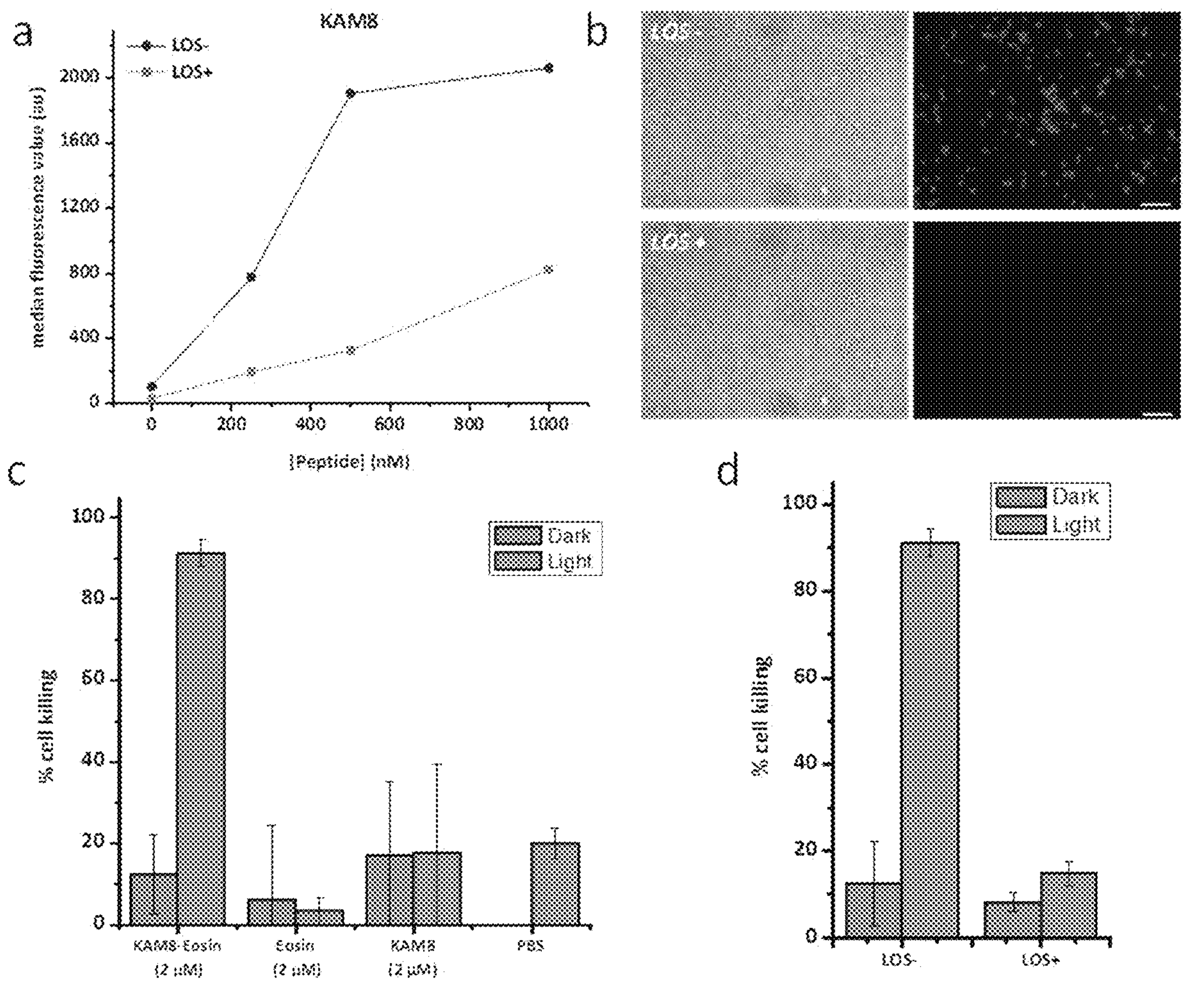
FIGS. 5A-5D show phage display to discover peptide probes for a LOS− strain of *A. baumannii* (AB5075). (A). Flow cytometry analysis of the representative peptide hit KAM8 in staining *A. baumannii* (LOS− vs LOS+) in the presence of 1 mg/mL BSA. Replicate data set is presented in FIGS. 14A-14C, which shows consistent result. (B). *A. baumannii* cell staining examined by microscopy with TAMRA labeled KAM8 at 2 μM for LOS− and 10 μM for LOS+. Scale bar: 10 μm. (C). Percent cell killing of *A. baumannii* (LOS−) with and without photoirradiation. (D). Percent cell killing of the LOS+ versus LOS− strains of *A. baumannii* with 2 μM KAM8-Eosin. The contrasting outcomes of these strains highlight the high strain specificity of KAM8.
Figure 21A:
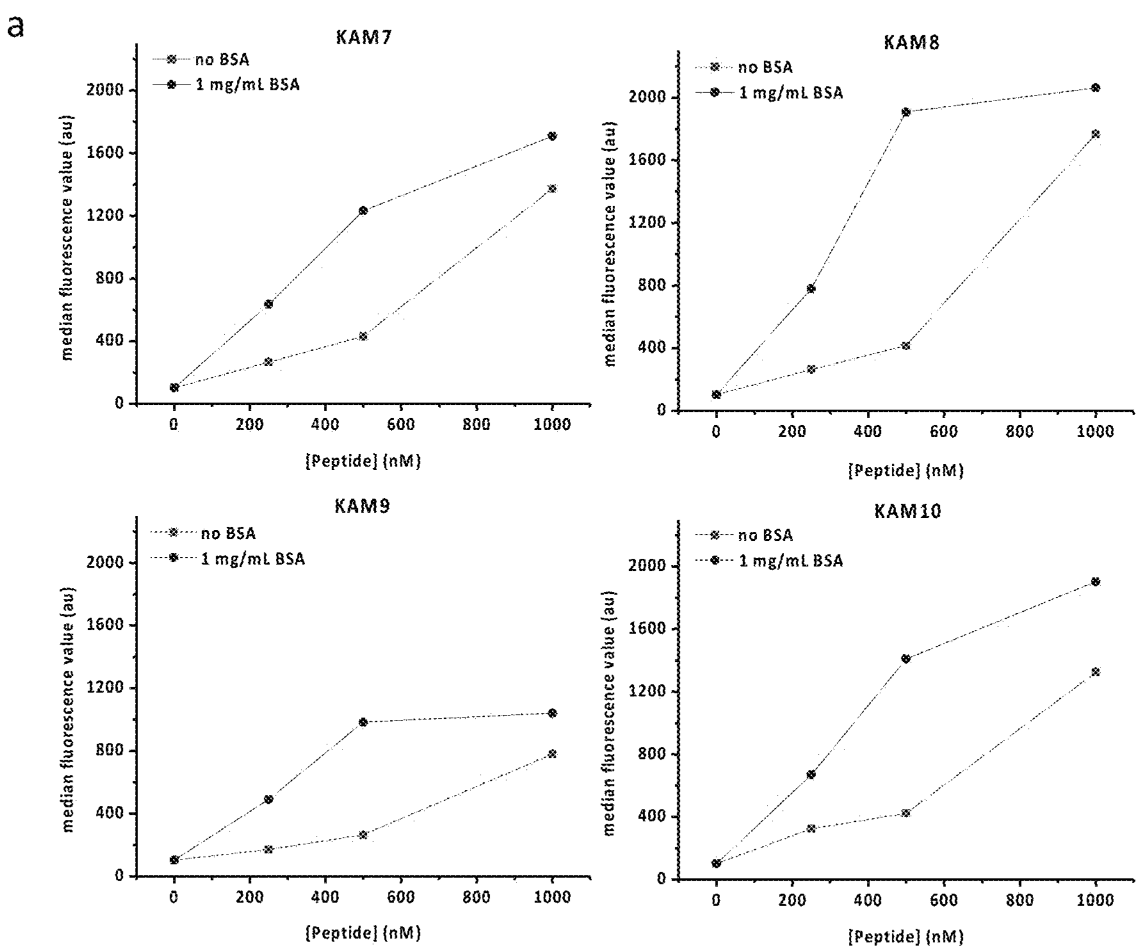
FIGS. 21A-21B show *A. baumannii* (LOS−) staining by KAM7-10. (A) Flow cytometry analysis of KAM7-10 staining of *A. baumannii* (LOS−) in presence and absence of BSA. Fluorescein labeled peptides were used for this analysis. (B) Comparison of *A. baumannii* (LOS−) staining by KAM8 to KAM8-Cyclic (precursor of KAM8, no APBA conjugated) and a naive APBA dimer KAM6 at 1 μM in the presence of 1 mg/mL BSA.
Figure 21B:
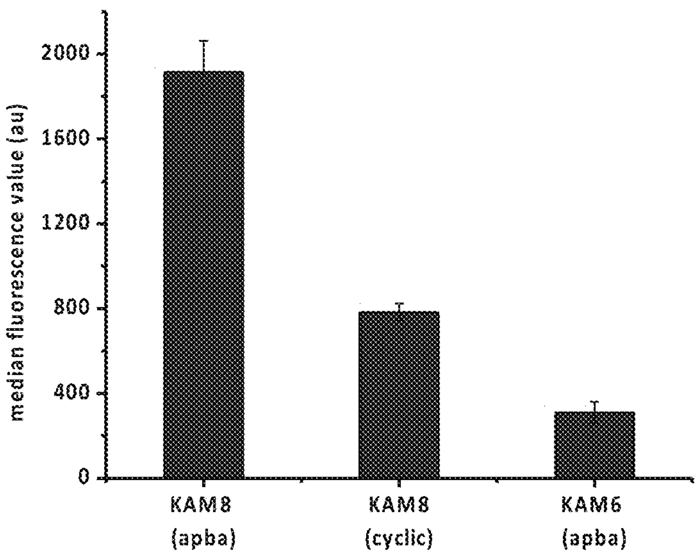
Figure 22:
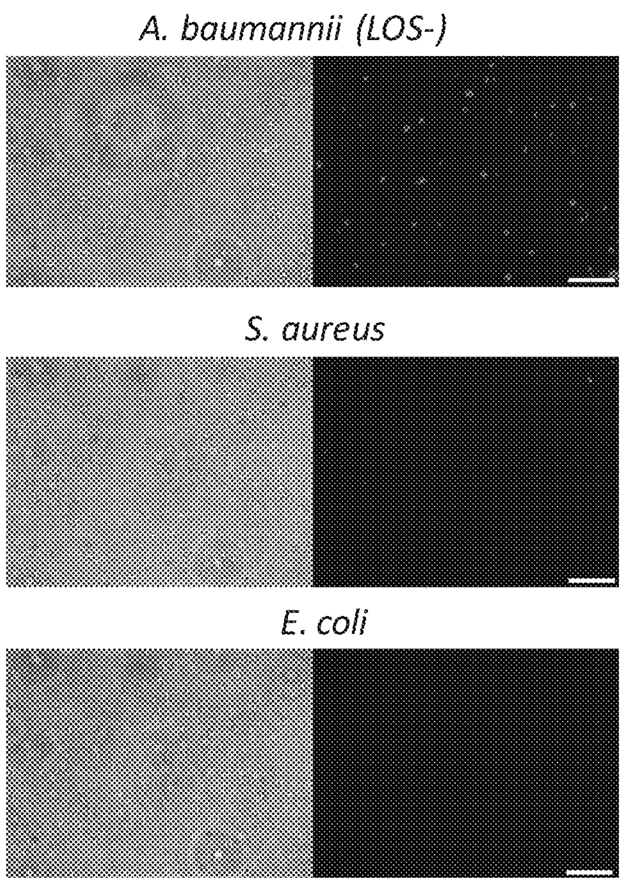
FIG. 22 shows fluorescence microscopy studies of KAM8 (2 μM) staining several bacterial species. TAMRA labeled peptide was used for this study. All samples contain 1 mg/mL BSA. Scale bar: 10 μm.

The APBA-dimer library was panned against a colistin-resistant strain of *A. baumannii*. *A. baumannii* has emerged as a major healthcare-associated pathogen, which can cause severe infections in lungs and blood. *A. baumannii* often presents resistance to multiple antibiotics, sometimes even to colistin (polymyxin E), one of the last-resort antibiotics for its treatment. *A. baumannii* can acquire colistin resistance by modifying its lipooligosaccharide (LOS) with the addition of phosphoethanolamine or 4-aminoarabinose functionalities. Some strains even shut down LOS biosynthesis completely and replace the exterior leaflet of the outer membrane with lipoproteins. The APBA-dimer library on phage was screened against a LOS− mutant of *A. baumannii* (AB5075, a highly virulent isolate established as a model strain for *A. baumannii* infection). Three rounds of panning against the LOS-*A. baumannii* were executed following the same panning procedure described above for *S. aureus* except the addition of a negative screen against the wild-type (LOS+) *A. baumannii* in the second round. After each round of panning, 15 colonies were isolated from the output population and subjected to sequencing, in which convergence was detected starting in round 2 (Table 7). Four different peptide sequences (KAM7-10) were observed repeatedly and synthesized via solid-phase peptide synthesis following the same procedure used for the *S. aureus* binding peptides (Table 8). Flow cytometry analysis of the peptide hits showed potent binding at sub-μM concentrations (FIG. 5A, FIGS. 21A-21B). Similar to what was observed for *S. aureus*, the presence of BSA did not inhibit the peptides' binding to the bacteria. Instead, it actually enhanced bacterial staining by KAM8 at sub-μM concentrations to some extent (FIG. 5A). Analysis of the concentration profile of the bacterial staining by KAM8 gave an estimated $EC_{50}$ of ~0.3 μM. Also similar to the *S. aureus* binders, KAM8 binding to *A. baumannii* requires both the two APBA warheads as well as the specific peptide sequence in between. The negative controls (KAM6 and the cyclic precursor KAM8-Cyclic) showed much reduced binding to the bacteria (FIGS. 21A-21B). The flow cytometry results were further corroborated with fluorescence microscopy studies, which showed bright fluorescence staining of the LOS− *A. baumannii* with 2 μM KAM8 (FIG. 5B). Excitingly, KAM8 stained the bacteria in a strain-specific manner: as seen in the microscopic images, the wild type *A. baumannii* (LOS+) showed little fluorescence staining under the same conditions that gave strong fluorescence staining of the LOS− strain. Comparative analysis of the strains with flow cytometry gave results consistent with the microscopy studies (FIG. 5A). As expected, KAM8 showed no binding to *S. aureus* or *E. coli*, which were used as controls to represent gram-positive and gram-negative bacteria respectively (FIG. 22).

Table 7 below shows sequences (SEQ ID NOS: 190-251, respectively, in order of columns) of the peptide hits obtained from screening the APBA-dimer library against *A. baumannii* (a) from round 2. (b) from round 3. (c) recurring sequences and frequency.

| a | | |
|---|---|---|
| Hit # | DNA Sequence | Peptide Sequence |
| 1 | GCTTGTATTCCGACTCATGCTAATTCGTGC | ACIPTHANSC |
| 2 | GCTTGTACGTTGCCGAATGGGCCTAGGTGC | ACTLPNGPRC |
| 3 | GCTTGTGAGCCGGGGCTGGCGAGGTTTTGC | ACEPGLARFC |
| 4 | GCTTGTACGTTGCCGAATGGGCCTAGGTGC | ACTLPNGPRC |
| 5 | GCTTGTACGTTGCCGAATGGGCCTAGGTGC | ACTLPNGPRC |
| 6 | GCTTGTATTCCGACTCATGCTAATTCGTGC | ACIPTHANSC |
| 7 | GCTTGTAAGCTGTCGGGTCATGCGCCTTGC | ACKLSGHAPC |
| 8 | GCTTGTAAGCATTTGCCGGCGCCGAATTGC | ACKHLPAPNC |
| 9 | GCTTGTAAGCTGTCGGGTCATGCGCCTTGC | ACKLSGHAPC |
| 10 | GCTTGTACGTTGCCGAATGGGCCTAGGTGC | ACTLPNGPRC |
| 11 | GCTTGTACGTTGCCGAATGGGCCTAGGTGC | ACTLPNGPRC |
| 12 | GCTTGTAATATGCATACGCCTATGGTGTGC | ACNMHTPMVC |

-continued

| | | |
|---|---|---|
| 13 | n/a | Blank |
| 14 | GCTTGTACGTTGCCGAATGGGCCTAGGTGC | ACTLPNGPRC |
| 15 | GCTTGTITGGAGCAGAGGGGGCCGGATTGC | ACLEQRGPDC |

b

| Hit # | DNA Sequence | Peptide Sequence |
|---|---|---|
| 1 | GCTTGTAATATGCATACGCCTATGGTGTGC | ACNMHTPMVC |
| 2 | GCTTGTATTCCGACTCATGCTAATTCGTGC | ACIPTHANK |
| 3 | GCTTGTAATATGCATACGCCTATGGTGTGC | ACNMHTPMVC |
| 4 | GCTTGTAAGCTGTCGGGTCATGCGCCTTGC | ACKLSGHAPC |
| 5 | GCTTGTACGTTGCCGAATGGGCCTAGGTGC | ACTLPNGPRC |
| 6 | GCTTGTATTCCGACTCATGCTAATTCGTGC | ACIPTHANSC |
| 7 | GCTTGTACGTTGCCGAATGGGCCTAGGTGC | ACTLPNGPRC |
| 8 | GCTTGTATTCCGACTCATGCTAATTCGTGC | ACIPTHANSC |
| 9 | GCTTGTAAGCTGTCGGGTCATGCGCCTTGC | ACKLSGHAPC |
| 10 | GCTTGTACGTTGCCGAATGGGCCTAGGTGC | ACTLPNGPRC |
| 11 | GCTTGTACGTTGCCGAATGGGCCTAGGTGC | ACTLPNGPRC |
| 12 | GCTTGTACGTTGCCGAATGGGCCTAGGTGC | ACTLPNGPRC |
| 13 | GCTTGTATTCCGACTCATGCTAATTCGTGC | ACIPTHANSC |
| 14 | GCTTGTACGTTGCCGAATGGGCCTAGGTGC | ACTLPNGPRC |
| 15 | GCTTGTATTCCGACTCATGCTAATTCGTGC | ACIPTHANSC |

c

| Peptide Sequence | Round 2 Frequency | Round 3 Frequency |
|---|---|---|
| ACIPTHANSC | 2 | 5 |
| ACTLPNGPRC | 6 | 6 |
| ACKLSGHAPC | 2 | 2 |
| ACNMHTPMVC | 1 | 2 |

Table 8 below shows synthesized peptide hits for *A. baumannii* (LOS−) hits binding (SEQ ID NOS: 252-265, respectively, in order of appearance). Shown are sequences and mass-spec data prior to (a) and after (b) APBA-IA labeling.

a

| NAME | PEPTIDE SYNTHESIZED | Calculated mass | Observed mass |
|---|---|---|---|
| KAM7 | ACIPTHANSCGGGDap* | 1631.73 $[M+H]^+$ | 1631.58 $[M+H]^+$ |
| KAM8 | ACTLPNGPRCGGGDap* | 1645.65 $[M+H]^+$ | 1645.63 $[M+H]^+$ |
| | ACTLPNGPRCGGGDap* | 1700.76 $[M+H]^+$ | 1700.74 $[M+H]^+$ |
| | ACTLPNGPRCGGGDap* | 1961.29 $[M+H]^+$ | 1961.28 $[M+H]^+$ |
| | ACTLPNGPRCGGGDap(aloc) | 1371.63 $[M+H]^+$ | 1371.60 $[M+H]^+$ |
| KAM9 | ACKLSGHAPCGGGDap* | 1601.75 $[M+H]^+$ | 1601.60 $[M+H]^+$ |
| KAM10 | ACNMHTPMVCGGGDap* | 1721.93 $[M+H]^+$ | 1721.56 $[M+H]^+$ |

-continued

| b | | | |
|---|---|---|---|
| | PEPTIDE SYNTHESIZED | Calculated mass | Observed mass |
| KAM7 | $AC_mIPTHANSC_mGGGDap*$ | 1083.45 $[M-H_2O+H]^{2+}$ | 1083.90 $[M-H_2O+H]^{2+}$ |
| KAM8 | $AC_mTLPNGPRC_mGGGDap*$ | 1091.48 $[M-H_2O+H]^{2+}$ | 1091.92 $[M-H_2O+H]^{2+}$ |
| | $AC_mTLPNGPRC_mGGGDap*$ | 1109.49 $[M-2H_2O+H]^{2+}$ | 1109.98 $[M-2H_2O+H]^{2+}$ |
| | $AC_mTLPNGPRC_mGGGDap*$ | 1258.30 $[M-H_2O+H]^{2+}$ | 1258.26 $[M-H_2O+H]^{2+}$ |
| | $AC_mTLPNGPRC_mGGGDap$(aloc) | 1925.77 $[M-H_2O+H]^{+}$ | 1925.83 $[M-H_2O+H]$ |
| KAM9 | $AC_mKLSGHAPC_mGGGDap*$ | 1078.46 $[M+H]^{2+}$ | 1078.41 $[M+H]^{2+}$ |
| KAM10 | $AC_mNMHTPMVC_mGGGDap*$ | 1129.44 $[M-2H_2O+H]^{2+}$ | 1129.39 $[M-2H_2O+H]^{2+}$ |

Dap*: FAM labeled; Dap*: TAMRA labeled; Dap*: Eosin labeled peptides.
Cm: APBA-IA modified cysteine The feasibility of converting KAM8 into a targeted antibiotic for the LOS− strain of *A. baumannii* was further examined. Toward this end, the KAM8-Eosin conjugate was synthesized, which upon photoirradiation effectively killed the LOS− *A. baumannii* cells (2 μL, 15 min light, >90% cell killing, FIG. 5C). In contrast, eosin alone at these concentrations did not elicit *A. baumannii* cell death nor did KAM8 without the photosensitizer. KAM8-Eosin was established as a strain-specific antibiotic of the LOS− *A. baumannii* as it demonstrated little killing of the wild-type (LOS+) strain under the same conditions (FIG. 5D). Collectively, these data showcase that strain-specific bacterial cell killing can be achieved through phage display and selection of the APBA-presenting peptides.

Example 11

Develop Novel Phage Libraries to Target Specific Strains of Bacteria

Additional phage libraries can be developed for the following reasons: 1) given the vast variations between bacterial species and strains, having a collection of phage libraries can maximize the chance of success for identifying specific probes for new emerging strains of pathogens; 2) as shown in the present invention, screening of the APBA dimer library was able to give bacterial cell binders with low to sub μM potency. While these are on par with the Minimal Inhibitory Concentration (MIC) of many clinically used antibiotics, improving their potency can reduce the toxicity of the peptide-antibiotic conjugates for in vivo applications. For example, higher potency of peptide-colistin conjugates may avoid the well-known nephrotoxicity of the colistin itself; 3) peptide libraries of cyclic scaffolds are expected to yield improved biostability against protease degradation.

Monocyclic Peptide Library

Figures 23A, 23B:
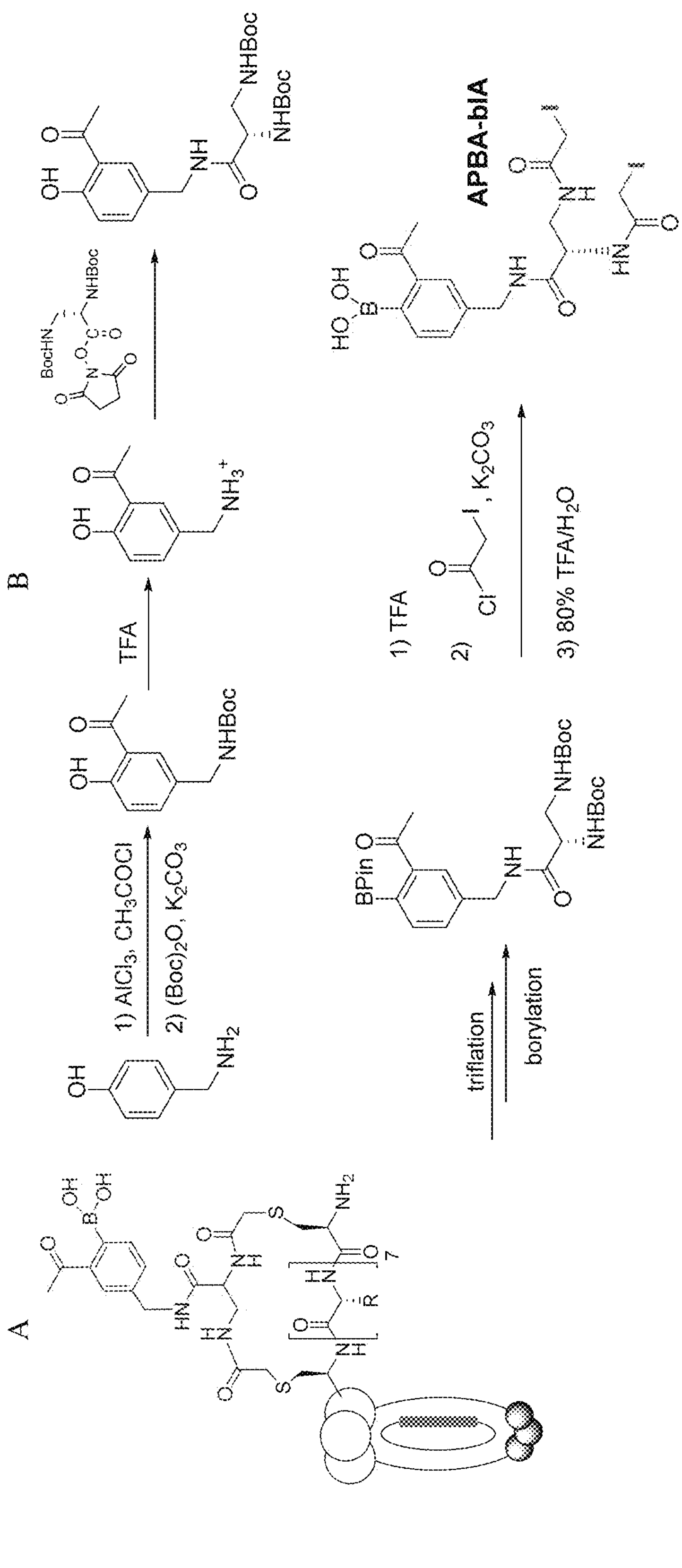
FIGS. 23A-23B show (A) phage displayed cyclic peptides carrying 2-APBA warhead and (B) a proposed route for synthesis of APBA-bIA.

In comparison to their linear counterparts, cyclic peptides are attractive as they often exhibit enhanced resistance toward protease cleavage. In addition, the cyclic scaffold can preorganize the molecule for target binding as well. A monocyclic peptide library can be readily constructed by treating the reduced C7C library with a bis-iodoacetamide (bIA) derivative, which reacts with the reduced cysteine side chains to give a cyclic product (FIG. 23A). The bIA derivative (APBA-bIA, FIG. 23B) can then be synthesized to incorporate 2-APBA as a reversible covalent warhead. To ensure peptide cyclization instead of bis-alkylation, a model C7C peptide can be used to determine the optimal concentration and conditions needed for phage modification. The success of 2-APBA incorporation can be confirmed with semicarbazide ligation as was demonstrated in FIGS. 1B-1D for the APBA dimer library.

Bicyclic Peptide Library

Phage displayed bicyclic peptide libraries that display reversible covalent warheads can also be developed. There has been a long-lasting interest in multicyclic compounds in medicinal chemistry. While a large body of literature exists for monocyclic peptides, synthesis of multicyclic peptides remains nontrivial. It had not been possible to display multicyclic peptides on phage until only a few years ago. The elegant work by Heinis et al. allowed the display of bicyclic peptides by crosslinking three cysteine residues that are strategically incorporated into the phage-displayed peptides. Currently, this remains the only method for presenting and evaluating multicyclic peptide libraries via phage display. Unfortunately, the Heinis system is less ideal for several reasons. First, the engineered M13 phage exhibit slow kinetics to infect *E. coli* for amplification, which is problematic as it gives growth advantage to the unmodified phage. Secondly, the simultaneous crosslinking of three cysteine residues makes it difficult to incorporate any additional binding motifs, such as the 2-APBA warhead, to better promote target binding.

Figure 24A:
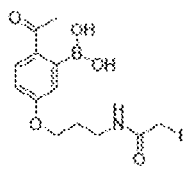
FIGS. 24A-24B show iminoboronate-mediated peptide cyclization and bicyclization. (A) APBA-IA that can be used for modification of a Cys side-chain. (B) Example of peptide bicyclization with between each of two Cys residues modified with APBA-IA and each of two Lys pairs strategically placed in the peptide sequence (SEQ ID NO: 282). For each of the Cys and Lys residues in the peptide sequence shown, the side chains for each are discretely shown to provide detailed information on the interactions and reactions involved in the bicyclization reaction.
Figure 24B:
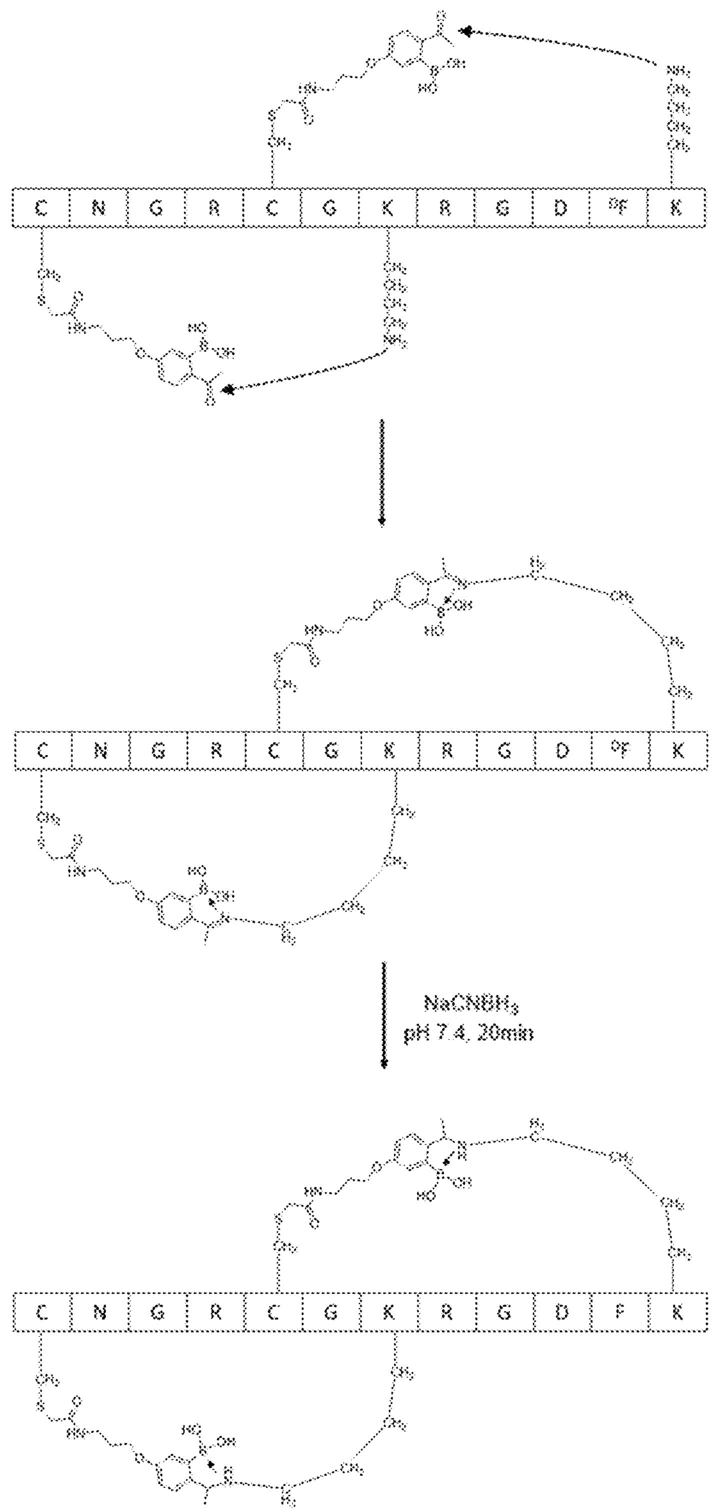

A powerful strategy has recently been reported that allows for spontaneous cyclization and bicyclization of peptides under physiologic conditions (FIGS. 24A-24B). Specifically, the dynamic and thermodynamically controlled conjugation of AB3 and lysine affords spontaneous peptide cyclization. Importantly, regioselective bicyclization can be accomplished with strategic incorporation two AB3-Lys pairs, one of which resides in an (AB3)XK motif. As the (AB3)XK motif does not allow cyclization within itself due to steric constraints, peptides are able to bicyclize to give a single regioisomer. The iminoboronate linkage, although dynamic under physiologic conditions, can be rapidly and quantitatively reduced with $NaCNBH_3$ to afford permanent cyclization. Reduction of the iminoboronate linkage gives an ortho-aminomethyl-phenyl boronic acid moiety, which potentially forges an even stronger dative bond than that of iminoboronates. Supporting this notion, literature data show that ortho-boronic acid substituted benzyl amines can only be protonated at pH 2 or lower, while secondary amines typically display pKa values over 10. The strong B—N dative bond may render structural rigidity to the bicyclic peptides, which is an intrinsic advantage of this iminoboronate-based bicyclization strategy.

Figure 25:
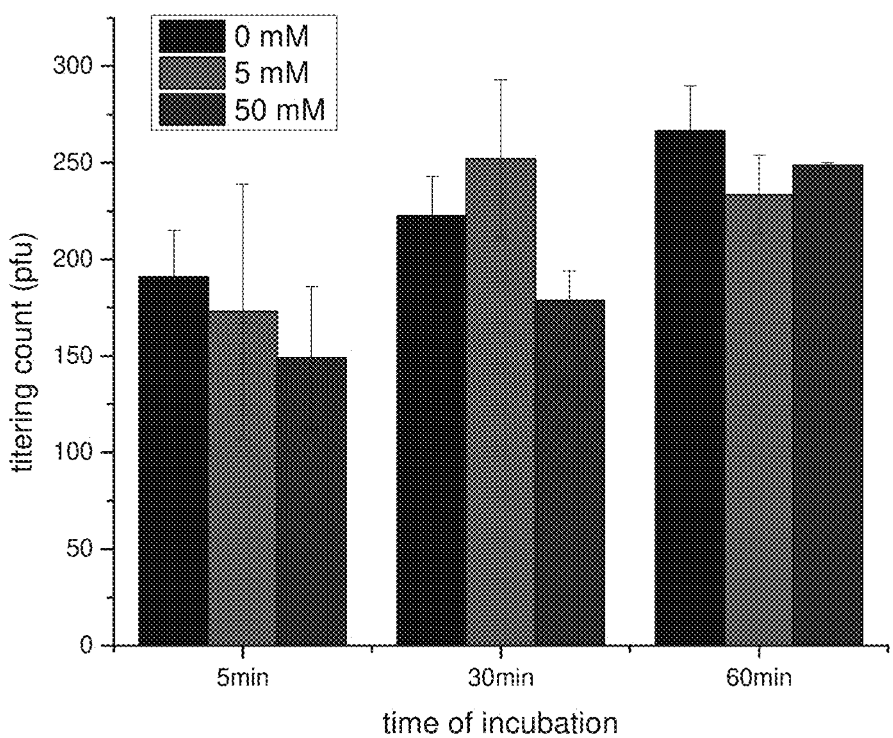
FIG. 25 shows titering results of M13 phage treated with $NaCNBH_3$ of varied concentration and time. The results indicate that the $NaCNBH_3$ treatment minimally compromises the phage's viability.

The iminoboronate-mediated bicyclization can be implemented on phage, which can yield a novel bicyclic peptide library. It is important to note that the iminoboronate-bicyclized peptides could still allow subsequent introduction of 2-APBA as a reversible covalent warhead to bind biological amines. Peptide bicyclization can be realized on phage by incorporating 2-APBA-lysine pairs at appropriate positions. Given reduction of iminoboronates is needed to afford the final permanently cyclized peptides, whether the M13 phage could survive the $NaCNBH_3$ treatment was first tested. Titering results (FIG. 25) show that the phage library treated with $NaCNBH_3$ gives comparable colony count to the untreated control, indicating the M13 phage is able to survive the $NaCNBH_3$ treatment without significant damage.

Figure 26:
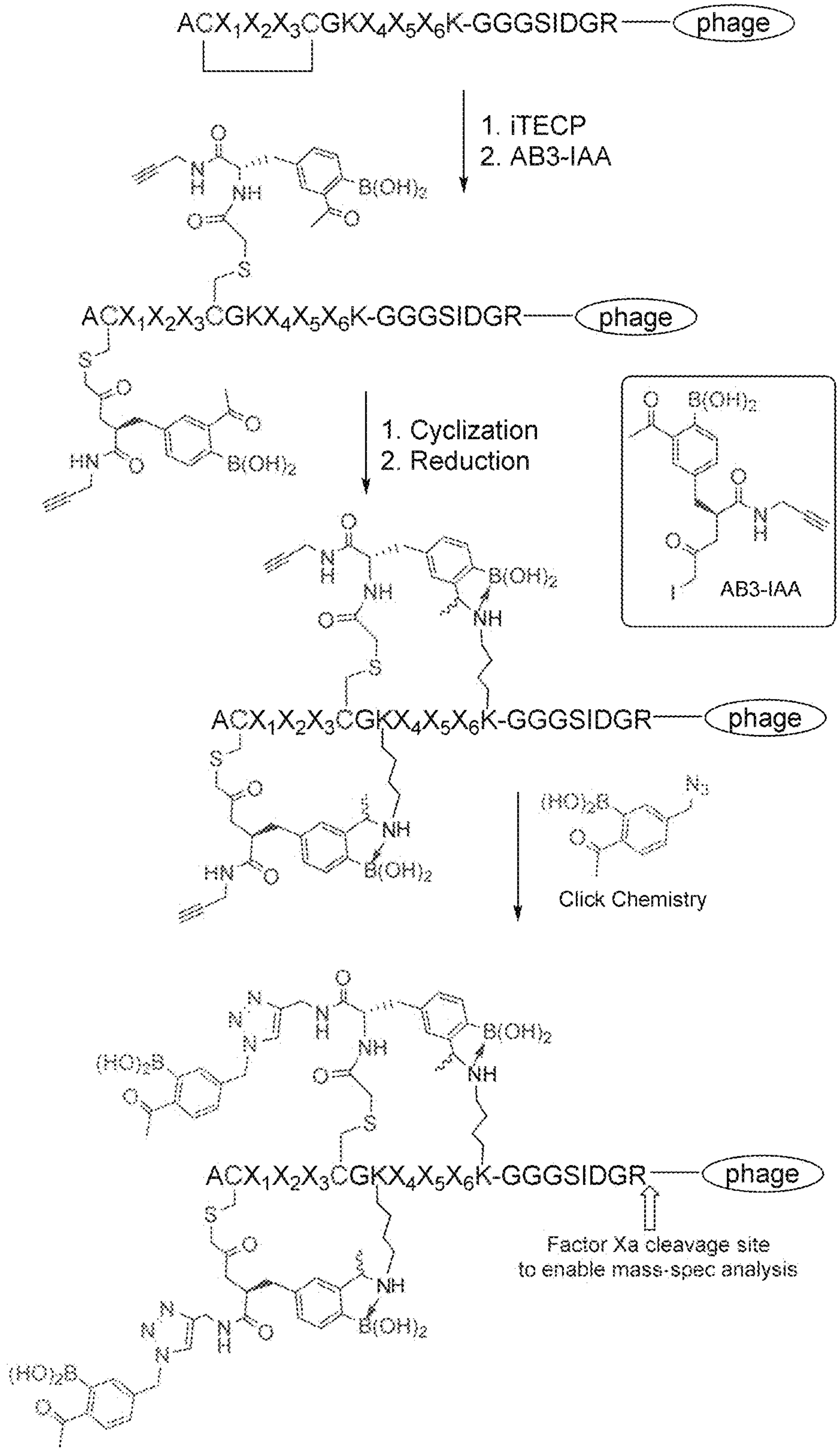
FIG. 26 shows peptide bicyclization and further functionalization on phage (SEQ ID NOS 278-281, respectively, in order of appearance).

To realize peptide bicyclization on phage, an iodoacetamide derivative of AB3, AB3-IAA (FIG. 26) can be synthesized, which can alkylate cysteine on phage analogous to APBA-IA. The side chain of the cysteine conjugate of AB3-IAA (named herewith as "CAB3") can crosslink with a proximal lysine to give peptide cyclization. Importantly, the design of AB3-IAA incorporates an alkyne handle to enable further functionalization of the bicyclized peptides on phage. Phage libraries can be created to display peptides with the sequence of $ACX_1 \ldots X_nCGKX_{n+1} \ldots X_{n+m}K$ (SEQ ID NO: 270). The randomized residues between the two cysteine residues can vary from 1 to 4 (n: 1-4). Similarly, the randomized residues between the two lysines can vary from 1 to 4 as well (m: 1-4). An exemplary sequence is shown in FIG. 26 with n, m=3.

According to the preliminary results, these sequence designs are likely to afford efficient formation of intramolecular iminoboronates. To further test this notion, first, a group of representative sequences (m, n=1, 2, 3, 4) can be synthesized to probe the bicyclization efficiency and regioselectivity. The AB3-IAA moiety can be conjugated to the cysteines under standard thiol-iodoacetamide labeling conditions. For the initial set of peptides, all varying residues can be set to be alanines. The efficiency and regioselectivity of bicyclization can be assessed by using LC-MS and NMR analysis. Peptides with m, n=3 or 4 can fully bicyclize to give single products; the shorter peptides might run into complications in bicyclization due to steric constraints. An additional complication might result from the side chain flexibility of CAB3, which is longer and more flexible than that of AB3. The increased side chain flexibility might allow it to crosslink with either one of the two lysines in the peptide sequence. Should that be the case, the central glycine in the CGK segment can be eliminated. Alternatively, the glycine residue could be replaced with a proline, which might effectively prevent cyclization within the (CAB3)PK segment.

Figure 1C:
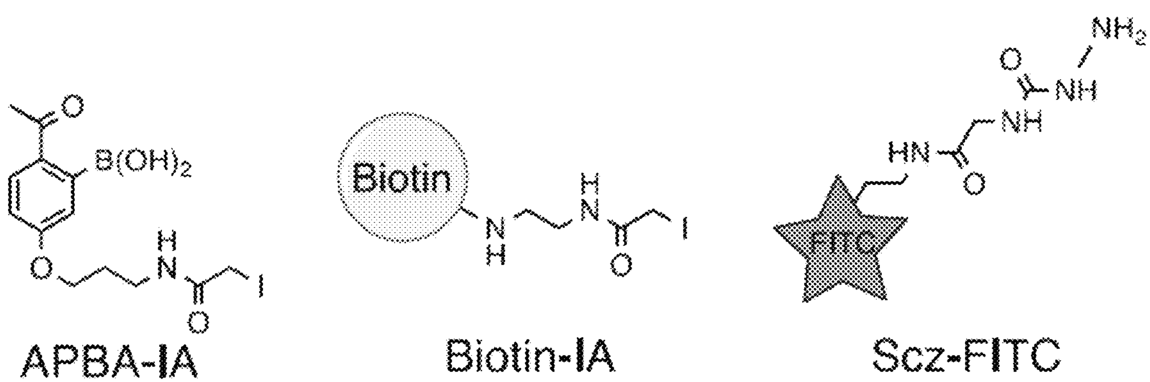
Figure 1D:
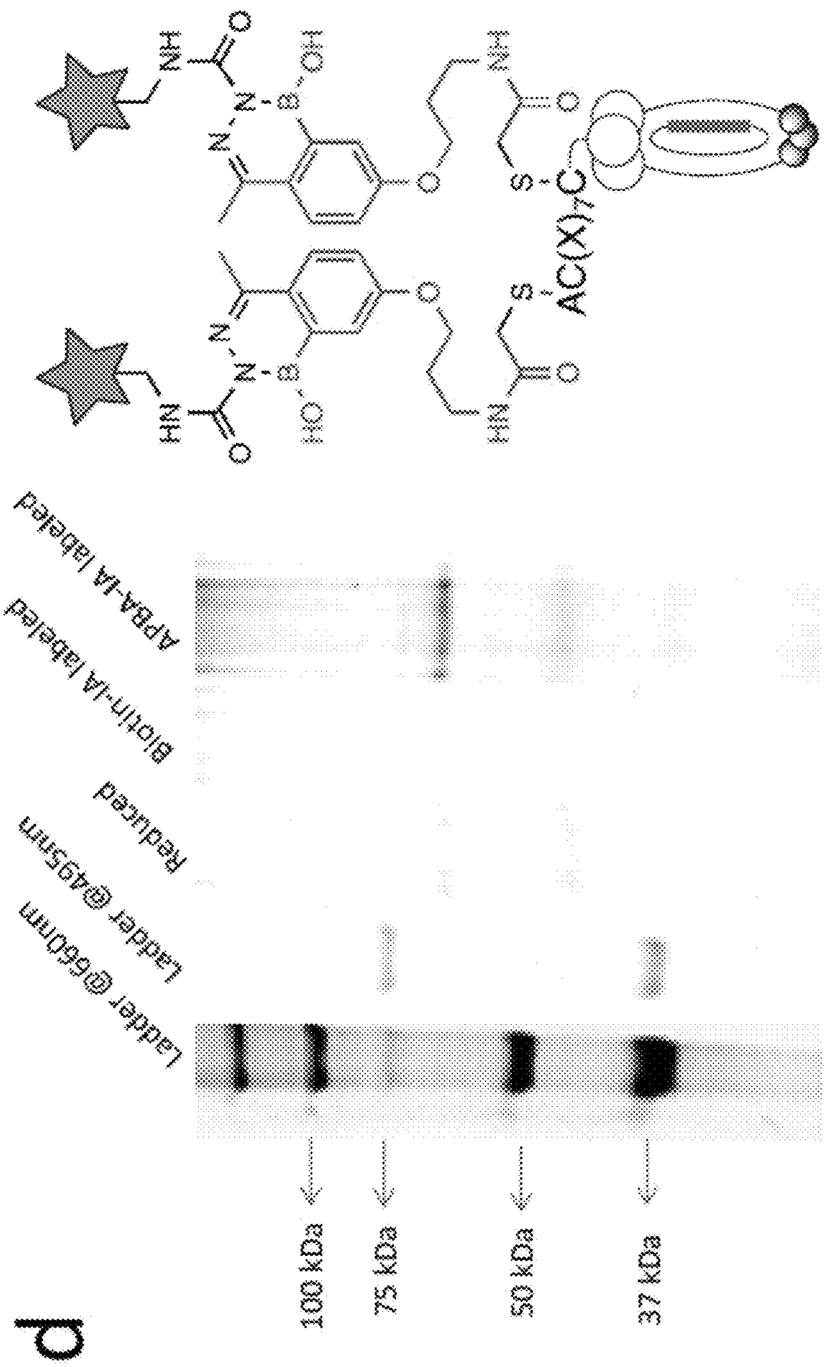

The peptide sequences that are confirmed to undergo facile bicyclization can be introduced to the N-terminus of the pIII protein using the Peptide Display Cloning System from New England Biolabs. To introduce the randomized residues, the NNC codon set can be used, which allows for the incorporation of 15 amino acids. The choice of NNC codon is to exclude lysine from the randomized positions, which may cause complications to the regioselective bicyclization as expected for the chosen peptide sequence. An eight-residue spacer (GGGSIDGR (SEQ ID NO: 266, FIG. 26) can be further introduced between the displayed peptide and the pIII protein. This design can place the cysteine residues, which can later be converted to CAB3 residues, distant enough from the pIII protein so that the 2-APBA moieties are not crosslink with native lysine residues of the phage (iminoboronate formation is reversible and distance dependent). Importantly, this spacer sequence incorporates a factor Xa cleavage site (IDGR (SEQ ID NO: 267)), which can allow the peptide to be cleaved off phage for mass-spec analysis. The phage library with the designed peptide sequences can be subjected to reduction and labeling with AB3-IAA. The completeness of labeling can be confirmed with the established protocol used to characterize the APBA dimer library as shown in FIGS. 1B-1D. Then the AB3-IAA labeled phage can be subjected to $NaCNBH_3$ reduction to afford peptide bicyclization on phage. The bicyclic peptide library can then be tested for infectivity and amplification efficiency through titering. The peptide bicyclization on phage can be further confirmed via large scale preparation of a bicyclized phage, which can be treated with factor Xa and subjected to mass-spec analysis.

Once peptide bicyclization is established on phage, a pair of 2-APBA moieties can be installed through the azide-alkyne click chemistry. The azido derivative of 2-APBA shown in FIG. 26 can be made by derivatizing 2-acetyl-4-aminomethyl-phenol, an intermediate of APBA-bIA synthesis as shown in FIG. 23B. Conversion of the amine to azide followed by triflation and borylation can give the desired product for phage modification. The success of click chemistry can be validated with mass-spec analysis of the factor Xa cleaved peptides.

Example 12

Comparative Evaluation of the Phage Libraries for Bacterial Binding

The utility of the constructed phage libraries can be assessed by screening for potent bacterial binders in comparison to the APBA dimer library. The screening can be performed using *S. aureus* and *A. baumannii* (LOS−) as the initial set. The screening can be performed following the same protocol used for the APBA dimer library. The peptide hits obtained from the cyclic peptide libraries can be synthesized by using similar protocols as developed for KAM5 and KAM8 synthesis. With fluorophore labeling, the peptide hits can be assessed for bacterial cell binding with florescence microscopy and flow cytometry. The potency of the cyclic peptide hits can be compared to those identified from the APBA dimer library.

In addition to the bacterial binding potency, the serum stability of the peptide hits from different phage libraries can be comparatively examined, and can be performed by using a standard protocol. Briefly, the fluorophore labeled peptides can be incubated with human blood serum and the percentage of intact peptides can be assessed by HPLC over time. The cyclic peptide hits, particularly the bicyclic peptide hits, are anticipated to show longer half-life in human serum.

Example 13

Testing the General Applicability of the Phage Libraries

The general applicability of the phage display platform can be probed by examining a panel of bacterial species and strains. For gram-positive bacteria, in addition to *S. aureus*, a library screening can be performed against *Streptococcus pneumoniae*, which causes over 1.2 million drug resistant infections annually in the US. A daptomycin insensitive and a daptomycin-sensitized strain can be screened against in parallel for comparison. A recent publication indicates the significance of genes responsible for cell wall integrity in daptomycin sensitivity, although the chemical and structural basis of daptomycin resistance as well as its mode of action remains unclear. The peptide hits identified can be tested for binding the *S. pneumoniae* strains as well as for binding *S. aureus* for comparison. The comparative study could reveal the bacterial binding potency and specificity of the peptide hits.

Figure 31:
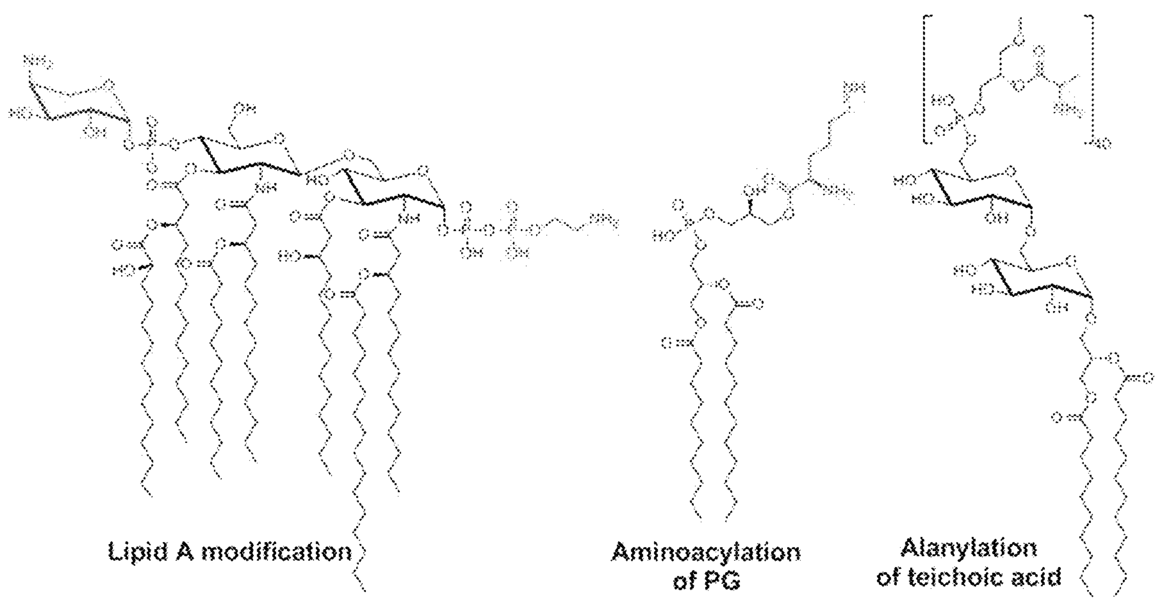
FIG. 31 shows the lipid modifications (with amines) that give rise to antibiotic resistance.

For gram-negative bacteria, in addition to the LOS-strain of *A. baumannii*, the library screening can be extended to the wild type *A. baumannii* (AB5075, LOS+), as well as several additional gram-negative pathogens including *E. coli, K. pneumoniae*, and *P. aeruginosa*. While not having a protein-coated surface, these gram-negative bacteria could be targeted by a peptide probe binding specific outer membrane proteins. This is possible given that POL7080, a targeted antibiotic for *P. aeruginosa* currently in clinical trials, was developed to specifically bind and inhibit the lipopolysaccharide transport protein LptD with nanomolar potency. In addition to the outer membrane proteins, gram-negative bacteria often display phosphoethanolamine modified LOS (or lipopolysaccharide (LPS), as shown in FIG. 31, which elicits colistin resistance. Such modified LOS can be efficiently targeted by iminoboronate-capable peptides, analogous to the *S. aureus* binders.

To test this notion, the phage library screening can be further extended to clinical strains of *A. baumannii* that are colistin-resistant and known to have LOS modifications. Given the success described in the present invention, potent and selective binders can be identified for these particular strains. The peptide hits identified from all the screens can be synthesized, fluorophore labeled, and then examined for binding the target and non-target strains. Comparative studies across this panel of bacteria could give a clear understanding on the scope and limitations of the phage display platform for targeting specific bacteria.

An important aspect of characterizing the peptide hits is to elucidate the molecular targets of the identified peptide probes. The peptide probes are designed to bind bacteria through formation of iminoboronates, which can be readily reduced to yield a permanent linkage. This unique property can allow facile identification of the molecular target(s) of the peptide probes. Toward this end, an alkyne handle can be incorporated through an orthogonally protected Dap, similar to the fluorophore labeling strategy outlined above. $NaCNBH_3$ reduction can be performed on the bacterial cell bound peptides. It is suggested that KAM5 binds *S. aureus* through conjugation with Lys-PG, while KAM8 binds the LOS-*A. baumannii* by targeting the surface lipoproteins. This can be confirmed by crosslinking, enriching and characterizing the peptide-target conjugates through LC/MS/MS analysis. Given the challenge of characterizing lipid-anchored molecules, phospholipase treatment can be performed to cleave the headgroup (e.g., for Lys-PG) or the protein (e.g., for LOS) off the lipid anchor before enrichment and analysis. For bacteria not known to display lipid modifications, a successful peptide probe may bind specific surface proteins. Should biochemical characterization prove to be difficult, genetic tools such as transposon mutagenesis (i.e. Tn-Seq) can be used for target identification. FACS sorting of a transposon library stained by a peptide probe followed by sequencing could inform on the potential target of the probe.

Example 14

Develop Peptide-Antibiotic Conjugates for Effective and Targeted Bacterial Cell Killing The preliminary studies demonstrated the feasibility of converting a bacterium binding peptide to a targeted antibiotic through conjugation and targeted delivery of a bactericidal agent to the intended cells. Peptide-antibiotic conjugates both in vitro and in animal models can be systemically examined to enhance the potency and expand the scope of applications of the peptide-antibiotic conjugates.

Design of Peptide-Antibiotic Conjugates

Figure 27:
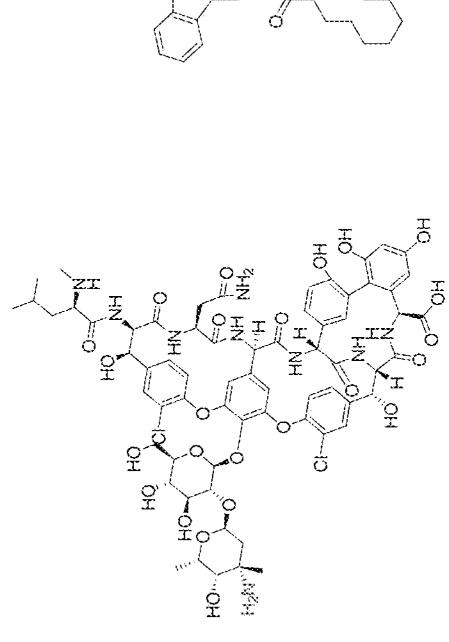
FIG. 27 shows structures of bactericidal agents for conjugation to bacteria-specific peptide probes. Highlighted in red are primary amines that can serve as conjugation site.
Figure 27:
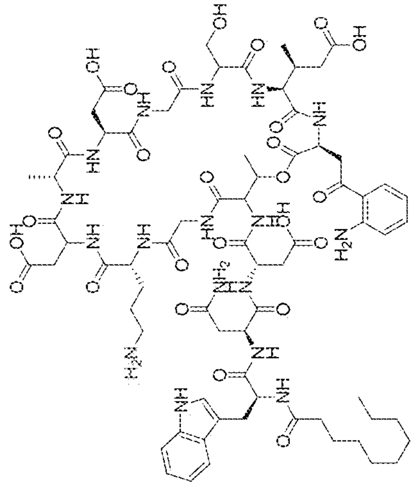
Figure 27:
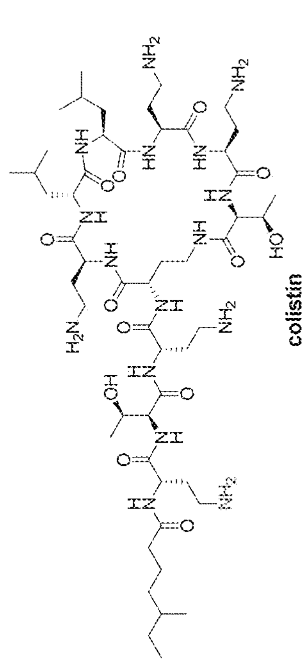
Figure 27:
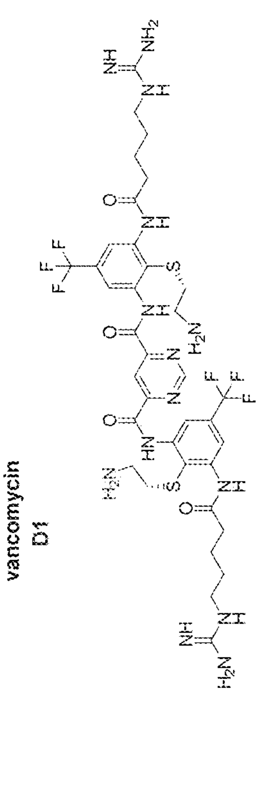
Figure 27:
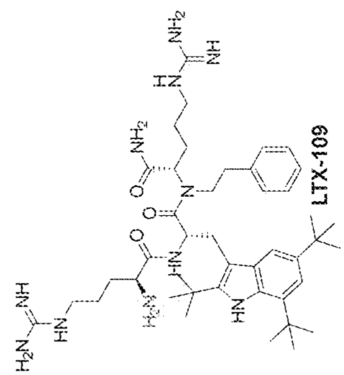
Figure 27:
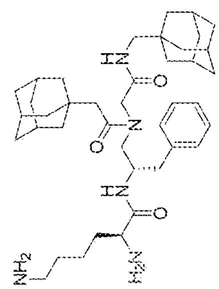
Figure 28:
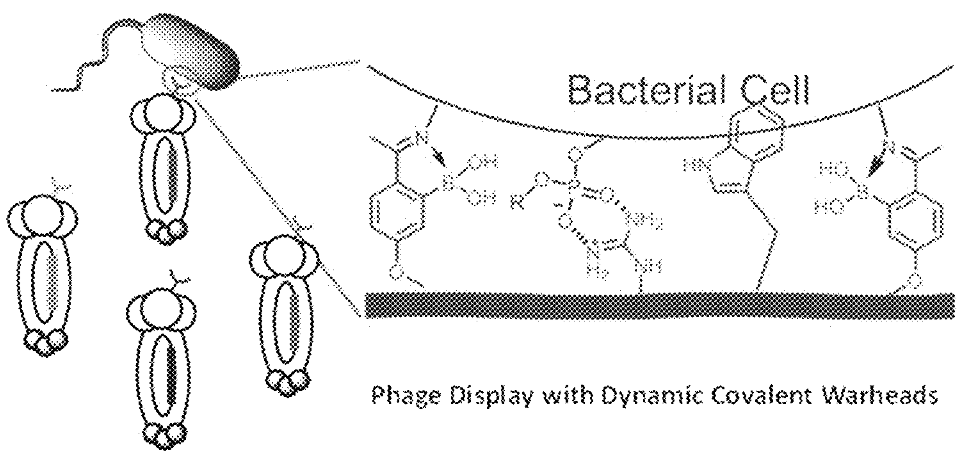
FIG. 28 shows the general concept of phage libraries that display dynamic covalent binding motifs. Such dynamic covalent binding motifs can interact with a biological target through unprecedented mechanisms.
Figure 29A:
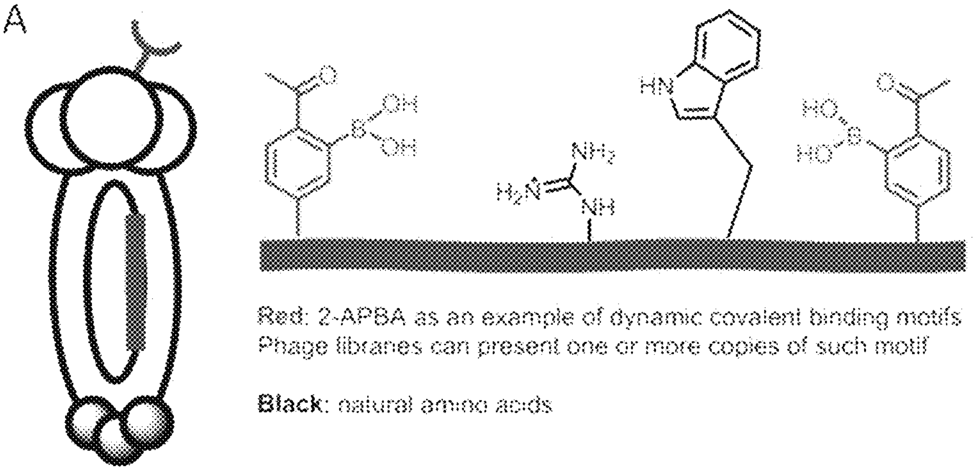
FIGS. 29A-29B show phage modifying molecules that display a carbonyl (C═O) and a boronic acid moiety on adjacent positions. 2-APBA is one example of a dynamic covalent binding motif, as shown in these figures. The molecules engage with a biological target via conjugation to amines (e.g., lysine side chains). Dynamic covalent binding motifs may also bind other functionalities such as cysteine and serine side chains.
Figure 29B:
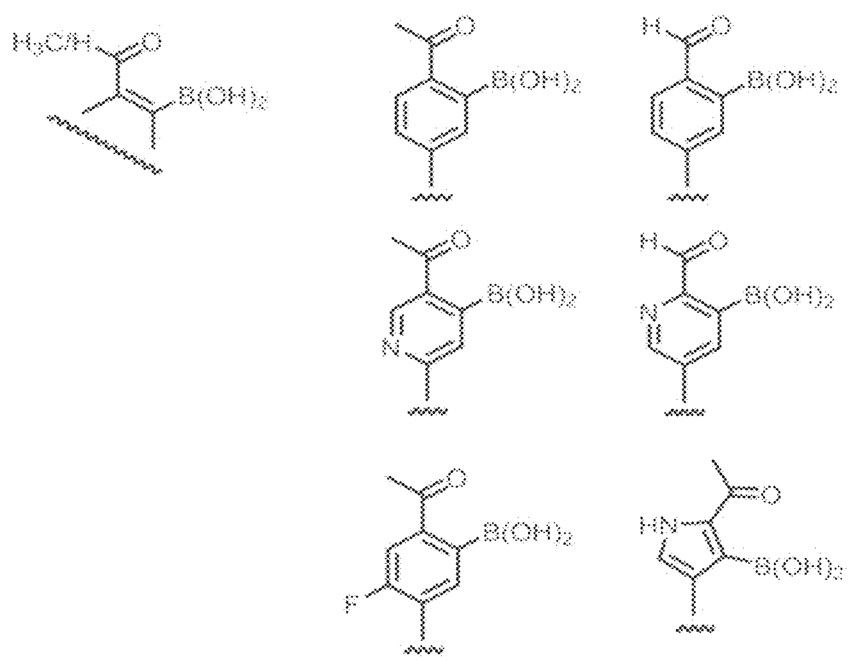
Figure 30:
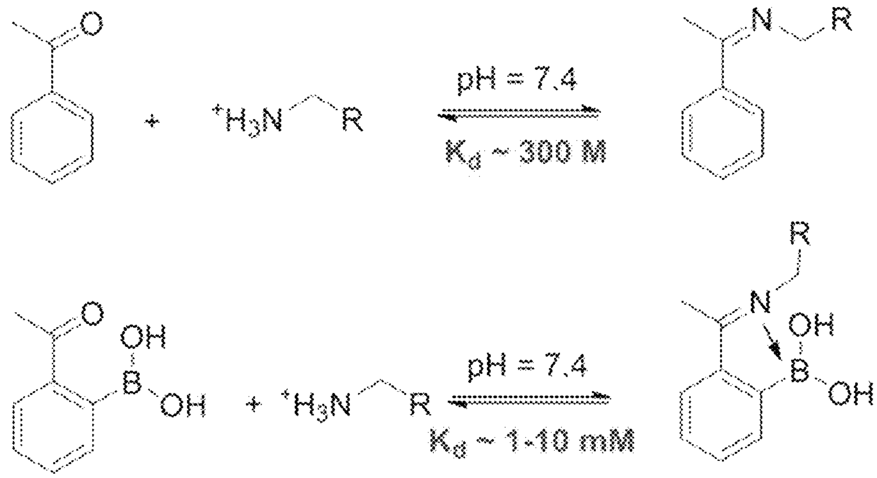
FIG. 30 shows the fundamental properties of dynamic covalent binding. Specifically, it shows the advantage of 2-APBA (in comparison to the control molecule) for binding biological amines with enhanced potency.

For the bactericidal agents, an initial set was chosen to include several mechanistically distinct antibiotics (FIG. 27). As the peptide probes identified from phage display are likely to bind bacterial cell surfaces without cell entry, the focus is on antibiotics that attack the cell envelope (instead of intracellular targets) for bacterial killing. The ease of conjugation to the peptide probes is used as a secondary criteria. Vancomycin (D1) has been utilized in hospitals to treat gram-positive infections for several decades. It inhibits bacterial cell growth by binding to the D-Ala-D-Ala dipeptide segment of the lipid II stem peptide, thereby inhibiting peptidoglycan biosynthesis. Daptomycin (D2), another last-resort antibiotic to treat gram-positive infections, is believed to cause bacterial cell death by binding and disrupting the cell membrane of bacteria. Colistin (D3) was introduced half a century ago and had not been a primary antibiotic due to its nephrotoxicity. However, it has recently re-emerged as a last-resort antibiotic for multidrug-resistant gram-negative infections. Colistin is believed to exert its antibiotic activity by binding to lipid A and lipopolysaccharide (LPS) and subsequently disrupting the membrane of the cells. These antibiotics carry an amino group (H2N in FIG. 27) that has been shown to be non-essential for function and therefore can serve as a handle for conjugation to a directing element.

Further, several synthetic, membrane-disrupting antibiotics in development were also examined. SMAMP-02 (D4) is a structural analogue of brilacidin, an antimicrobial peptide mimic currently in clinical trials. SMAMP-02 is chosen for the studies because of its ease of conjugation and broad-spectrum activity with potency similar to that of brilacidin. LTX-009 (D5) is another membrane-disrupting antibiotic currently in clinical trials. A small peptidomimetic compound appeared in recent literature (D6) was also included for the study because of its potent antibiotic activity and its ease of synthesis. For conjugation, a clickable handle can be installed onto the primary amines of the bactericidal compounds, which can be used to conjugate with a peptide binder of bacteria. Given that azide-alkyne click chemistry is used to introduce the 2-APBA moiety to the bicyclic peptides (FIG. 26), the tetrazine-based bioconjugation chemistries can be chosen for joining the antibiotic and the peptides. Specifically, a tetrazine moiety can be installed onto the peptide probes similar to the fluorophore conjugation protocol described earlier. The antibiotics can be derivatized with a linker and a trans-octene group for tetrazine conjugation. This modular design should allow facile incorporation and assessment of both stable and cleavable (—S—S—) linkers in the peptide-antibiotic conjugates.

Testing Targeted Bacterial Clearance In Vitro and in Animal Models

Targeted antibiotics can be developed via conjugation of a bactericidal agent to a directing peptide that binds specific bacterial strains. The peptide-antibiotic conjugates can be first tested in vitro to determine the MIC values for the panel of bacteria described above. In comparison to the parent antibiotics, the peptide-antibiotic conjugates are expected to gain potency (lowered MIC) toward the target strain, while bypassing other bacteria as well as host cells. Comparative analysis of the MICs across the panel of bacteria can inform on the species and strain specificity. Host cell toxicity can be assessed against red blood cells and additional model cell lines. The vancomycin/daptomycin conjugates shows efficacy against gram-positives, while the colistin conjugates works against gram-negative bacteria. The conjugates of the synthetic antibiotics (D4-6) may show broader applicability with specificity dictated by the directing peptide.

The peptide-antibiotic conjugates showing high potency and selectivity in vitro can be further tested in animal models of bacteremia. The in vivo testing can focus on the infections caused by *S. aureus* and *A. baumannii* due to the continued high mortality of *S. aureus* and the increasing severity of drug resistance shown by *A. baumannii*. For each bacteria, two of the top-performing peptide-antibiotic conjugates identified from in vitro studies can be tested. Briefly, for *S. aureus* infection, NMRI mice aged 5-7 weeks are injected in the tail vein with ~$10^7$ CFUs of bacteria (*S. aureus*: ATCC 43300). One cohort of ten mice is treated with a peptide-antibiotic conjugate, while the control cohort is injected with the vehicle alone for comparison. The dosage and frequency of drug administration are determined empirically through a separate experiment beforehand. Bacterial loads are determined daily for seven days via tail bleeds and subsequent titering and plating of bacteria on agar. To determine whether the peptide-antibiotic conjugate can increase the survival rate, mice are infected with $3*10^8$ CFUs, which typically causes mortality within 100 hours post infection. The same number of mice and treatment groups are used as in the bacterial load experiments. Mice are euthanized when moribund, bacterial loads are determined and time of death post infection is used to construct Kaplan-Meier survival curves. *A. baumannii* infection is modeled through a similar protocol except that ICR mice (6-8 weeks) are used. The successful designs of a peptide-antibiotic conjugate can elicit better bacterial clearance and increase the survival rate of the animals.

REFERENCES

Blair, J. M.; Webber, M. A.; Baylay, A. J.; Ogbolu, D. O.; Piddock, L. J. *Nature rev.,* 2015, 13, 42.

Fischbach, M. A.; Walsh, C. T. *Science,* 2009, 325, 1089.

Modi, S. R.; Collins, J. J.; Relman, D. A. *J. Clin. Invest.,* 2014, 124, 4212.

Lehar, S. M.; Pillow, T.; Xu, M.; Staben, L.; Kajihara, K. K.; Vandlen, R.; DePalatis, L.; Raab, H.; Hazenbos, W. L.; Morisaki, J. H.; Kim, J.; Park, S.; Darwish, M.; Lee, B. C.; Hernandez, H.; Loyet, K. M.; Lupardus, P.; Fong, R.; Yan, D.; Chalouni, C.; Luis, E.; Khalfin, Y.; Plise, E.; Cheong, J.; Lyssikatos, J. P.; Strandh, M.; Koefoed, K.; Andersen, P. S.; Flygare, J. A.; Wah Tan, M.; Brown, E. J.; Mariathasan, S. *Nature,* 2015, 527, 323.

Mariathasan, S.; Tan, M. W. *Trends Mol. Med.* 2017, 23, 135.

Kumaresan, P. R.; Wang, Y.; Saunders, M.; Maeda, Y.; Liu, R.; Wang, X.; Lam, K. S. *ACS Comb. Sci.,* 2011, 13, 259.

Qian, Z.; Upadhyaya, P.; Pei, D. *Methods Mol. Biol.,* 2015, 1248, 39.

Jagadish, K.; Gould, A.; Borra, R.; Majumder, S.; Mushtaq, Z.; Shekhtman, A.; Camarero, J. A. *Angew. Chem. Int. Ed.,* 2015, 54, 8390.

Owens, A. E.; de Paola, I.; Hansen, W. A.; Liu, Y.-W.; Khare, S. D.; Fasan, R. *J. Am. Chem. Soc.,* 2017, 139, 12559.

Hamzeh-Mivehroud, M.; Alizadeh, A. A.; Morris, M. B.; Church, W. B.; Dastmalchi, S. *Drug. Discov. Today,* 2013, 18, 1144.

Huang, J. X.; Bishop-Hurley, S. L.; Cooper, M. A. *Antimicrob. Agents Chemother.,* 2012, 56, 4569.

Ng, S.; Jafari, M. R.; Derda, R. *ACS Chem. Biol.,* 2012, 7, 123.

Mohan, K.; Weiss, G. A. *ACS Chem. Biol.,* 2016, 11, 1167.

Day, J. W.; Kim, C. H.; Smider, V. V.; Schultz, P. G. *Bioorg. Med. Chem. Lett.,* 2013, 23, 2598.

Heinis, C.; Rutherford, T.; Freund, S.; Winter, G. *Nat. Chem. Biol.,* 2009, 5, 502.

Ng, S.; Jafari, M. R.; Matochko, W. L.; Derda, R. *ACS Chem. Biol.,* 2012, 7, 1482.

Bandyopadhyay, A.; Gao, J. *Curr. Opin. Chem. Biol.,* 2016, 34, 110.

Bandyopadhyay, A.; McCarthy, K. A.; Kelly, M. A.; Gao, J. *Nat. Commun.,* 2015, 6, 6561.

Cal, P. M.; Frade, R. F.; Cordeiro, C.; Gois, P. M. *Chemistry* 2015, 21, 8182

Akcay, G.; Belmonte, M. A.; Aquila, B.; Chuaqui, C.; Hird, A. W.; Lamb, M. L.; Rawlins, P. B.; Su, N.; Tentarelli, S.; Grimster, N. P.; Su, Q. *Nat. Chem. Biol.,* 2016, 12, 931.

Jafari, M. R.; Deng, L.; Kitov, P. I.; Ng, S.; Matochko, W. L.; Tjhung, K. F.; Zeberoff, A.; Elias, A.; Klassen, J. S.; Derda, R. *ACS Chem. Biol.,* 2014, 9, 443.

Bandyopadhyay, A.; Cambray, S.; Gao, J. *J. Am. Chem. Soc.,* 2017, 139, 871.

Gasanov, U.; Koina, C.; Beagley, K. W.; Aitken, R. J.; Hansbro, P. M. *Infect. Immun.,* 2006, 74, 566.

Andra, J.; Goldmann, T.; Ernst, C. M.; Peschel, A.; Gutsmann, T. *J. Biol. Chem.,* 2011, 286, 18692.

Slavetinsky, C.; Kuhn, S.; Peschel, A. *Biochim. Biophys. Acta-Mol. Cell Biol. Lipids,* 2017, 1862, 1310.

Bandyopadhyay, A.; Gao, J. *J. Am. Chem. Soc.,* 2016, 138, 2098.

Peschel, A.; Jack, R. W.; Otto, M.; Collins, L. V.; Staubitz, P.; Nicholson, G.; Kalbacher, H.; Nieuwenhuizen, W. F.; Jung, G.; Tarkowski, A.; van Kessel, K. P.; van Strijp, J. A. *J. Exp. Med.,* 2001, 193, 1067.

Dosselli, R.; Gobbo, M.; Bolognini, E.; Campestrini, S.; Reddi, E. *ACS Med. Chem. Lett.,* 2010, 1, 35.

Liu, F.; Soh Yan Ni, A.; Lim, Y.; Mohanram, H.; Bhattacharjya, S.; Xing, B. *Bioconjug. Chem.,* 2012, 23, 1639.

Kasimova, K. R.; Sadasivam, M.; Landi, G.; Sarna, T.; Hamblin, M. R. *Photochem. Photobiol. Sci.,* 2014, 13, 1541.

Johnson, G. A.; Muthukrishnan, N.; Pellois, J. P. *Bioconjug. Chem.,* 2013, 24, 114.

Alves, E.; Costa, L.; Carvalho, C. M.; Tome, J. P.; Faustino, M. A.; Neves, M. G.; Tome, A. C.; Cavaleiro, J. A.; Cunha, A.; Almeida, A. *BMC Microbiol.,* 2009, 9, 70.

Sperandio, F. F.; Huang, Y. Y.; Hamblin, M. R. *Recent Pat. Antiinfect. Drug Discov.,* 2013, 8, 108.

Peleg, A. Y.; Seifert, H.; Paterson, D. L. *Clin. Microbiol. Rev.,* 2008, 21, 538.

Arroyo, L. A.; Herrera, C. M.; Fernandez, L.; Hankins, J. V.; Trent, M. S.; Hancock, R. E. *Antimicrob. Agents Chemother.,* 2011, 55, 3743.

Boll, J. M.; Crofts, A. A.; Peters, K.; Cattoir, V.; Vollmer, W.; Davies, B. W.; Trent, M. S. *Proc. Natl. Acad. Sci.,* 2016, 113, E6228.

Powers, M. J.; Trent, M. S. *Mol. Microbiol.,* 2018, 107, 47.

Jacobs, A. C.; Thompson, M. G.; Black, C. C.; Kessler, J. L.; Clark, L. P.; McQueary, C. N.; Gancz, H. Y.; Corey, B. W.; Moon, J. K.; Si, Y.; Owen, M. T.; Hallock, J. D.; Kwak, Y. I.; Summers, A.; Li, C. Z.; Rasko, D. A.; Penwell, W. F.; Honnold, C. L.; Wise, M. C.; Waterman, P. E.; Lesho, E. P.; Stewart, R. L.; Actis, L. A.; Palys, T. J.; Craft, D. W.; Zurawski, D. V. *MBio* 2014, 5, e01076.

Kristian, S. A.; Datta, V.; Weidenmaier, C.; Kansal, R.; Fedtke, I.; Peschel, A.; Gallo, R. L.; Nizet, V. *J. Bacterial.,* 2005, 187, 6719.

Brown, S.; Santa Maria, J. P., Jr.; Walker, S. *Annu. Rev. Microbial.,* 2013, 67, 313.

Needham, B. D.; Trent, M. S. *Nature Rev. Microbial.,* 2013, 11, 467.

The preceding Examples are offered for illustrative purposes only, and are not intended to limit the scope of the present invention in any way. Various modifications of the invention in addition to those shown and described herein will become apparent to those skilled in the art from the foregoing description and fall within the scope of the appended claims.

What is claimed is:

1. A phage display library comprising phage particles comprising phage displayed peptides comprising two acetylphenylboronic acid (APBA) modified cysteine residues.

2. The phage display library of claim 1, wherein the phage displayed peptides comprise a peptide sequence given by:

$XC^*(X)_nC^*(X)_m$, wherein C* indicates an APBA modified cystein residue; wherein each instance of X is an amino acid independently selected from D, E, K, R, H, Y, N, Q, S, T, G, A, V, L, I, M, P, F, and W; wherein n is an integer selected from 5, 6, 7, 8, 9, and 10; wherein m is an integer selected from 1, 2, 3, 4, and 5.

3. The phage display library of claim 2, wherein the phage display peptides comprise a peptide sequence given by:

$AC^*(X)_nC^*(G)_m$.

4. The phage display library of claim 2, wherein n is 6, 7, or 8; and wherein m is 2, 3, or 4.

5. The phage display library of claim 1, wherein the APBA modified cysteine residue has a structure given by a formula:

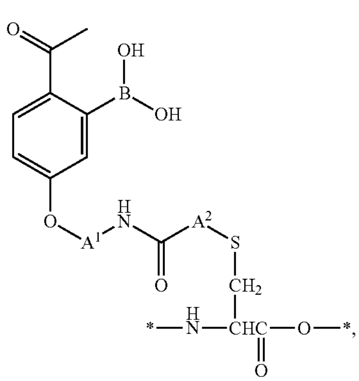

wherein each of $A^1$ and $A^2$ are independently a C1-C6 alkyl.

6. The phage display library of claim 5, wherein the APBA modified cysteine residue has a structure given by a formula:

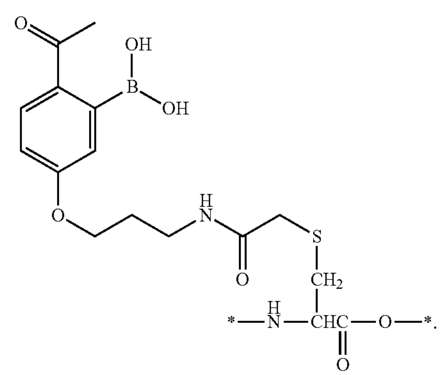

7. An acetylphenylboronic acid (APBA) peptide comprising a peptide sequence given by:

$XC^*(X)_nC^*(X)_m$, wherein C* indicates an APBA modified cystein residue; wherein each instance of X is an amino acid independently selected from D, E, K, R, H, Y, N, Q, S, T, G, A, V, L, I, M, P, F, and W; wherein n is an integer selected from 5, 6, 7, 8, 9, and 10; wherein m is an integer selected from 1, 2, 3, 4, and 5.

8. The APBA peptide of claim 7, wherein the phage display peptides comprise a peptide sequence given by:

$AC^*(X)_nC^*(G)_m$.

9. The APBA peptide of claim 7, wherein n is 6, 7, or 8; and wherein m is 2, 3, or 4.

10. The APBA peptide of claim 7, wherein the APBA modified cysteine residue has a structure given by a formula:

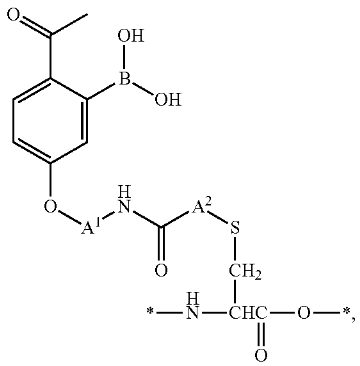

wherein each of $A^1$ and $A^2$ are independently a C1-C6 alkyl.

11. The APBA peptide of claim 10, wherein the APBA modified cysteine residue has a structure given by a formula:

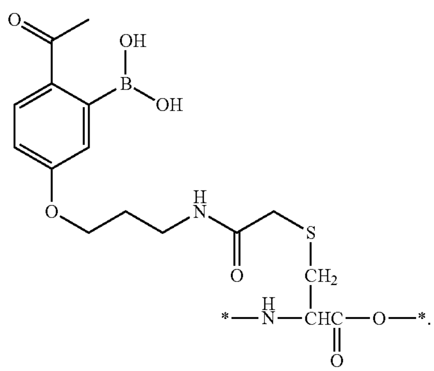

12. The APBA peptide of claim 7, further comprising an antibiotic residue, a phototoxin residue, or a detectable label residue at the N-terminus of the peptide.

13. The APBA peptide of claim 7, further comprising an antibiotic residue, a phototoxin residue, or a detectable label residue at the C-terminus of the peptide.

14. A pharmaceutical composition comprising the APBA peptide of claim 7 and a pharmaceutically excipient.

15. The pharmaceutical composition of claim 14, further comprising a therapeutic agent.

16. A drug screening method for selection of an APBA peptide, comprising contacting the phage display library of claim 1 to a target cell, and selecting a phage clone displaying a peptide capable of binding to the target cell.

17. The drug screening method of claim 16, wherein the target cell is a bacterial cell.

18. The drug screening method of claim 17, wherein the bacterial cell is a *Staphylococcus aureus* or *Acinetobacter baumannii* cell.

19. A method of developing a novel narrow-spectrum antibiotics for a bacterial strain of interest, comprising:

a) Screening the phage display library according to claim 1 with live bacteria of the bacterial strain of interest;

b) Selecting peptide binders with submicromolar affinity against the bacterial strain of interest;

c) Conjugating the selected peptide binders with an agent; and d) Converting the peptide binders agent conjugate to an antibiotics targeting the bacterial strain of interest.

20. The method of claim 19, wherein the bacterial strain is a *Staphylococcus aureus* or *Acinetobacter baumannii* strain.

* * * * *

SEQUENCE LISTING

```
<160> NUMBER OF SEQ ID NOS: 282

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1

gcttgtacga ctgctgcgtc gcgtttgtgc                                      30


<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2

gcttgtcctg atggtttgag tccgcgttgc                                      30


<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3

gcttgtccga cgagtaataa tcgggagtgc                                      30


<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4

gcttgtaatt ttactaagac gtttcgttgc                                      30


<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5

gcttgtaagg tgagtaagat ggagcgttgc                                      30


<210> SEQ ID NO 6
```

-continued

```
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6

gcttgtaagt ttgattcgac gaggtattgc                                       30


<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7

gcttgtcttg agctttttca ttcgtcgtgc                                       30


<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8

gcttgtacga atcctgtgac tgctcggtgc                                       30


<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9

gcttgtacga atacgctgcc taagctgtgc                                       30


<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10

gcttgtcaga gggagatgac gcatatgtgc                                       30


<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11

gcttgtatga atccgcgggg taatttgtgc                                       30


<210> SEQ ID NO 12
<211> LENGTH: 30
```

<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 12
gcttgttatg gttctatgtc gagtatgtgc 30

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 13
gcttgtcaga gggagatgac gcatatgtgc 30

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 14
gcttgtacga ctgctgcgtc gcgtttgtgc 30

<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 15
gcttgtgcta gggttcattc gttgggttgc 30

<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 16
gcttgtaatc cgacttcgct taattcgtgc 30

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 17
gcttgtagta cgaatagtaa tattgtgtgc 30

<210> SEQ ID NO 18
<211> LENGTH: 30
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 18

gcttgtaata ctcagtcgaa gcatgagtgc                                        30


<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ala Cys Thr Thr Ala Ala Ser Arg Leu Cys
1               5                   10


<210> SEQ ID NO 20
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ala Cys Pro Asp Gly Leu Ser Pro Arg Cys
1               5                   10


<210> SEQ ID NO 21
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ala Cys Pro Thr Ser Asn Asn Arg Glu Cys
1               5                   10


<210> SEQ ID NO 22
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ala Cys Asn Phe Thr Lys Thr Phe Arg Cys
1               5                   10


<210> SEQ ID NO 23
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ala Cys Lys Val Ser Lys Met Glu Arg Cys
1               5                   10
```

<210> SEQ ID NO 24
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

```
Ala Cys Lys Phe Asp Ser Thr Arg Tyr Cys
1               5                   10
```

<210> SEQ ID NO 25
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

```
Ala Cys Leu Glu Leu Phe His Ser Ser Cys
1               5                   10
```

<210> SEQ ID NO 26
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

```
Ala Cys Thr Asn Pro Val Thr Ala Arg Cys
1               5                   10
```

<210> SEQ ID NO 27
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

```
Ala Cys Thr Asn Thr Leu Pro Lys Leu Cys
1               5                   10
```

<210> SEQ ID NO 28
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

```
Ala Cys Gln Arg Glu Met Thr His Met Cys
1               5                   10
```

<210> SEQ ID NO 29
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ala Cys Met Asn Pro Arg Gly Asn Leu Cys
1 5 10

<210> SEQ ID NO 30
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 30

Ala Cys Tyr Gly Ser Met Ser Ser Met Cys
1 5 10

<210> SEQ ID NO 31
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 31

Ala Cys Gln Arg Glu Met Thr His Met Cys
1 5 10

<210> SEQ ID NO 32
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 32

Ala Cys Thr Thr Ala Ala Ser Arg Leu Cys
1 5 10

<210> SEQ ID NO 33
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 33

Ala Cys Ala Arg Val His Ser Leu Gly Cys
1 5 10

<210> SEQ ID NO 34
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 34

Ala Cys Asn Pro Thr Ser Leu Asn Ser Cys
1 5 10

<210> SEQ ID NO 35
<211> LENGTH: 10
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 35

Ala Cys Ser Thr Asn Ser Asn Ile Val Cys
1 5 10

<210> SEQ ID NO 36
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 36

Ala Cys Asn Thr Gln Ser Lys His Glu Cys
1 5 10

<210> SEQ ID NO 37
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 37
gcttgtacga ctgctgcgtc gcgtttgtgc 30

<210> SEQ ID NO 38
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 38
gcttgtaagg tgagtaagat ggagcgttgc 30

<210> SEQ ID NO 39
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 39
gcttgtacga ctgctgcgtc gcgtttgtgc 30

<210> SEQ ID NO 40
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 40
gcttgtagtg agggtagggc ttatgcttgc 30

<210> SEQ ID NO 41
<211> LENGTH: 30

-continued

<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 41
gcttgtcatt ggtattctag taaggcttgc 30

<210> SEQ ID NO 42
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 42
gcttgtcatt ggtattctag taaggcttgc 30

<210> SEQ ID NO 43
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 43
gcttgtgttt ctccgaggag tcatgagtgc 30

<210> SEQ ID NO 44
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 44
gcttgtcaga gggagatgac gcatatgtgc 30

<210> SEQ ID NO 45
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 45
gcttgtacga ctgctgcgtc gcgtttgtgc 30

<210> SEQ ID NO 46
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 46
gcttgtacga ctgctgcgtc gcgtttgtgc 30

<210> SEQ ID NO 47
<211> LENGTH: 30
<212> TYPE: DNA

-continued

<213> ORGANISM: Artificial Sequence
<220> FEATURE:
<223> OTHER INFORMATION: Description of Artificial Sequence: Synthetic
      oligonucleotide

<400> SEQUENCE: 47
gcttgtacga ctgctgcgtc gcgtttgtgc 30

<210> SEQ ID NO 48
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
gcttgttatg gttctatgtc gagtatgtgc 30

<210> SEQ ID NO 49
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
gcttgtgttt ctccgaggag tcatgagtgc 30

<210> SEQ ID NO 50
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
gcttgtgttt ctccgaggag tcatgagtgc 30

<210> SEQ ID NO 51
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
gcttgtgttt ctccgaggag tcatgagtgc 30

<210> SEQ ID NO 52
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
gcttgtagtg agggtagggc ttatgcttgc 30

<210> SEQ ID NO 53
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 53
gcttgtaagt attctcattc tagttcttgc 30

<210> SEQ ID NO 54
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 54
gcttgtcatt ggtattctag taaggcttgc 30

<210> SEQ ID NO 55
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 55
gcttgtacga agttgatgca tggttggtgc 30

<210> SEQ ID NO 56
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 56
gcttgtagtg agggtagggc ttatgcttgc 30

<210> SEQ ID NO 57
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 57

Ala Cys Thr Thr Ala Ala Ser Arg Leu Cys
1 5 10

<210> SEQ ID NO 58
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 58

Ala Cys Lys Val Ser Lys Met Glu Arg Cys
1 5 10

<210> SEQ ID NO 59
<211> LENGTH: 10
<212> TYPE: PRT

-continued

<213> ORGANISM: Artificial Sequence
<220> FEATURE:
<223> OTHER INFORMATION: Description of Artificial Sequence: Synthetic
      peptide

<400> SEQUENCE: 59

Ala Cys Thr Thr Ala Ala Ser Arg Leu Cys
1               5                   10

<210> SEQ ID NO 60
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Ala Cys Ser Glu Gly Arg Ala Tyr Ala Cys
1               5                   10

<210> SEQ ID NO 61
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Ala Cys His Trp Tyr Ser Ser Lys Ala Cys
1               5                   10

<210> SEQ ID NO 62
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Ala Cys His Trp Tyr Ser Ser Lys Ala Cys
1               5                   10

<210> SEQ ID NO 63
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Ala Cys Val Ser Pro Arg Ser His Glu Cys
1               5                   10

<210> SEQ ID NO 64
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Ala Cys Gln Arg Glu Met Thr His Met Cys
1               5                   10

<210> SEQ ID NO 65
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 65

Ala Cys Thr Thr Ala Ala Ser Arg Leu Cys
1 5 10

<210> SEQ ID NO 66
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 66

Ala Cys Thr Thr Ala Ala Ser Arg Leu Cys
1 5 10

<210> SEQ ID NO 67
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 67

Ala Cys Thr Thr Ala Ala Ser Arg Leu Cys
1 5 10

<210> SEQ ID NO 68
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 68

Ala Cys Tyr Gly Ser Met Ser Ser Met Cys
1 5 10

<210> SEQ ID NO 69
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 69

Ala Cys Val Ser Pro Arg Ser His Glu Cys
1 5 10

<210> SEQ ID NO 70
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 70

Ala Cys Val Ser Pro Arg Ser His Glu Cys
1 5 10

<210> SEQ ID NO 71
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 71

Ala Cys Val Ser Pro Arg Ser His Glu Cys
1 5 10

<210> SEQ ID NO 72
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 72

Ala Cys Ser Glu Gly Arg Ala Tyr Ala Cys
1 5 10

<210> SEQ ID NO 73
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 73

Ala Cys Lys Tyr Ser His Ser Ser Ser Cys
1 5 10

<210> SEQ ID NO 74
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 74

Ala Cys His Trp Tyr Ser Ser Lys Ala Cys
1 5 10

<210> SEQ ID NO 75
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 75

Ala Cys Thr Lys Leu Met His Gly Trp Cys
1 5 10

<210> SEQ ID NO 76
<211> LENGTH: 10

<212> TYPE: PRT
<213> ORGANISM: Artificial Sequence
<220> FEATURE:
<223> OTHER INFORMATION: Description of Artificial Sequence: Synthetic peptide

<400> SEQUENCE: 76

Ala Cys Ser Glu Gly Arg Ala Tyr Ala Cys
1 5 10

<210> SEQ ID NO 77
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 77

Ala Cys Thr Thr Ala Ala Ser Arg Leu Cys
1 5 10

<210> SEQ ID NO 78
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 78

Ala Cys Lys Val Ser Lys Met Glu Arg Cys
1 5 10

<210> SEQ ID NO 79
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 79

Ala Cys Gln Arg Glu Met Thr His Met Cys
1 5 10

<210> SEQ ID NO 80
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 80

Ala Cys Tyr Gly Ser Met Ser Ser Met Cys
1 5 10

<210> SEQ ID NO 81
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 81

Ala Cys Ser Glu Gly Arg Ala Tyr Ala Cys

-continued

```
1               5                   10


<210> SEQ ID NO 82
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Ala Cys His Trp Tyr Ser Ser Lys Ala Cys
1               5                   10


<210> SEQ ID NO 83
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Ala Cys Val Ser Pro Arg Ser His Glu Cys
1               5                   10


<210> SEQ ID NO 84
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Diaminopropionic acid

<400> SEQUENCE: 84

Ala Cys Thr Thr Ala Ala Ser Arg Leu Cys Gly Gly Gly Xaa
1               5                   10


<210> SEQ ID NO 85
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Diaminopropionic acid

<400> SEQUENCE: 85

Ala Cys Lys Val Ser Lys Met Glu Arg Cys Gly Gly Gly Xaa
1               5                   10


<210> SEQ ID NO 86
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Diaminopropionic acid
```

<400> SEQUENCE: 86

Ala Cys Gln Arg Glu Met Thr His Met Cys Gly Gly Gly Xaa
1 5 10

<210> SEQ ID NO 87
<211> LENGTH: 14
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (14)..(14)
<223> OTHER INFORMATION: Diaminopropionic acid

<400> SEQUENCE: 87

Ala Cys His Trp Tyr Ser Ser Lys Ala Cys Gly Gly Gly Xaa
1 5 10

<210> SEQ ID NO 88
<211> LENGTH: 14
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (14)..(14)
<223> OTHER INFORMATION: Diaminopropionic acid

<400> SEQUENCE: 88

Ala Cys Val Ser Pro Arg Ser His Glu Cys Gly Gly Gly Xaa
1 5 10

<210> SEQ ID NO 89
<211> LENGTH: 14
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (14)..(14)
<223> OTHER INFORMATION: Diaminopropionic acid

<400> SEQUENCE: 89

Ala Cys Thr Thr Ala Ala Ser Arg Leu Cys Gly Gly Gly Xaa
1 5 10

<210> SEQ ID NO 90
<211> LENGTH: 14
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (14)..(14)
<223> OTHER INFORMATION: Diaminopropionic acid

<400> SEQUENCE: 90

Ala Cys Lys Val Ser Lys Met Glu Arg Cys Gly Gly Gly Xaa
1 5 10

<210> SEQ ID NO 91

```
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Diaminopropionic acid

<400> SEQUENCE: 91

Ala Cys Gln Arg Glu Met Thr His Met Cys Gly Gly Gly Xaa
1               5                   10


<210> SEQ ID NO 92
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Diaminopropionic acid

<400> SEQUENCE: 92

Ala Cys His Trp Tyr Ser Ser Lys Ala Cys Gly Gly Gly Xaa
1               5                   10


<210> SEQ ID NO 93
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Diaminopropionic acid

<400> SEQUENCE: 93

Ala Cys Val Ser Pro Arg Ser His Glu Cys Gly Gly Gly Xaa
1               5                   10


<210> SEQ ID NO 94
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Diaminopropionic acid

<400> SEQUENCE: 94

Ala Cys Val Ser Pro Arg Ser His Glu Cys Gly Gly Gly Xaa
1               5                   10


<210> SEQ ID NO 95
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

<221> NAME/KEY: MOD_RES
<222> LOCATION: (14)..(14)
<223> OTHER INFORMATION: Diaminopropionic acid

<400> SEQUENCE: 95

Ala Cys Val Ser Pro Arg Ser His Glu Cys Gly Gly Gly Xaa
1 5 10

<210> SEQ ID NO 96
<211> LENGTH: 14
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (14)..(14)
<223> OTHER INFORMATION: Diaminopropionic acid

<400> SEQUENCE: 96

Ala Cys Val Ser Pro Arg Ser His Glu Cys Gly Gly Gly Xaa
1 5 10

<210> SEQ ID NO 97
<211> LENGTH: 14
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (14)..(14)
<223> OTHER INFORMATION: Diaminopropionic acid

<400> SEQUENCE: 97

Ala Cys Gly Pro Thr Ala Lys Tyr Ile Cys Gly Gly Gly Xaa
1 5 10

<210> SEQ ID NO 98
<211> LENGTH: 14
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (14)..(14)
<223> OTHER INFORMATION: Diaminopropionic acid

<400> SEQUENCE: 98

Ala Cys Thr Thr Ala Ala Ser Arg Leu Cys Gly Gly Gly Xaa
1 5 10

<210> SEQ ID NO 99
<211> LENGTH: 14
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (14)..(14)
<223> OTHER INFORMATION: Diaminopropionic acid

<400> SEQUENCE: 99

Ala Cys Lys Val Ser Lys Met Glu Arg Cys Gly Gly Gly Xaa 1 5 10

<210> SEQ ID NO 100
<211> LENGTH: 14
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (14)..(14)
<223> OTHER INFORMATION: Diaminopropionic acid

<400> SEQUENCE: 100

Ala Cys Gln Arg Glu Met Thr His Met Cys Gly Gly Gly Xaa
1 5 10

<210> SEQ ID NO 101
<211> LENGTH: 14
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (14)..(14)
<223> OTHER INFORMATION: Diaminopropionic acid

<400> SEQUENCE: 101

Ala Cys His Trp Tyr Ser Ser Lys Ala Cys Gly Gly Gly Xaa
1 5 10

<210> SEQ ID NO 102
<211> LENGTH: 14
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (14)..(14)
<223> OTHER INFORMATION: Diaminopropionic acid

<400> SEQUENCE: 102

Ala Cys Val Ser Pro Arg Ser His Glu Cys Gly Gly Gly Xaa
1 5 10

<210> SEQ ID NO 103
<211> LENGTH: 14
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (14)..(14)
<223> OTHER INFORMATION: Diaminopropionic acid

<400> SEQUENCE: 103

Ala Cys Val Ser Pro Arg Ser His Glu Cys Gly Gly Gly Xaa
1 5 10

<210> SEQ ID NO 104
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Diaminopropionic acid

<400> SEQUENCE: 104

Ala Cys Val Ser Pro Arg Ser His Glu Cys Gly Gly Gly Xaa
1               5                   10

<210> SEQ ID NO 105
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Diaminopropionic acid

<400> SEQUENCE: 105

Ala Cys Val Ser Pro Arg Ser His Glu Cys Gly Gly Gly Xaa
1               5                   10

<210> SEQ ID NO 106
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Diaminopropionic acid

<400> SEQUENCE: 106

Ala Cys Gly Pro Thr Ala Lys Tyr Ile Cys Gly Gly Gly Xaa
1               5                   10

<210> SEQ ID NO 107
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
gcttgttcta ctttggcgca gcgtgcgtgc                                        30

<210> SEQ ID NO 108
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
gcttgtccga agtcgagtat tgatccgtgc                                        30

<210> SEQ ID NO 109
<211> LENGTH: 30
<212> TYPE: DNA

<213> ORGANISM: Artificial Sequence
<220> FEATURE:
<223> OTHER INFORMATION: Description of Artificial Sequence: Synthetic
oligonucleotide

<400> SEQUENCE: 109
gcttgtacta aggatagtcc ggggctttgc 30

<210> SEQ ID NO 110
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 110
gcttgtctga atgctgttac ggagaagtgc 30

<210> SEQ ID NO 111
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 111
gcttgtgggc ttaatgtttc gactcattgc 30

<210> SEQ ID NO 112
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 112
gcttgttggt tgagtgcggc ggcgcagtgc 30

<210> SEQ ID NO 113
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 113

Ala Cys Ser Thr Leu Ala Gln Arg Ala Cys
1 5 10

<210> SEQ ID NO 114
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 114

Ala Cys Pro Lys Ser Ser Ile Asp Pro Cys
1 5 10

<210> SEQ ID NO 115
<211> LENGTH: 10

-continued

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 115

Ala Cys Thr Lys Asp Ser Pro Gly Leu Cys
1 5 10

<210> SEQ ID NO 116
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 116

Ala Cys Leu Asn Ala Val Thr Glu Lys Cys
1 5 10

<210> SEQ ID NO 117
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 117

Ala Cys Gly Leu Asn Val Ser Thr His Cys
1 5 10

<210> SEQ ID NO 118
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 118

Ala Cys Trp Leu Ser Ala Ala Ala Gln Cys
1 5 10

<210> SEQ ID NO 119
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 119
gcttgttctg cgtatgatag gcctctttgc 30

<210> SEQ ID NO 120
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 120
gcttgtgcta agatttttac tggttgttgc 30

<210> SEQ ID NO 121
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 121
gcttgttcgc cttggaatcc ttcgcattgc 30

<210> SEQ ID NO 122
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 122
gcttgtacgg gtgcttctaa taatacttgc 30

<210> SEQ ID NO 123
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 123
gcttgttcgc cttggaatcc ttcgcattgc 30

<210> SEQ ID NO 124
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 124
gcttgtgcta agatttttac tggttgttgc 30

<210> SEQ ID NO 125
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 125
gcttgtacgt ctggtcctgc tcttacgtgc 30

<210> SEQ ID NO 126
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 126
gcttgtgcta agatttttac tggttgttgc 30

<210> SEQ ID NO 127
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 127
gcttgtcggc cgactaatgg gtttgcgtgc 30

<210> SEQ ID NO 128
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 128
gcttgtcagt tggttcctgg ggcttattgc 30

<210> SEQ ID NO 129
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 129
gcttgtactc atctgcataa gcgtacgtgc 30

<210> SEQ ID NO 130
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 130
gcttgttcga cgttgtcgca gcctgcgtgc 30

<210> SEQ ID NO 131
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 131
gcttgttcgc cttggaatcc ttcgcattgc 30

<210> SEQ ID NO 132
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 132

Ala Cys Ser Ala Tyr Asp Arg Pro Leu Cys
1 5 10

```
<210> SEQ ID NO 133
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Ala Cys Ala Lys Ile Phe Thr Gly Cys Cys
1               5                   10


<210> SEQ ID NO 134
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Ala Cys Ser Pro Trp Asn Pro Ser His Cys
1               5                   10


<210> SEQ ID NO 135
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Ala Cys Thr Gly Ala Ser Asn Asn Thr Cys
1               5                   10


<210> SEQ ID NO 136
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Ala Cys Ser Pro Trp Asn Pro Ser His Cys
1               5                   10


<210> SEQ ID NO 137
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Ala Cys Ala Lys Ile Phe Thr Gly Cys Cys
1               5                   10


<210> SEQ ID NO 138
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138
```

```
Ala Cys Thr Ser Gly Pro Ala Leu Thr Cys
1               5                   10


<210> SEQ ID NO 139
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Ala Cys Ala Lys Ile Phe Thr Gly Cys Cys
1               5                   10


<210> SEQ ID NO 140
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Ala Cys Arg Pro Thr Asn Gly Phe Ala Cys
1               5                   10


<210> SEQ ID NO 141
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Ala Cys Gln Leu Val Pro Gly Ala Tyr Cys
1               5                   10


<210> SEQ ID NO 142
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Ala Cys Thr His Leu His Lys Arg Thr Cys
1               5                   10


<210> SEQ ID NO 143
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Ala Cys Ser Thr Leu Ser Gln Pro Ala Cys
1               5                   10


<210> SEQ ID NO 144
<211> LENGTH: 10
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 144

Ala Cys Ser Pro Trp Asn Pro Ser His Cys
1               5                   10


<210> SEQ ID NO 145
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Ala Cys Ala Lys Ile Phe Thr Gly Cys Cys
1               5                   10


<210> SEQ ID NO 146
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Ala Cys Ser Pro Trp Asn Pro Ser His Cys
1               5                   10


<210> SEQ ID NO 147
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147

gcttgtaagc agacttatcc gcagagttgc                                        30


<210> SEQ ID NO 148
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 148

gcttgtgcta ctcatgggtt ggataggtgc                                        30


<210> SEQ ID NO 149
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149

gcttgtgaga aggaggatag taggaggtgc                                        30


<210> SEQ ID NO 150
<211> LENGTH: 30
```

<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 150
gcttgtttga ctcttctgat ggaggcgtgc 30

<210> SEQ ID NO 151
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 151
gcttgtactc cgcattcgct gcatgcgtgc 30

<210> SEQ ID NO 152
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 152
gcttgtaaga cttctgagaa gacgagttgc 30

<210> SEQ ID NO 153
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 153

Ala Cys Lys Gln Thr Tyr Pro Gln Ser Cys
1 5 10

<210> SEQ ID NO 154
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 154

Ala Cys Ala Thr His Gly Leu Asp Arg Cys
1 5 10

<210> SEQ ID NO 155
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 155

Ala Cys Glu Lys Glu Asp Ser Arg Arg Cys
1 5 10

<210> SEQ ID NO 156
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 156

Ala Cys Leu Thr Leu Leu Met Glu Ala Cys
1 5 10

<210> SEQ ID NO 157
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 157

Ala Cys Thr Pro His Ser Leu His Ala Cys
1 5 10

<210> SEQ ID NO 158
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 158

Ala Cys Lys Thr Ser Glu Lys Thr Ser Cys
1 5 10

<210> SEQ ID NO 159
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 159
gcttgtactt ctccggttaa gactctttgc 30

<210> SEQ ID NO 160
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 160
gcttgtcatc ggcctcatga ggcgatgtgc 30

<210> SEQ ID NO 161
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 161
gcttgtcatg gtccgagggc gtctcagtgc 30

<210> SEQ ID NO 162
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 162
gcttgtttta agcattctaa gtttgcgtgc 30

<210> SEQ ID NO 163
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 163
gcttgtaatc agctgatgaa tttgacttgc 30

<210> SEQ ID NO 164
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 164
gcttgtcatc ggcctcatga ggcgatgtgc 30

<210> SEQ ID NO 165
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 165
gcttgtgatc ataggacgcg gccgtggtgc 30

<210> SEQ ID NO 166
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 166
gcttgtcatc ggcctcatga ggcgatgtgc 30

<210> SEQ ID NO 167
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 167
gcttgtccga cggagctgca ttttcattgc 30

<210> SEQ ID NO 168
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 168
gcttgtcatc ggcctcatga ggcgatgtgc 30

<210> SEQ ID NO 169
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 169
gcttgtacta agatgacgct tcattgc 27

<210> SEQ ID NO 170
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 170
gcttgtcagc atggtacgac tcatggttgc 30

<210> SEQ ID NO 171
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 171
gcttgtattc gtgatcagaa tatgcggtgc 30

<210> SEQ ID NO 172
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 172

Ala Cys Thr Ser Pro Val Lys Thr Leu Cys
1 5 10

<210> SEQ ID NO 173
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 173

Ala Cys His Arg Pro His Glu Ala Met Cys
1 5 10

<210> SEQ ID NO 174
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 174

Ala Cys His Gly Pro Arg Ala Ser Gln Cys
1 5 10

<210> SEQ ID NO 175
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 175

Ala Cys Phe Lys His Ser Lys Phe Ala Cys
1 5 10

<210> SEQ ID NO 176
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 176

Ala Cys Asn Gln Leu Met Asn Leu Thr Cys
1 5 10

<210> SEQ ID NO 177
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 177

Ala Cys His Arg Pro His Glu Ala Met Cys
1 5 10

<210> SEQ ID NO 178
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 178

Ala Cys Asp His Arg Thr Arg Pro Trp Cys
1 5 10

<210> SEQ ID NO 179
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 179

Ala Cys His Arg Pro His Glu Ala Met Cys
1 5 10

<210> SEQ ID NO 180
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 180

Ala Cys Pro Thr Glu Leu His Phe His Cys
1 5 10

<210> SEQ ID NO 181
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 181

Ala Cys His Arg Pro His Glu Ala Met Cys
1 5 10

<210> SEQ ID NO 182
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 182

Ala Cys Thr Lys Met Thr Leu His Cys
1 5

<210> SEQ ID NO 183
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 183

Ala Cys Gln His Gly Thr Thr His Gly Cys
1 5 10

<210> SEQ ID NO 184
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 184

Ala Cys Ile Arg Asp Gln Asn Met Arg Cys
1 5 10

<210> SEQ ID NO 185
<211> LENGTH: 10

<212> TYPE: PRT
<213> ORGANISM: Artificial Sequence
<220> FEATURE:
<223> OTHER INFORMATION: Description of Artificial Sequence: Synthetic peptide

<400> SEQUENCE: 185

Ala Cys His Arg Pro His Glu Ala Met Cys
1 5 10

<210> SEQ ID NO 186
<211> LENGTH: 14
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (14)..(14)
<223> OTHER INFORMATION: Diaminopropionic acid

<400> SEQUENCE: 186

Ala Cys Ala Lys Ile Phe Thr Gly Cys Cys Gly Gly Gly Xaa
1 5 10

<210> SEQ ID NO 187
<211> LENGTH: 14
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (14)..(14)
<223> OTHER INFORMATION: Diaminopropionic acid

<400> SEQUENCE: 187

Ala Cys Ser Pro Trp Asn Pro Ser His Cys Gly Gly Gly Xaa
1 5 10

<210> SEQ ID NO 188
<211> LENGTH: 14
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (14)..(14)
<223> OTHER INFORMATION: Diaminopropionic acid

<400> SEQUENCE: 188

Ala Cys His Arg Pro His Glu Ala Met Cys Gly Gly Gly Xaa
1 5 10

<210> SEQ ID NO 189
<211> LENGTH: 14
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (14)..(14)
<223> OTHER INFORMATION: Diaminopropionic acid

<400> SEQUENCE: 189

Ala Cys Thr Ser Pro Val Lys Thr Leu Cys Gly Gly Gly Xaa
1 5 10

<210> SEQ ID NO 190
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 190
gcttgtattc cgactcatgc taattcgtgc 30

<210> SEQ ID NO 191
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 191
gcttgtacgt tgccgaatgg gcctaggtgc 30

<210> SEQ ID NO 192
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 192
gcttgtgagc cggggctggc gaggttttgc 30

<210> SEQ ID NO 193
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 193
gcttgtacgt tgccgaatgg gcctaggtgc 30

<210> SEQ ID NO 194
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 194
gcttgtacgt tgccgaatgg gcctaggtgc 30

<210> SEQ ID NO 195
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 195
gcttgtattc cgactcatgc taattcgtgc 30

<210> SEQ ID NO 196
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 196
gcttgtaagc tgtcgggtca tgcgccttgc 30

<210> SEQ ID NO 197
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 197
gcttgtaagc atttgccggc gccgaattgc 30

<210> SEQ ID NO 198
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 198
gcttgtaagc tgtcgggtca tgcgccttgc 30

<210> SEQ ID NO 199
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 199
gcttgtacgt tgccgaatgg gcctaggtgc 30

<210> SEQ ID NO 200
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 200
gcttgtacgt tgccgaatgg gcctaggtgc 30

<210> SEQ ID NO 201
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 201
gcttgtaata tgcatacgcc tatggtgtgc 30

<210> SEQ ID NO 202
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 202
gcttgtacgt tgccgaatgg gcctaggtgc 30

<210> SEQ ID NO 203
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 203
gcttgtttgg agcagagggg gccggattgc 30

<210> SEQ ID NO 204
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 204

Ala Cys Ile Pro Thr His Ala Asn Ser Cys
1 5 10

<210> SEQ ID NO 205
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 205

Ala Cys Thr Leu Pro Asn Gly Pro Arg Cys
1 5 10

<210> SEQ ID NO 206
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 206

Ala Cys Glu Pro Gly Leu Ala Arg Phe Cys
1 5 10

<210> SEQ ID NO 207
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 207

Ala Cys Thr Leu Pro Asn Gly Pro Arg Cys
1 5 10

<210> SEQ ID NO 208
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 208

Ala Cys Thr Leu Pro Asn Gly Pro Arg Cys
1 5 10

<210> SEQ ID NO 209
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 209

Ala Cys Ile Pro Thr His Ala Asn Ser Cys
1 5 10

<210> SEQ ID NO 210
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 210

Ala Cys Lys Leu Ser Gly His Ala Pro Cys
1 5 10

<210> SEQ ID NO 211
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 211

Ala Cys Lys His Leu Pro Ala Pro Asn Cys
1 5 10

<210> SEQ ID NO 212
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 212

Ala Cys Lys Leu Ser Gly His Ala Pro Cys
1 5 10

<210> SEQ ID NO 213
<211> LENGTH: 10
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 213

Ala Cys Thr Leu Pro Asn Gly Pro Arg Cys
1               5                   10


<210> SEQ ID NO 214
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Ala Cys Thr Leu Pro Asn Gly Pro Arg Cys
1               5                   10


<210> SEQ ID NO 215
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Ala Cys Asn Met His Thr Pro Met Val Cys
1               5                   10


<210> SEQ ID NO 216
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Ala Cys Thr Leu Pro Asn Gly Pro Arg Cys
1               5                   10


<210> SEQ ID NO 217
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Ala Cys Leu Glu Gln Arg Gly Pro Asp Cys
1               5                   10


<210> SEQ ID NO 218
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 218

gcttgtaata tgcatacgcc tatggtgtgc                                   30
```

<210> SEQ ID NO 219
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 219
gcttgtattc cgactcatgc taattcgtgc 30

<210> SEQ ID NO 220
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 220
gcttgtaata tgcatacgcc tatggtgtgc 30

<210> SEQ ID NO 221
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 221
gcttgtaagc tgtcgggtca tgcgccttgc 30

<210> SEQ ID NO 222
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 222
gcttgtacgt tgccgaatgg gcctaggtgc 30

<210> SEQ ID NO 223
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 223
gcttgtattc cgactcatgc taattcgtgc 30

<210> SEQ ID NO 224
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 224
gcttgtacgt tgccgaatgg gcctaggtgc 30

```
<210> SEQ ID NO 225
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 225

gcttgtattc cgactcatgc taattcgtgc                                      30


<210> SEQ ID NO 226
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 226

gcttgtaagc tgtcgggtca tgcgccttgc                                      30


<210> SEQ ID NO 227
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 227

gcttgtacgt tgccgaatgg gcctaggtgc                                      30


<210> SEQ ID NO 228
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 228

gcttgtacgt tgccgaatgg gcctaggtgc                                      30


<210> SEQ ID NO 229
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 229

gcttgtacgt tgccgaatgg gcctaggtgc                                      30


<210> SEQ ID NO 230
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 230

gcttgtattc cgactcatgc taattcgtgc                                      30


<210> SEQ ID NO 231
```

<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 231
gcttgtacgt tgccgaatgg gcctaggtgc 30

<210> SEQ ID NO 232
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 232
gcttgtattc cgactcatgc taattcgtgc 30

<210> SEQ ID NO 233
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 233

Ala Cys Asn Met His Thr Pro Met Val Cys
1 5 10

<210> SEQ ID NO 234
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 234

Ala Cys Ile Pro Thr His Ala Asn Ser Cys
1 5 10

<210> SEQ ID NO 235
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 235

Ala Cys Asn Met His Thr Pro Met Val Cys
1 5 10

<210> SEQ ID NO 236
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 236

Ala Cys Lys Leu Ser Gly His Ala Pro Cys
1 5 10

<210> SEQ ID NO 237
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 237

Ala Cys Thr Leu Pro Asn Gly Pro Arg Cys
1 5 10

<210> SEQ ID NO 238
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 238

Ala Cys Ile Pro Thr His Ala Asn Ser Cys
1 5 10

<210> SEQ ID NO 239
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 239

Ala Cys Thr Leu Pro Asn Gly Pro Arg Cys
1 5 10

<210> SEQ ID NO 240
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 240

Ala Cys Ile Pro Thr His Ala Asn Ser Cys
1 5 10

<210> SEQ ID NO 241
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 241

Ala Cys Lys Leu Ser Gly His Ala Pro Cys
1 5 10

<210> SEQ ID NO 242
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 242

Ala Cys Thr Leu Pro Asn Gly Pro Arg Cys
1 5 10

<210> SEQ ID NO 243
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 243

Ala Cys Thr Leu Pro Asn Gly Pro Arg Cys
1 5 10

<210> SEQ ID NO 244
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 244

Ala Cys Thr Leu Pro Asn Gly Pro Arg Cys
1 5 10

<210> SEQ ID NO 245
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 245

Ala Cys Ile Pro Thr His Ala Asn Ser Cys
1 5 10

<210> SEQ ID NO 246
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 246

Ala Cys Thr Leu Pro Asn Gly Pro Arg Cys
1 5 10

<210> SEQ ID NO 247
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 247

Ala Cys Ile Pro Thr His Ala Asn Ser Cys
1 5 10

<210> SEQ ID NO 248
<211> LENGTH: 10

<212> TYPE: PRT
<213> ORGANISM: Artificial Sequence
<220> FEATURE:
<223> OTHER INFORMATION: Description of Artificial Sequence: Synthetic peptide

<400> SEQUENCE: 248

Ala Cys Ile Pro Thr His Ala Asn Ser Cys
1 5 10

<210> SEQ ID NO 249
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 249

Ala Cys Thr Leu Pro Asn Gly Pro Arg Cys
1 5 10

<210> SEQ ID NO 250
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 250

Ala Cys Lys Leu Ser Gly His Ala Pro Cys
1 5 10

<210> SEQ ID NO 251
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 251

Ala Cys Asn Met His Thr Pro Met Val Cys
1 5 10

<210> SEQ ID NO 252
<211> LENGTH: 14
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (14)..(14)
<223> OTHER INFORMATION: Diaminopropionic acid

<400> SEQUENCE: 252

Ala Cys Ile Pro Thr His Ala Asn Ser Cys Gly Gly Gly Xaa
1 5 10

<210> SEQ ID NO 253
<211> LENGTH: 14
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (14)..(14)
<223> OTHER INFORMATION: Diaminopropionic acid

<400> SEQUENCE: 253

Ala Cys Thr Leu Pro Asn Gly Pro Arg Cys Gly Gly Gly Xaa
1 5 10

<210> SEQ ID NO 254
<211> LENGTH: 14
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (14)..(14)
<223> OTHER INFORMATION: Diaminopropionic acid

<400> SEQUENCE: 254

Ala Cys Thr Leu Pro Asn Gly Pro Arg Cys Gly Gly Gly Xaa
1 5 10

<210> SEQ ID NO 255
<211> LENGTH: 14
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (14)..(14)
<223> OTHER INFORMATION: Diaminopropionic acid

<400> SEQUENCE: 255

Ala Cys Thr Leu Pro Asn Gly Pro Arg Cys Gly Gly Gly Xaa
1 5 10

<210> SEQ ID NO 256
<211> LENGTH: 14
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (14)..(14)
<223> OTHER INFORMATION: Diaminopropionic acid

<400> SEQUENCE: 256

Ala Cys Thr Leu Pro Asn Gly Pro Arg Cys Gly Gly Gly Xaa
1 5 10

<210> SEQ ID NO 257
<211> LENGTH: 14
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (14)..(14)
<223> OTHER INFORMATION: Diaminopropionic acid

<400> SEQUENCE: 257

Ala Cys Lys Leu Ser Gly His Ala Pro Cys Gly Gly Gly Xaa
1 5 10

<210> SEQ ID NO 258
<211> LENGTH: 14
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (14)..(14)
<223> OTHER INFORMATION: Diaminopropionic acid

<400> SEQUENCE: 258

Ala Cys Asn Met His Thr Pro Met Val Cys Gly Gly Gly Xaa
1 5 10

<210> SEQ ID NO 259
<211> LENGTH: 14
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (14)..(14)
<223> OTHER INFORMATION: Diaminopropionic acid

<400> SEQUENCE: 259

Ala Cys Ile Pro Thr His Ala Asn Ser Cys Gly Gly Gly Xaa
1 5 10

<210> SEQ ID NO 260
<211> LENGTH: 14
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (14)..(14)
<223> OTHER INFORMATION: Diaminopropionic acid

<400> SEQUENCE: 260

Ala Cys Thr Leu Pro Asn Gly Pro Arg Cys Gly Gly Gly Xaa
1 5 10

<210> SEQ ID NO 261
<211> LENGTH: 14
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (14)..(14)
<223> OTHER INFORMATION: Diaminopropionic acid

<400> SEQUENCE: 261

Ala Cys Thr Leu Pro Asn Gly Pro Arg Cys Gly Gly Gly Xaa
1 5 10

<210> SEQ ID NO 262
<211> LENGTH: 14
<212> TYPE: PRT

<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Diaminopropionic acid

<400> SEQUENCE: 262

Ala Cys Thr Leu Pro Asn Gly Pro Arg Cys Gly Gly Gly Xaa
1               5                   10

<210> SEQ ID NO 263
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Diaminopropionic acid

<400> SEQUENCE: 263

Ala Cys Thr Leu Pro Asn Gly Pro Arg Cys Gly Gly Gly Xaa
1               5                   10

<210> SEQ ID NO 264
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Diaminopropionic acid

<400> SEQUENCE: 264

Ala Cys Lys Leu Ser Gly His Ala Pro Cys Gly Gly Gly Xaa
1               5                   10

<210> SEQ ID NO 265
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Diaminopropionic acid

<400> SEQUENCE: 265

Ala Cys Asn Met His Thr Pro Met Val Cys Gly Gly Gly Xaa
1               5                   10

<210> SEQ ID NO 266
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

```
Gly Gly Gly Ser Ile Asp Gly Arg
1               5


<210> SEQ ID NO 267
<211> LENGTH: 4
<212> TYPE: PRT
<213> ORGANISM: Unknown
<220> FEATURE:
<223> OTHER INFORMATION: Description of Unknown:
      Factor Xa cleavage site

<400> SEQUENCE: 267

Ile Asp Gly Arg
1


<210> SEQ ID NO 268
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(9)
<223> OTHER INFORMATION: Any amino acid

<400> SEQUENCE: 268

Ala Cys Xaa Xaa Xaa Xaa Xaa Xaa Xaa Cys Gly Gly Gly
1               5                   10


<210> SEQ ID NO 269
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(9)
<223> OTHER INFORMATION: Any amino acid

<400> SEQUENCE: 269

Ala Cys Xaa Xaa Xaa Xaa Xaa Xaa Xaa Cys Gly Gly Gly
1               5                   10


<210> SEQ ID NO 270
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(6)
<223> OTHER INFORMATION: Any amino acid
<220> FEATURE:
<221> NAME/KEY: MISC_FEATURE
<222> LOCATION: (3)..(6)
<223> OTHER INFORMATION: This region may encompass 1-4 residues
<220> FEATURE:
<221> NAME/KEY: MOD_RES
<222> LOCATION: (10)..(13)
<223> OTHER INFORMATION: Any amino acid
<220> FEATURE:
<221> NAME/KEY: MISC_FEATURE
<222> LOCATION: (10)..(13)
<223> OTHER INFORMATION: This region may encompass 1-4 residues

<400> SEQUENCE: 270
```

Ala Cys Xaa Xaa Xaa Xaa Cys Gly Lys Xaa Xaa Xaa Xaa Lys
1 5 10

<210> SEQ ID NO 271
<211> LENGTH: 13
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (3)..(9)
<223> OTHER INFORMATION: Any amino acid

<400> SEQUENCE: 271

Ala Cys Xaa Xaa Xaa Xaa Xaa Xaa Xaa Cys Gly Gly Gly
1 5 10

<210> SEQ ID NO 272
<211> LENGTH: 13
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (3)..(9)
<223> OTHER INFORMATION: Any amino acid

<400> SEQUENCE: 272

Ala Cys Xaa Xaa Xaa Xaa Xaa Xaa Xaa Cys Gly Gly Gly
1 5 10

<210> SEQ ID NO 273
<211> LENGTH: 13
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (3)..(9)
<223> OTHER INFORMATION: Any amino acid

<400> SEQUENCE: 273

Ala Cys Xaa Xaa Xaa Xaa Xaa Xaa Xaa Cys Gly Gly Gly
1 5 10

<210> SEQ ID NO 274
<211> LENGTH: 13
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (3)..(9)
<223> OTHER INFORMATION: Any amino acid

<400> SEQUENCE: 274

Ala Cys Xaa Xaa Xaa Xaa Xaa Xaa Xaa Cys Gly Gly Gly
1 5 10

<210> SEQ ID NO 275
<211> LENGTH: 14

<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (14)..(14)
<223> OTHER INFORMATION: Diaminopropionic acid

<400> SEQUENCE: 275

Ala Cys Val Ser Pro Arg Ser His Glu Cys Gly Gly Gly Xaa
1 5 10

<210> SEQ ID NO 276
<211> LENGTH: 14
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (14)..(14)
<223> OTHER INFORMATION: Diaminopropionic acid

<400> SEQUENCE: 276

Ala Cys Gly Pro Thr Ala Lys Tyr Ile Cys Gly Gly Gly Xaa
1 5 10

<210> SEQ ID NO 277
<211> LENGTH: 14
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (14)..(14)
<223> OTHER INFORMATION: Diaminopropionic acid

<400> SEQUENCE: 277

Ala Cys Val Ser Pro Arg Ser His Glu Cys Gly Gly Gly Xaa
1 5 10

<210> SEQ ID NO 278
<211> LENGTH: 20
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (3)..(5)
<223> OTHER INFORMATION: Any amino acid
<220> FEATURE:
<221> NAME/KEY: MOD_RES
<222> LOCATION: (9)..(11)
<223> OTHER INFORMATION: Any amino acid

<400> SEQUENCE: 278

Ala Cys Xaa Xaa Xaa Cys Gly Lys Xaa Xaa Xaa Lys Gly Gly Gly Ser
1 5 10 15

Ile Asp Gly Arg
20

<210> SEQ ID NO 279
<211> LENGTH: 20

<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (3)..(5)
<223> OTHER INFORMATION: Any amino acid
<220> FEATURE:
<221> NAME/KEY: MOD_RES
<222> LOCATION: (9)..(11)
<223> OTHER INFORMATION: Any amino acid

<400> SEQUENCE: 279

Ala Cys Xaa Xaa Xaa Cys Gly Lys Xaa Xaa Xaa Lys Gly Gly Gly Ser
1 5 10 15

Ile Asp Gly Arg
20

<210> SEQ ID NO 280
<211> LENGTH: 20
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (3)..(5)
<223> OTHER INFORMATION: Any amino acid
<220> FEATURE:
<221> NAME/KEY: MOD_RES
<222> LOCATION: (9)..(11)
<223> OTHER INFORMATION: Any amino acid

<400> SEQUENCE: 280

Ala Cys Xaa Xaa Xaa Cys Gly Lys Xaa Xaa Xaa Lys Gly Gly Gly Ser
1 5 10 15

Ile Asp Gly Arg
20

<210> SEQ ID NO 281
<211> LENGTH: 20
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (3)..(5)
<223> OTHER INFORMATION: Any amino acid
<220> FEATURE:
<221> NAME/KEY: MOD_RES
<222> LOCATION: (9)..(11)
<223> OTHER INFORMATION: Any amino acid -continued

```
<400> SEQUENCE: 281

Ala Cys Xaa Xaa Xaa Cys Gly Lys Xaa Xaa Xaa Lys Gly Gly Gly Ser
1               5                   10                  15

Ile Asp Gly Arg
            20


<210> SEQ ID NO 282
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 282

Cys Asn Gly Arg Cys Gly Lys Arg Gly Asp Phe Lys
1               5                   10
```